United States Patent
Gross et al.

(10) Patent No.: US 11,136,362 B2
(45) Date of Patent: Oct. 5, 2021

(54) PEPTIDE MODULATORS OF SPECIFIC CALCINEURIN PROTEIN-PROTEIN INTERACTIONS

(71) Applicant: The Board of Trustees of the Leland Stanford Junior University, Stanford, CA (US)

(72) Inventors: Eric Gross, Menlo Park, CA (US); Carl Hurt, Stanford, CA (US); Daria Mochly-Rosen, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 109 days.

(21) Appl. No.: 16/082,313

(22) PCT Filed: Mar. 8, 2017

(86) PCT No.: PCT/US2017/021363
§ 371 (c)(1),
(2) Date: Sep. 5, 2018

(87) PCT Pub. No.: WO2017/156128
PCT Pub. Date: Sep. 14, 2017

(65) Prior Publication Data
US 2019/0085040 A1    Mar. 21, 2019

Related U.S. Application Data

(60) Provisional application No. 62/306,244, filed on Mar. 10, 2016.

(51) Int. Cl.
| | | |
|---|---|---|
| C07K 14/47 | (2006.01) | |
| A61P 9/00 | (2006.01) | |
| A61K 9/00 | (2006.01) | |
| A61K 38/00 | (2006.01) | |
| A61K 45/06 | (2006.01) | |
| A61P 41/00 | (2006.01) | |

(52) U.S. Cl.
CPC ............ *C07K 14/47* (2013.01); *A61K 9/0014* (2013.01); *A61K 9/0019* (2013.01); *A61K 45/06* (2013.01); *A61P 9/00* (2018.01); *A61P 41/00* (2018.01); *A61K 38/00* (2013.01); *C07K 2319/10* (2013.01)

(58) Field of Classification Search
CPC .... C07K 14/47; C07K 2319/10; A61K 38/00; A61P 9/00
See application file for complete search history.

(56) References Cited

U.S. PATENT DOCUMENTS

| 10,010,588 B2 * | 7/2018 | Mumm ...................... A61P 9/00 |
| 2006/0292639 A1 | 12/2006 | Mansson et al. |
| 2011/0166196 A1 | 7/2011 | Kauer et al. |
| 2018/0111990 A1 * | 4/2018 | Orwar .................. C07K 14/705 |

OTHER PUBLICATIONS

Chung et al. (Jan. 2015) "Peripheral Group I Metabotropic Glutamate Receptor Activation Leads to Muscle Mechanical Hyperalgesia Through TRPV1 Phosphorylation in the Rat," *J Pain* 16(10):67-76.
Hurt et al. (2012) "Transient Receptor Potential Vanilloid 1 Regulates Mitochondrial Membrane Potential and Myocardial Reperfusion Injury," *Journal of the American Heart Association* 5:e003774, 39 pgs.
Gross et al. (Nov. 2014) "Abstract 17443: Inhibition of the Calcineurin Interaction Site on TRPV1 Reduces Myocardial Infarct Size in Rats," *Circulation* pp. 1-6.
Kim et al. (Oct. 2006) "Transient Receptor Potential Vanilloid Subtype 1 Mediates Microglial Cell Death in Vivo and In Vitro via Ca2+ Mediated Mitochondrial Damage and Cytochrome C Release," *J Immunol* 177(7):4322-4329.
Li et al. (2012) "Balanced Interactions of Calcineurin with AKAP79 Regulate Calcium-Calcineruin-NFAT Signaling," *Nature Structural Molecular Biology* 19(3):337-345.
Li et al. (2011) "Interaction of Calcineurin with Substrates and Targeting Proteins," *Trends Cell Biol.* 21(2):91-103.
International Search Report and Written Opinion dated Jul. 19, 2017 for corresponding PCT Patent Application No. PCT/US2017/021363 filed on Mar. 8, 2017, 22 pages.

* cited by examiner

*Primary Examiner* — Ruixiang Li
(74) *Attorney, Agent, or Firm* — Bret E. Field; Bozicevic, Field & Francis LLP

(57) ABSTRACT

Methods of modulating the interaction between calcineurin and a calcineurin-binding protein partner are provided. Aspects of the methods include contacting a cell with a peptidic agent that modulates the interaction between calcineurin and a TRPV channel. Also provided are pharmaceutical compositions that comprise a peptidic agent that selectively modulates the interaction between calcineurin and a calcineurin-binding protein partner. Also provided are methods of treating a condition in a subject by selectively modulating the interaction between calcineurin and a calcineurin-binding TRPV channel. Also provided are screening methods to identify candidate agents that modulate calcineurin protein-protein interactions.

10 Claims, 23 Drawing Sheets

Specification includes a Sequence Listing.

FIG. 3
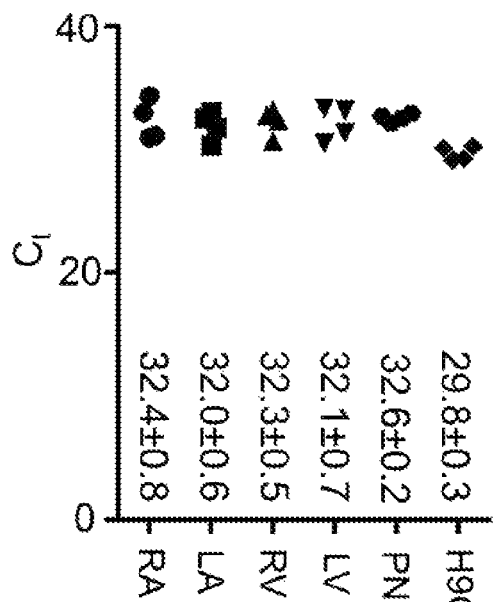
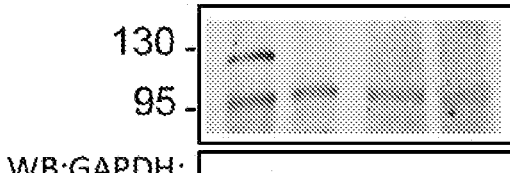
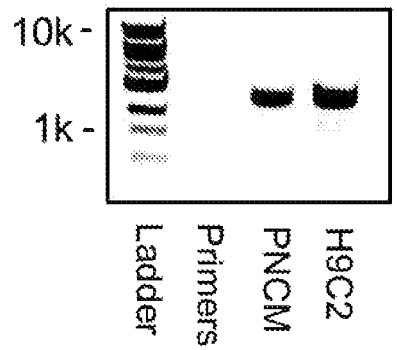
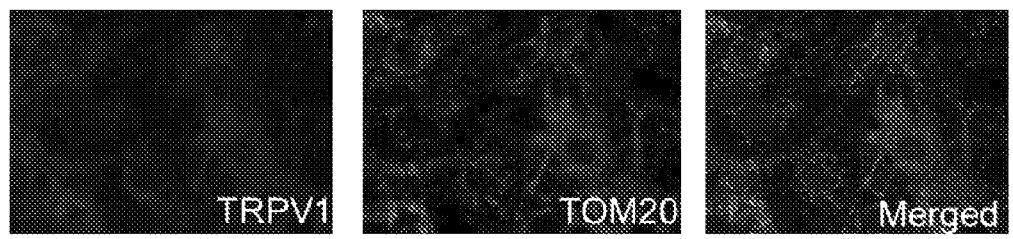
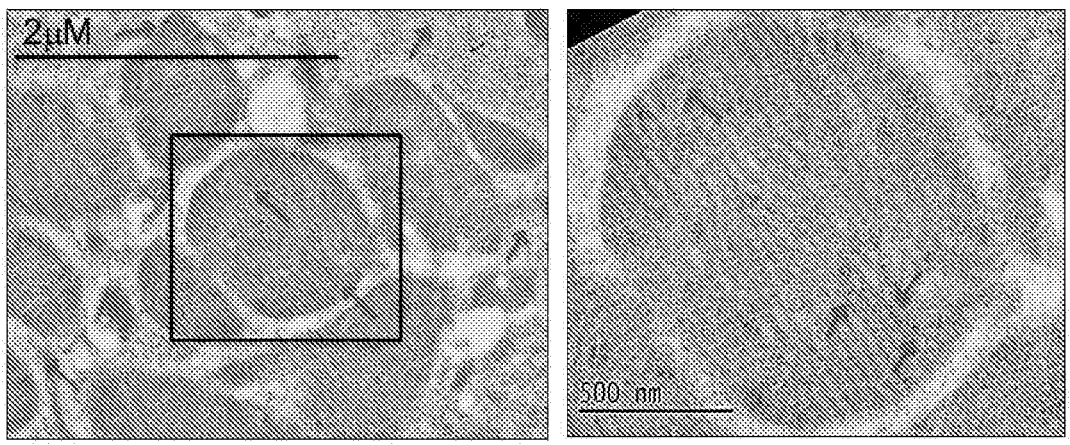

FIG. 4
A.
Wild type cardiomyocytes
TRPV1
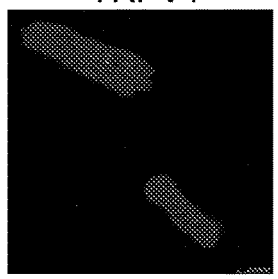
DAPI
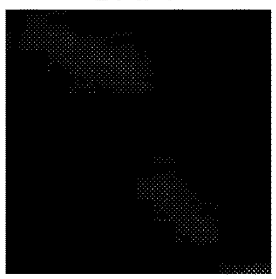
B.
Knockout TRPV1 cardiomyocytes
TRPV1
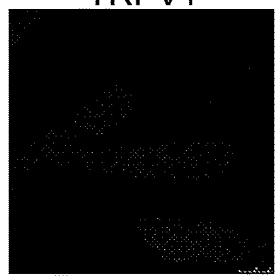
DAPI
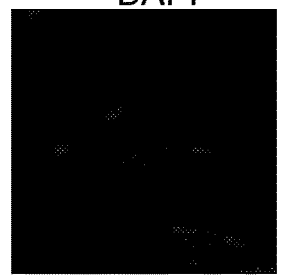
TOM20
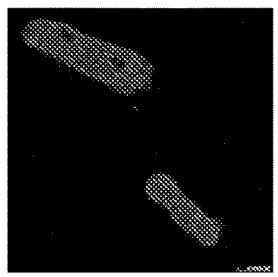
Merged
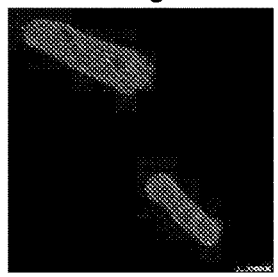

FIG. 5

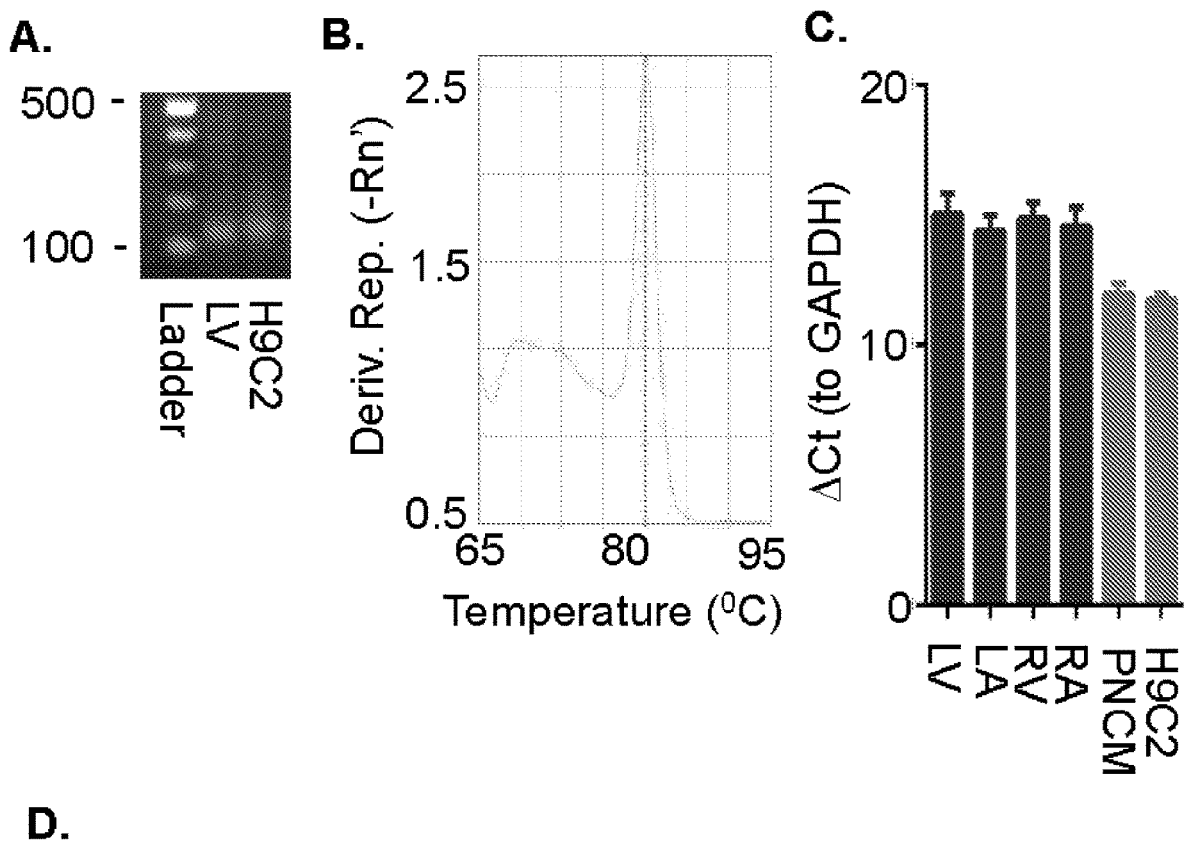

D.

```
ATEDLERMEQRASLDSEESESPPQENSCLDPPDRDPNCKPPPVKPHIFTTRSRTRLFGKG    60
DSEEASPLDCPYEEGGLASCPIITVSSVLTIQRPGDGPASVRPSSQDSVSAGEKPPRLYD   120
RRSIFDAVAQSNCQELESLLPFLQRSKKRLTDSEFKDPETGKTCLLKAMLNLHNGQNDTI   180
ALLLDVARKTDSLKQFVNASYTDSYYKGQTALHIAIERRNMTLVTLLVENGADVQAAANG   240
DFFKKTKGRPGFYFGELPLSLAACTNQLAIVKFLLQNSWQPADISARDSVGNTVLHALVE   300
VADNTVDNTKFVTSMYNEILILGAKLHPTLKLEEITNRKGLTPLALAASSGKIGVLAYIL   360
QREIHEPECRHLSRKFTEWAYGPVHSSLYDLSCIDTCEKNSVLEVIAYSSSETPNRHDML   420
LVEPLNRLLQDKWDRFVKRIFYFNFFVYCLYMIIFTAAAYYRPVEGLPPYKLKNTVGDYF   480
RVTGEILSVSGGVYFFFRGIQYFLQRRPSLKSLFVDSYSEILFFVQSLFMLVSVVLYFSQ   540
RKEYVASMVFSLAMGWTNMLYYTRGFQQMGIYAVMIEKMILRDLCRFMFVYLVFLFGFST   600
AVVTLIEDGKNNSLPMESTPHKCRGSACKPGNSYNSLYSTCLELFKFTIGMGDLEFTENY   660
DFKAVFIILLLAYVILTYILLLNMLIALMGETVNKIAQESKNIWKLQRAITILDTEKSFL   720
KCMRKAFRSGKLLQVGFTPDGKDDYRWCFRVDEVNWTTWNTNVGIINEDPGNCEGVKRTL   780
SFSLRSGRVSGRNWKNFALVPLLRDASTRDRHATQQEEVQLKHYTGSLKPEDAEVFKDSM   840
VPGEK*WTLCRDQCGVFGWSA*GTSRV
```

FIG. 9
A.
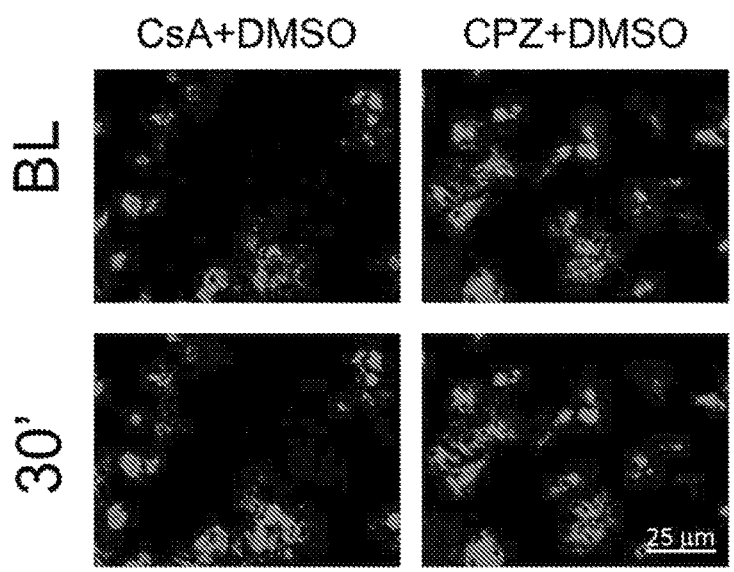
B.
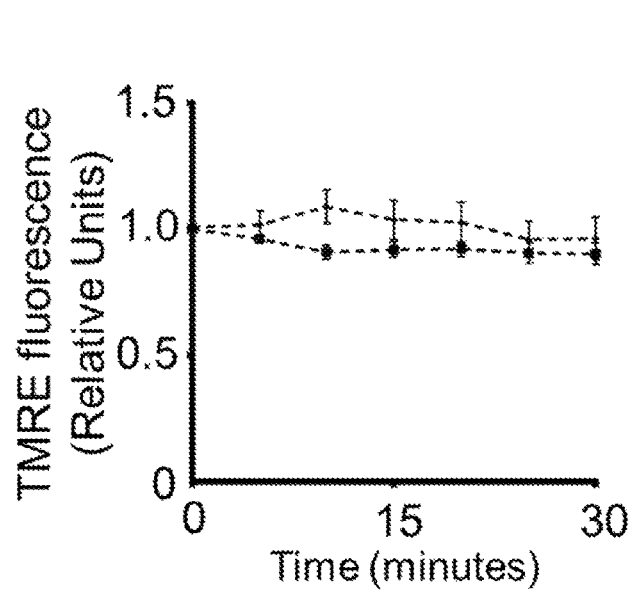
C.
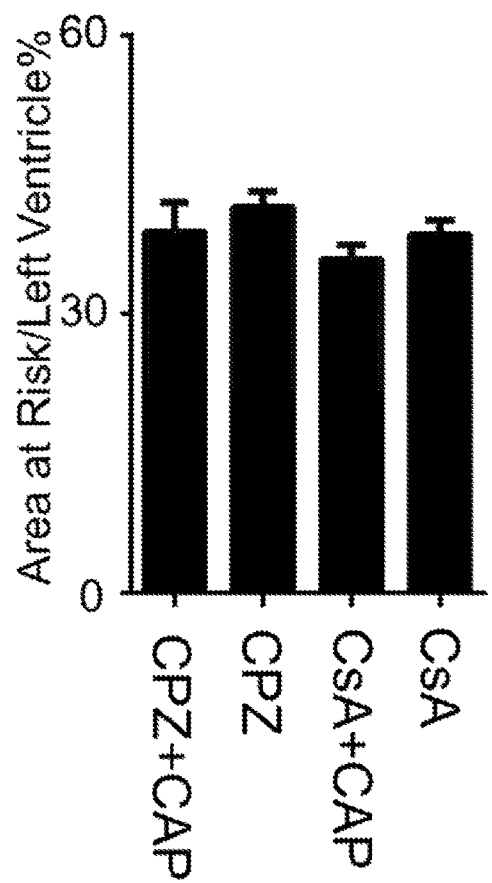

FIG. 10
A.
```
        336              348
AKAP5   EPIAHITDTEIS
         : :   : : :   :
TRPV1   LQRAITILDTEKS
        699              711
```
B. 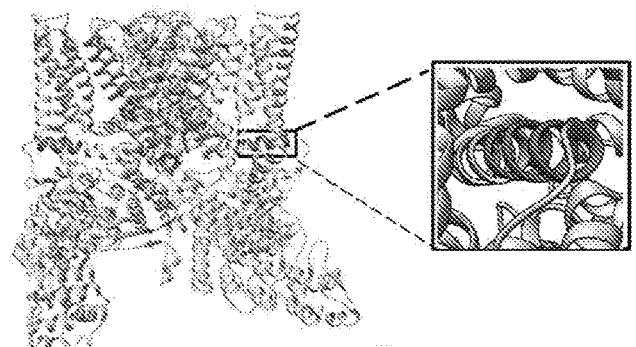
C. 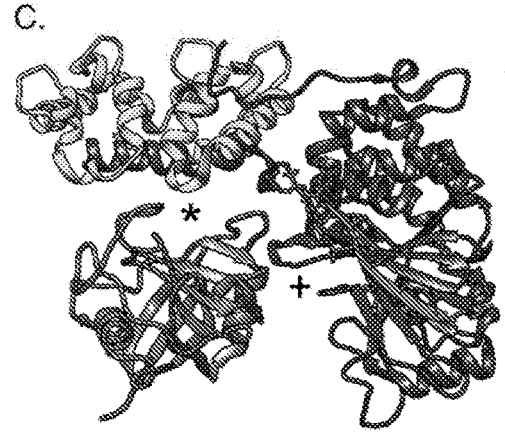
D. 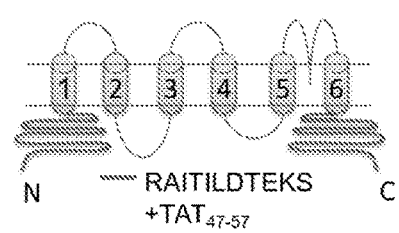
N —RAITILDTEKS— C
 +TAT$_{47-57}$
E. 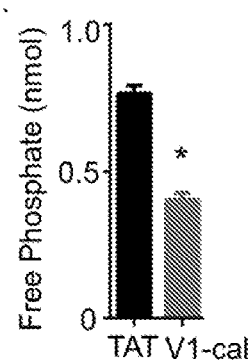

A.

TRPV1 701-711

| | |
|---|---|
| RAITILDTEKS | Human (839 aa) |
| RAITILDTEKS | Cow (837 aa) |
| RAITILDTEKS | Rat (838 aa) |
| RAITILDTEKS | Mouse (839 aa) |
| RAITILDTEKS | Guinea Pig (839 aa) |
| RAITILDTEKG | Rabbit (842 aa) |
| RAITILDTEKS | Canine (840 aa) |

B.

FIG. 12
A. Baseline (0 minutes)
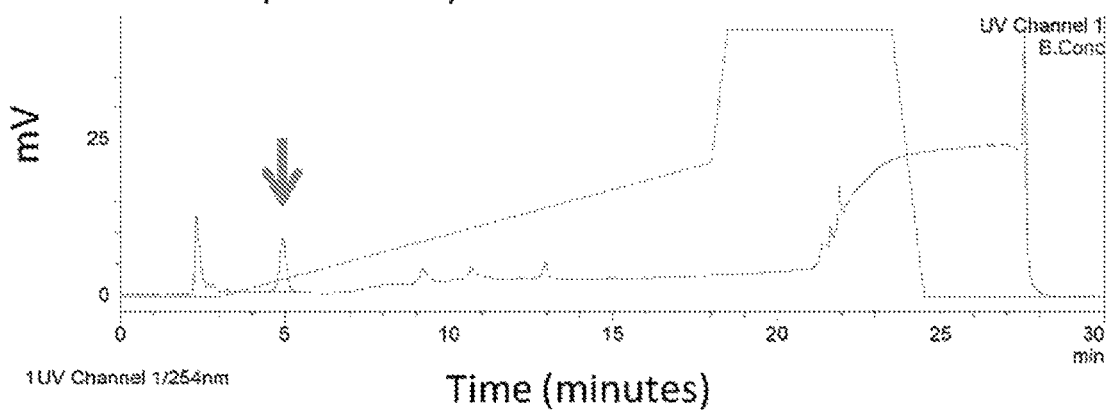
B. 10 minutes after trypsin
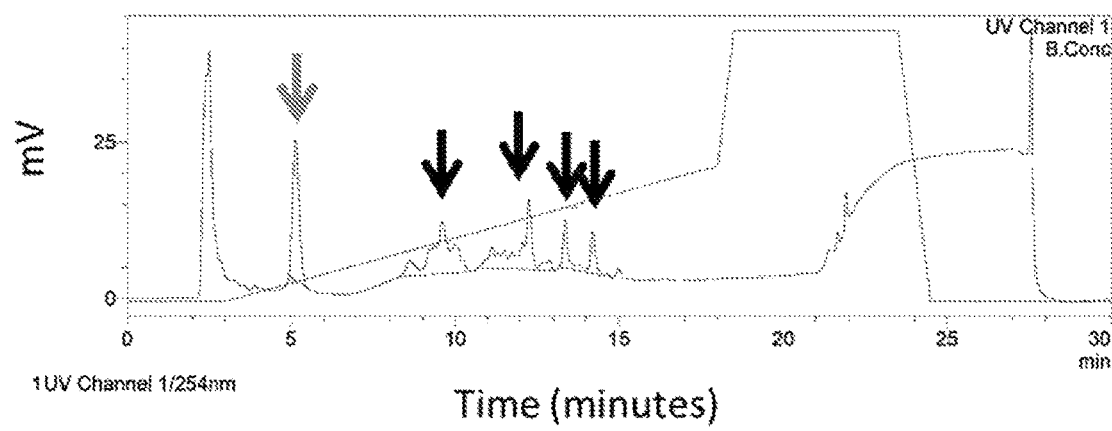
C. 20 minutes after trypsin
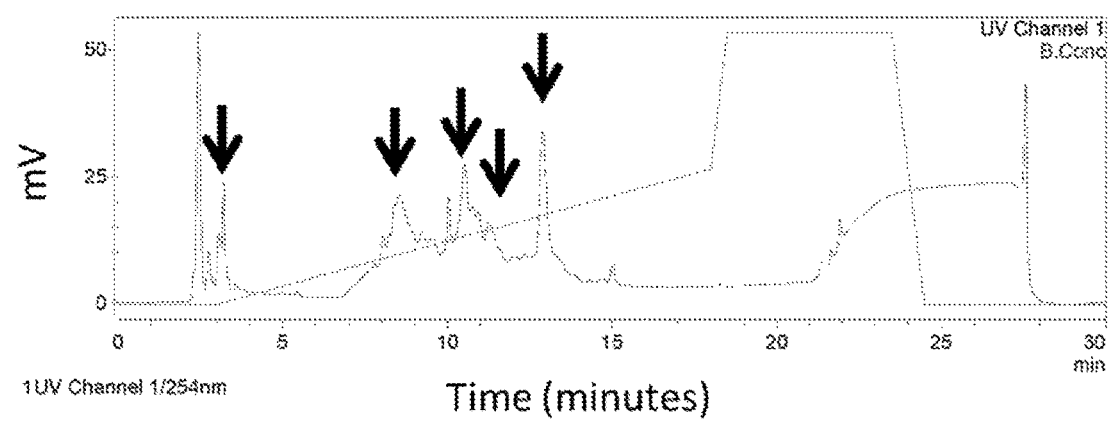

FIG. 19
A. TRPV1: IWKLQRAITILDTEKSFLKCMRKAFR
B.
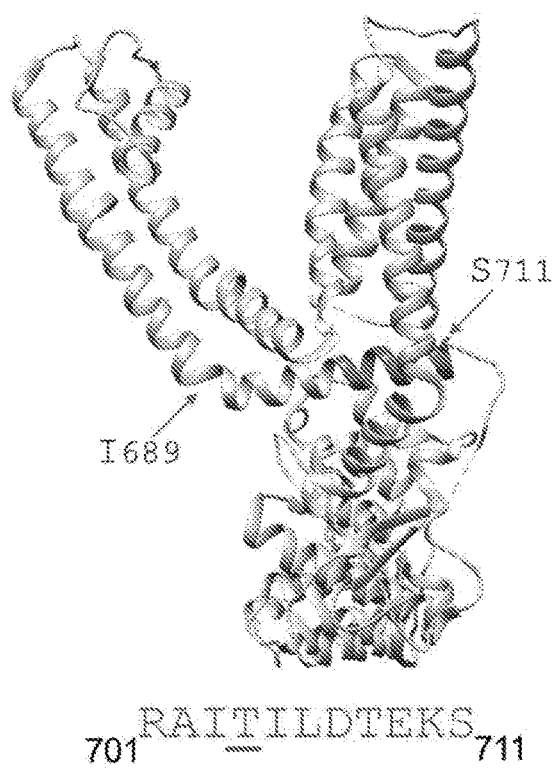
C.
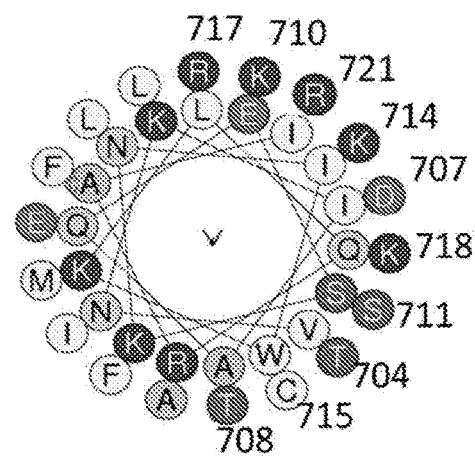
D.
- P1: RAITILDTEKS
- P2: QRAITILDTEKSFLKCMRKAFR
- P3: QRAITILDTEKS
- P4: AITILDTEKSFLK
- P5: ITILDTEKSFLKCMRKAFR
- P6: ITILDTEKSFLKCMRK
- P7: AITILDTEKSFLK
- P8: ITILDTEKSF
- P9: ITILDTEKSFLKCM

FIG. 20
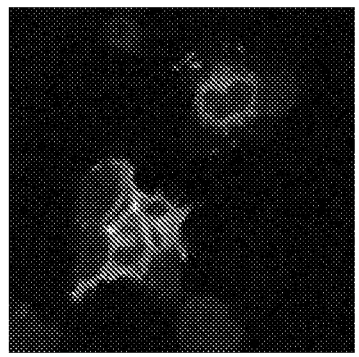
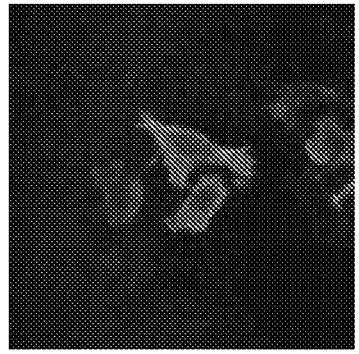
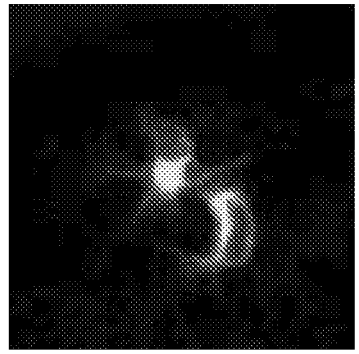

FIG. 21
A 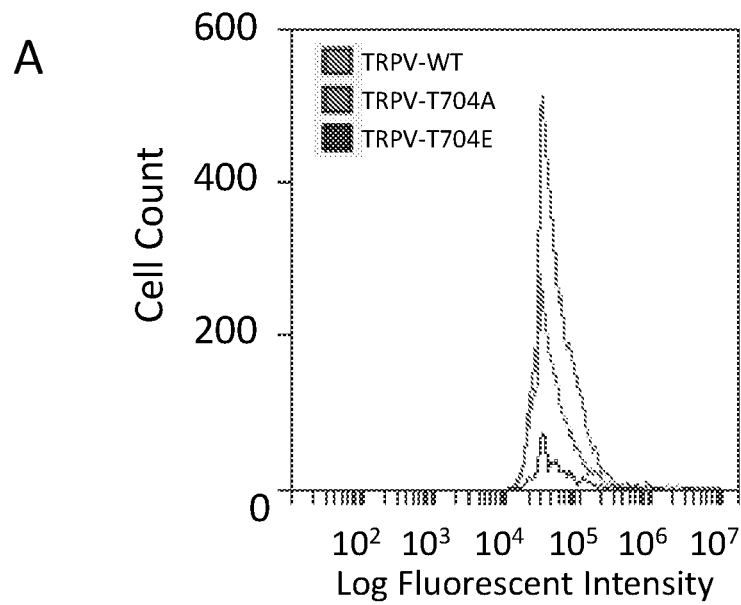
B 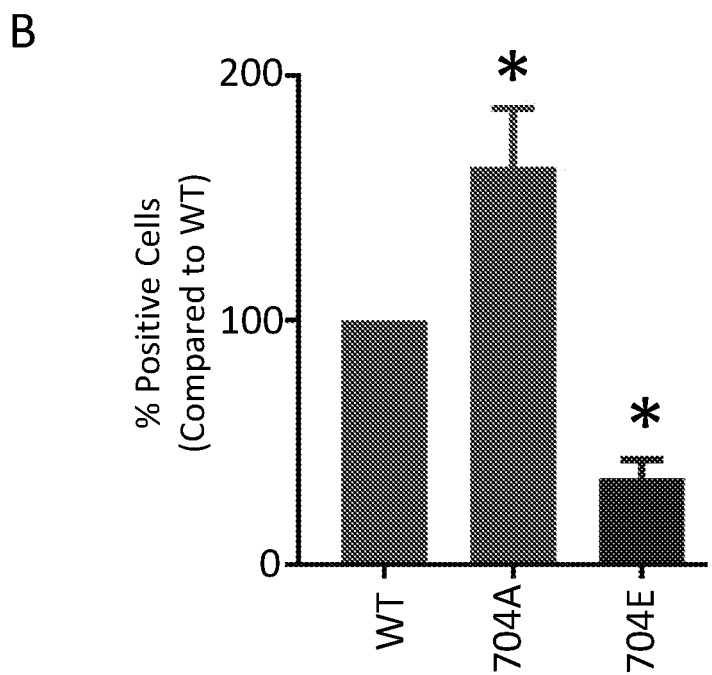

FIG. 22
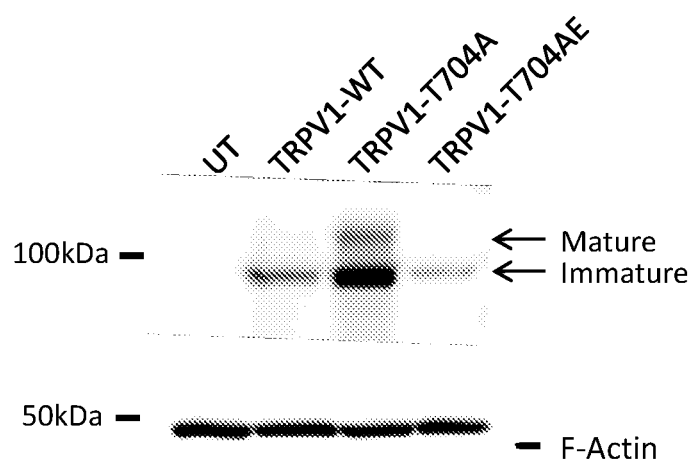
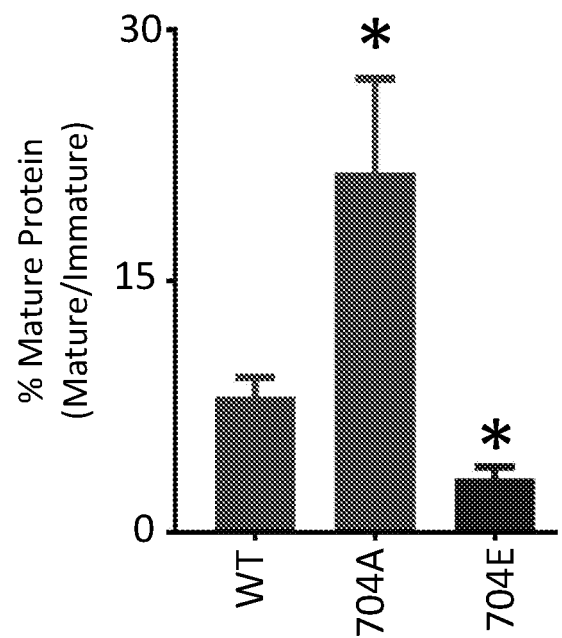

SEQUENCE LISTING

```
<160> NUMBER OF SEQ ID NOS: 116

<210> SEQ ID NO 1
<211> LENGTH: 865
<212> TYPE: PRT
<213> ORGANISM: Artificial Sequence
<220> FEATURE:
<223> OTHER INFORMATION: Synthetic polypeptide

<400> SEQUENCE: 1

Ala Thr Glu Asp Leu Glu Arg Met Glu Gln Arg Ala Ser Leu Asp Ser
1               5                   10                  15

Glu Glu Ser Glu Ser Pro Pro Gln Glu Asn Ser Cys Leu Asp Pro Pro
            20                  25                  30
```

```
Asp Arg Asp Pro Asn Cys Lys Pro Pro Val Lys Pro His Ile Phe
        35              40                  45

Thr Thr Arg Ser Arg Thr Arg Leu Phe Gly Lys Gly Asp Ser Glu Glu
 50                  55                  60

Ala Ser Pro Leu Asp Cys Pro Tyr Glu Glu Gly Gly Leu Ala Ser Cys
 65              70                  75                      80

Pro Ile Ile Thr Val Ser Ser Val Leu Thr Ile Gln Arg Pro Gly Asp
                 85                  90                  95

Gly Pro Ala Ser Val Arg Pro Ser Ser Gln Asp Ser Val Ser Ala Gly
            100                 105                 110

Glu Lys Pro Pro Arg Leu Tyr Asp Arg Arg Ser Ile Phe Asp Ala Val
        115                 120                 125

Ala Gln Ser Asn Cys Gln Glu Leu Glu Ser Leu Leu Pro Phe Leu Gln
    130                 135                 140

Arg Ser Lys Lys Arg Leu Thr Asp Ser Glu Phe Lys Asp Pro Glu Thr
145                 150                 155                 160

Gly Lys Thr Cys Leu Leu Lys Ala Met Leu Asn Leu His Asn Gly Gln
                165                 170                 175

Asn Asp Thr Ile Ala Leu Leu Leu Asp Val Ala Arg Lys Thr Asp Ser
            180                 185                 190

Leu Lys Gln Phe Val Asn Ala Ser Tyr Thr Asp Ser Tyr Tyr Lys Gly
        195                 200                 205

Gln Thr Ala Leu His Ile Ala Ile Glu Arg Arg Asn Met Thr Leu Val
    210                 215                 220

Thr Leu Leu Val Glu Asn Gly Ala Asp Val Gln Ala Ala Ala Asn Gly
225                 230                 235                 240

Asp Phe Phe Lys Lys Thr Lys Gly Arg Pro Gly Phe Tyr Phe Gly Glu
                245                 250                 255

Leu Pro Leu Ser Leu Ala Ala Cys Thr Asn Gln Leu Ala Ile Val Lys
            260                 265                 270

Phe Leu Leu Gln Asn Ser Trp Gln Pro Ala Asp Ile Ser Ala Arg Asp
        275                 280                 285

Ser Val Gly Asn Thr Val Leu His Ala Leu Val Glu Val Ala Asp Asn
290                 295                 300

Thr Val Asp Asn Thr Lys Phe Val Thr Ser Met Tyr Asn Glu Ile Leu
305                 310                 315                 320

Ile Leu Gly Ala Lys Leu His Pro Thr Leu Lys Leu Glu Glu Ile Thr
                325                 330                 335

Asn Arg Lys Gly Leu Thr Pro Leu Ala Leu Ala Ala Ser Ser Gly Lys
            340                 345                 350

Ile Gly Val Leu Ala Tyr Ile Leu Gln Arg Glu Ile His Glu Pro Glu
        355                 360                 365

Cys Arg His Leu Ser Arg Lys Phe Thr Glu Trp Ala Tyr Gly Pro Val
370                 375                 380

His Ser Ser Leu Tyr Asp Leu Ser Cys Ile Asp Thr Cys Glu Lys Asn
385                 390                 395                 400

Ser Val Leu Glu Val Ile Ala Tyr Ser Ser Ser Glu Thr Pro Asn Arg
                405                 410                 415

His Asp Met Leu Leu Val Glu Pro Leu Asn Arg Leu Leu Gln Asp Lys
            420                 425                 430

Trp Asp Arg Phe Val Lys Arg Ile Phe Tyr Phe Asn Phe Val Tyr
        435                 440                 445
```

```
Cys Leu Tyr Met Ile Ile Phe Thr Ala Ala Ala Tyr Arg Pro Val
    450                 455                 460
Glu Gly Leu Pro Pro Tyr Lys Leu Lys Asn Thr Val Gly Asp Tyr Phe
465                 470                 475                 480
Arg Val Thr Gly Glu Ile Leu Ser Val Ser Gly Val Tyr Phe Phe
                485                 490                 495
Phe Arg Gly Ile Gln Tyr Phe Leu Gln Arg Pro Ser Leu Lys Ser
            500                 505                 510
Leu Phe Val Asp Ser Tyr Ser Glu Ile Leu Phe Val Gln Ser Leu
        515                 520                 525
Phe Met Leu Val Ser Val Val Leu Tyr Phe Ser Gln Arg Lys Glu Tyr
530                 535                 540
Val Ala Ser Met Val Phe Ser Leu Ala Met Gly Trp Thr Asn Met Leu
545                 550                 555                 560
Tyr Tyr Thr Arg Gly Phe Gln Gln Met Gly Ile Tyr Ala Val Met Ile
                565                 570                 575
Glu Lys Met Ile Leu Arg Asp Leu Cys Arg Phe Met Phe Val Tyr Leu
            580                 585                 590
Val Phe Leu Phe Gly Phe Ser Thr Ala Val Val Thr Leu Ile Glu Asp
        595                 600                 605
Gly Lys Asn Asn Ser Leu Pro Met Glu Ser Thr Pro His Lys Cys Arg
610                 615                 620
Gly Ser Ala Cys Lys Pro Gly Asn Ser Tyr Asn Ser Leu Tyr Ser Thr
625                 630                 635                 640
Cys Leu Glu Leu Phe Lys Phe Thr Ile Gly Met Gly Asp Leu Glu Phe
                645                 650                 655
Thr Glu Asn Tyr Asp Phe Lys Ala Val Phe Ile Ile Leu Leu Leu Ala
            660                 665                 670
Tyr Val Ile Leu Thr Tyr Ile Leu Leu Leu Asn Met Leu Ile Ala Leu
        675                 680                 685
Met Gly Glu Thr Val Asn Lys Ile Ala Gln Glu Ser Lys Asn Ile Trp
690                 695                 700
Lys Leu Gln Arg Ala Ile Thr Ile Leu Asp Thr Glu Lys Ser Phe Leu
705                 710                 715                 720
Lys Cys Met Arg Lys Ala Phe Arg Ser Gly Lys Leu Leu Gln Val Gly
                725                 730                 735
Phe Thr Pro Asp Gly Lys Asp Asp Tyr Arg Trp Cys Phe Arg Val Asp
            740                 745                 750
Glu Val Asn Trp Thr Thr Trp Asn Thr Asn Val Gly Ile Ile Asn Glu
        755                 760                 765
Asp Pro Gly Asn Cys Glu Gly Val Lys Arg Thr Leu Ser Phe Ser Leu
770                 775                 780
Arg Ser Gly Arg Val Ser Gly Arg Asn Trp Lys Asn Phe Ala Leu Val
785                 790                 795                 800
Pro Leu Leu Arg Asp Ala Ser Thr Arg Asp Arg His Ala Thr Gln Gln
                805                 810                 815
Glu Glu Val Gln Leu Lys His Tyr Thr Gly Ser Leu Lys Pro Glu Asp
            820                 825                 830
Ala Glu Val Phe Lys Asp Ser Met Val Pro Gly Glu Lys Trp Thr Leu
        835                 840                 845
Cys Arg Asp Gln Cys Gly Val Phe Gly Trp Ser Ala Gly Thr Ser Arg
850                 855                 860

Val
```

<210> SEQ ID NO 2
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 2

Glu Pro Ile Ala Ile Ile Ile Thr Asp Thr Glu Ile Ser
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 3

Leu Gln Arg Ala Ile Thr Ile Leu Asp Thr Glu Lys Ser
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 4

Arg Ala Ile Thr Ile Leu Asp Thr Glu Lys Ser
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 5

Arg Ala Ile Thr Ile Leu Asp Thr Glu Lys Gly
1               5                   10

<210> SEQ ID NO 6
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 6

Ile Trp Lys Leu Gln Arg Ala Ile Thr Ile Leu Asp Thr Glu Lys Ser
1               5                   10                  15

Phe Leu Lys Cys Met Arg Lys Ala Phe Arg
            20                  25

<210> SEQ ID NO 7
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 7

```
Gln Arg Ala Ile Thr Ile Leu Asp Thr Glu Lys Ser Phe Leu Lys Cys
1               5                   10                  15

Met Arg Lys Ala Phe Arg
            20

<210> SEQ ID NO 8
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 8

Gln Arg Ala Ile Thr Ile Leu Asp Thr Glu Lys Ser
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 9

Ala Ile Thr Ile Leu Asp Thr Glu Lys Ser Phe Leu Lys
1               5                   10

<210> SEQ ID NO 10
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 10

Ile Thr Ile Leu Asp Thr Glu Lys Ser Phe Leu Lys Cys Met Arg Lys
1               5                   10                  15

Ala Phe Arg

<210> SEQ ID NO 11
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 11

Ile Thr Ile Leu Asp Thr Glu Lys Ser Phe Leu Lys Cys Met Arg Lys
1               5                   10                  15

<210> SEQ ID NO 12
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 12

Ala Ile Thr Ile Leu Asp Thr Glu Lys Ser Phe Leu Lys
1               5                   10

<210> SEQ ID NO 13
<211> LENGTH: 10
<212> TYPE: PRT
<213> ORGANISM: Artificial Sequence
```

<220> FEATURE:
<223> OTHER INFORMATION: Synthetic polypeptide

<400> SEQUENCE: 13

Ile Thr Ile Leu Asp Thr Glu Lys Ser Phe
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 14

Ile Thr Ile Leu Asp Thr Glu Lys Ser Phe Leu Lys Cys Met
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 3, 5, 9
<223> OTHER INFORMATION: Xaa = Any Amino Acid

<400> SEQUENCE: 15

Ala Ile Xaa Ile Xaa Asp Thr Glu Xaa Ser
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 16

Gln Arg Ala Arg Thr Ile Leu Glu Phe Glu Lys Met
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 17

Gln Trp Ala Thr Thr Ile Leu Asp Ile Glu Arg Ser
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 18

Gln Lys Ala Ile Ser Val Leu Glu Met Glu Asn Gly
1               5                   10

<210> SEQ ID NO 19

```
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 19

Gln Val Val Ala Thr Thr Val Met Leu Glu Arg Lys Leu
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 20

Gln Ile Val Ala Thr Thr Val Met Leu Glu Arg Lys Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1
<223> OTHER INFORMATION: Xaa = Any Amino Acid

<400> SEQUENCE: 21

Xaa Arg Ala Ile Thr Ile Leu Asp Thr Glu Lys Ser
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1
<223> OTHER INFORMATION: Xaa = Any Amino Acid

<400> SEQUENCE: 22

Xaa Arg Ala Arg Thr Ile Leu Glu Phe Glu Lys Met
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1
<223> OTHER INFORMATION: Xaa = Any Amino Acid

<400> SEQUENCE: 23

Xaa Trp Ala Thr Thr Ile Leu Asp Ile Glu Arg Ser
1               5                   10

<210> SEQ ID NO 24
<211> LENGTH: 12
<212> TYPE: PRT
```

<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1
<223> OTHER INFORMATION: Xaa = Any Amino Acid

<400> SEQUENCE: 24

Xaa Lys Ala Ile Ser Val Leu Glu Met Glu Asn Gly
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1
<223> OTHER INFORMATION: Xaa = Any Amino Acid

<400> SEQUENCE: 25

Xaa Val Val Ala Thr Thr Val Met Leu Glu Arg Lys Leu
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 1
<223> OTHER INFORMATION: Xaa = Any Amino Acid

<400> SEQUENCE: 26

Xaa Ile Val Ala Thr Thr Val Met Leu Glu Arg Lys Leu
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 2
<223> OTHER INFORMATION: Xaa = Any Amino Acid

<400> SEQUENCE: 27

Gln Xaa Ala Ile Thr Ile Leu Asp Thr Glu Lys Ser
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 2
<223> OTHER INFORMATION: Xaa = Any Amino Acid

<400> SEQUENCE: 28

Gln Xaa Ala Arg Thr Ile Leu Glu Phe Glu Lys Met

<210> SEQ ID NO 29
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 2
<223> OTHER INFORMATION: Xaa = Any Amino Acid

<400> SEQUENCE: 29

Gln Xaa Ala Thr Thr Ile Leu Asp Ile Glu Arg Ser
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 2
<223> OTHER INFORMATION: Xaa = Any Amino Acid

<400> SEQUENCE: 30

Gln Xaa Ala Ile Ser Val Leu Glu Met Glu Asn Gly
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 2
<223> OTHER INFORMATION: Xaa = Any Amino Acid

<400> SEQUENCE: 31

Gln Xaa Val Ala Thr Thr Val Met Leu Glu Arg Lys Leu
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 2
<223> OTHER INFORMATION: Xaa = Any Amino Acid

<400> SEQUENCE: 32

Gln Xaa Val Ala Thr Thr Val Met Leu Glu Arg Lys Leu
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 3
<223> OTHER INFORMATION: Xaa = Any Amino Acid

<400> SEQUENCE: 33

Gln Arg Xaa Ile Thr Ile Leu Asp Thr Glu Lys Ser
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 3
<223> OTHER INFORMATION: Xaa = Any Amino Acid

<400> SEQUENCE: 34

Gln Arg Xaa Arg Thr Ile Leu Glu Phe Glu Lys Met
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 3
<223> OTHER INFORMATION: Xaa = Any Amino Acid

<400> SEQUENCE: 35

Gln Trp Xaa Thr Thr Ile Leu Asp Ile Glu Arg Ser
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 3
<223> OTHER INFORMATION: Xaa = Any Amino Acid

<400> SEQUENCE: 36

Gln Lys Xaa Ile Ser Val Leu Glu Met Glu Asn Gly
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 3
<223> OTHER INFORMATION: Xaa = Any Amino Acid

<400> SEQUENCE: 37

Gln Val Xaa Ala Thr Thr Val Met Leu Glu Arg Lys Leu
1               5                   10

<210> SEQ ID NO 38
<211> LENGTH: 13

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 3
<223> OTHER INFORMATION: Xaa = Any Amino Acid

<400> SEQUENCE: 38

Gln Ile Xaa Ala Thr Thr Val Met Leu Glu Arg Lys Leu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 4
<223> OTHER INFORMATION: Xaa = Any Amino Acid

<400> SEQUENCE: 39

Gln Arg Ala Xaa Thr Ile Leu Asp Thr Glu Lys Ser
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 4
<223> OTHER INFORMATION: Xaa = Any Amino Acid

<400> SEQUENCE: 40

Gln Arg Ala Xaa Thr Ile Leu Glu Phe Glu Lys Met
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 4
<223> OTHER INFORMATION: Xaa = Any Amino Acid

<400> SEQUENCE: 41

Gln Trp Ala Xaa Thr Ile Leu Asp Ile Glu Arg Ser
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 4
<223> OTHER INFORMATION: Xaa = Any Amino Acid

<400> SEQUENCE: 42
```

```
Gln Lys Ala Xaa Ser Val Leu Glu Met Glu Asn Gly
1               5                   10
```

<210> SEQ ID NO 43
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 4
<223> OTHER INFORMATION: Xaa = Any Amino Acid

<400> SEQUENCE: 43

```
Gln Val Val Xaa Thr Thr Val Met Leu Glu Arg Lys Leu
1               5                   10
```

<210> SEQ ID NO 44
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 4
<223> OTHER INFORMATION: Xaa = Any Amino Acid

<400> SEQUENCE: 44

```
Gln Ile Val Xaa Thr Thr Val Met Leu Glu Arg Lys Leu
1               5                   10
```

<210> SEQ ID NO 45
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 5
<223> OTHER INFORMATION: Xaa = Any Amino Acid

<400> SEQUENCE: 45

```
Gln Arg Ala Ile Xaa Ile Leu Asp Thr Glu Lys Ser
1               5                   10
```

<210> SEQ ID NO 46
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 5
<223> OTHER INFORMATION: Xaa = Any Amino Acid

<400> SEQUENCE: 46

```
Gln Arg Ala Arg Xaa Ile Leu Glu Phe Glu Lys Met
1               5                   10
```

<210> SEQ ID NO 47
<211> LENGTH: 12
<212> TYPE: PRT
<213> ORGANISM: Artificial Sequence
<220> FEATURE:
<223> OTHER INFORMATION: Synthetic polypeptide
<220> FEATURE:

```
<221> NAME/KEY: VARIANT
<222> LOCATION: 5
<223> OTHER INFORMATION: Xaa = Any Amino Acid

<400> SEQUENCE: 47

Gln Trp Ala Thr Xaa Ile Leu Asp Ile Glu Arg Ser
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 5
<223> OTHER INFORMATION: Xaa = Any Amino Acid

<400> SEQUENCE: 48

Gln Lys Ala Ile Xaa Val Leu Glu Met Glu Asn Gly
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 5
<223> OTHER INFORMATION: Xaa = Any Amino Acid

<400> SEQUENCE: 49

Gln Val Val Ala Xaa Thr Val Met Leu Glu Arg Lys Leu
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 5
<223> OTHER INFORMATION: Xaa = Any Amino Acid

<400> SEQUENCE: 50

Gln Ile Val Ala Xaa Thr Val Met Leu Glu Arg Lys Leu
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 6
<223> OTHER INFORMATION: Xaa = Any Amino Acid

<400> SEQUENCE: 51

Gln Arg Ala Ile Thr Xaa Leu Asp Thr Glu Lys Ser
1               5                   10

<210> SEQ ID NO 52
```

```
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 6
<223> OTHER INFORMATION: Xaa = Any Amino Acid

<400> SEQUENCE: 52

Gln Arg Ala Arg Thr Xaa Leu Glu Phe Glu Lys Met
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 6
<223> OTHER INFORMATION: Xaa = Any Amino Acid

<400> SEQUENCE: 53

Gln Trp Ala Thr Thr Xaa Leu Asp Ile Glu Arg Ser
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 6
<223> OTHER INFORMATION: Xaa = Any Amino Acid

<400> SEQUENCE: 54

Gln Lys Ala Ile Ser Xaa Leu Glu Met Glu Asn Gly
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 6
<223> OTHER INFORMATION: Xaa = Any Amino Acid

<400> SEQUENCE: 55

Gln Val Val Ala Thr Xaa Val Met Leu Glu Arg Lys Leu
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 6
<223> OTHER INFORMATION: Xaa = Any Amino Acid

<400> SEQUENCE: 56
```

Gln Ile Val Ala Thr Xaa Val Met Leu Glu Arg Lys Leu
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 7
<223> OTHER INFORMATION: Xaa = Any Amino Acid

<400> SEQUENCE: 57

Gln Arg Ala Ile Thr Ile Xaa Asp Thr Glu Lys Ser
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 7
<223> OTHER INFORMATION: Xaa = Any Amino Acid

<400> SEQUENCE: 58

Gln Arg Ala Arg Thr Ile Xaa Glu Phe Glu Lys Met
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 7
<223> OTHER INFORMATION: Xaa = Any Amino Acid

<400> SEQUENCE: 59

Gln Trp Ala Thr Thr Ile Xaa Asp Ile Glu Arg Ser
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 7
<223> OTHER INFORMATION: Xaa = Any Amino Acid

<400> SEQUENCE: 60

Gln Lys Ala Ile Ser Val Xaa Glu Met Glu Asn Gly
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetic polypeptide

```
<220> FEATURE:
<221> NAME/KEY: VARIANT
<222> LOCATION: 7
<223> OTHER INFORMATION: Xaa = Any Amino Acid

<400> SEQUENCE: 61

Gln Val Val Ala Thr Thr Xaa Met Leu Glu Arg Lys Leu
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 7
<223> OTHER INFORMATION: Xaa = Any Amino Acid

<400> SEQUENCE: 62

Gln Ile Val Ala Thr Thr Xaa Met Leu Glu Arg Lys Leu
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 8
<223> OTHER INFORMATION: Xaa = Any Amino Acid

<400> SEQUENCE: 63

Gln Arg Ala Ile Thr Ile Leu Xaa Thr Glu Lys Ser
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 8
<223> OTHER INFORMATION: Xaa = Any Amino Acid

<400> SEQUENCE: 64

Gln Arg Ala Arg Thr Ile Leu Xaa Phe Glu Lys Met
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 8
<223> OTHER INFORMATION: Xaa = Any Amino Acid

<400> SEQUENCE: 65

Gln Trp Ala Thr Thr Ile Leu Xaa Ile Glu Arg Ser
1               5                   10
```

```
<210> SEQ ID NO 66
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 8
<223> OTHER INFORMATION: Xaa = Any Amino Acid

<400> SEQUENCE: 66

Gln Lys Ala Ile Ser Val Leu Xaa Met Glu Asn Gly
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 8
<223> OTHER INFORMATION: Xaa = Any Amino Acid

<400> SEQUENCE: 67

Gln Val Val Ala Thr Thr Val Xaa Leu Glu Arg Lys Leu
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 8
<223> OTHER INFORMATION: Xaa = Any Amino Acid

<400> SEQUENCE: 68

Gln Ile Val Ala Thr Thr Val Xaa Leu Glu Arg Lys Leu
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 9
<223> OTHER INFORMATION: Xaa = Any Amino Acid

<400> SEQUENCE: 69

Gln Arg Ala Ile Thr Ile Leu Asp Xaa Glu Lys Ser
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 9
<223> OTHER INFORMATION: Xaa = Any Amino Acid
```

```
<400> SEQUENCE: 70

Gln Arg Ala Arg Thr Ile Leu Glu Xaa Glu Lys Met
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 9
<223> OTHER INFORMATION: Xaa = Any Amino Acid

<400> SEQUENCE: 71

Gln Trp Ala Thr Thr Ile Leu Asp Xaa Glu Arg Ser
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 9
<223> OTHER INFORMATION: Xaa = Any Amino Acid

<400> SEQUENCE: 72

Gln Lys Ala Ile Ser Val Leu Glu Xaa Glu Asn Gly
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 9
<223> OTHER INFORMATION: Xaa = Any Amino Acid

<400> SEQUENCE: 73

Gln Val Val Ala Thr Thr Val Met Xaa Glu Arg Lys Leu
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 9
<223> OTHER INFORMATION: Xaa = Any Amino Acid

<400> SEQUENCE: 74

Gln Ile Val Ala Thr Thr Val Met Xaa Glu Arg Lys Leu
1               5                   10

<210> SEQ ID NO 75
<211> LENGTH: 12
<212> TYPE: PRT
<213> ORGANISM: Artificial Sequence
<220> FEATURE:
```

```
<223> OTHER INFORMATION: Synthetic polypeptide
<220> FEATURE:
<221> NAME/KEY: VARIANT
<222> LOCATION: 10
<223> OTHER INFORMATION: Xaa = Any Amino Acid

<400> SEQUENCE: 75

Gln Arg Ala Ile Thr Ile Leu Asp Thr Xaa Lys Ser
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 10
<223> OTHER INFORMATION: Xaa = Any Amino Acid

<400> SEQUENCE: 76

Gln Arg Ala Arg Thr Ile Leu Glu Phe Xaa Lys Met
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 10
<223> OTHER INFORMATION: Xaa = Any Amino Acid

<400> SEQUENCE: 77

Gln Trp Ala Thr Thr Ile Leu Asp Ile Xaa Arg Ser
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 10
<223> OTHER INFORMATION: Xaa = Any Amino Acid

<400> SEQUENCE: 78

Gln Lys Ala Ile Ser Val Leu Glu Met Xaa Asn Gly
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 10
<223> OTHER INFORMATION: Xaa = Any Amino Acid

<400> SEQUENCE: 79

Gln Val Val Ala Thr Thr Val Met Leu Xaa Arg Lys Leu
1               5                   10
```

```
<210> SEQ ID NO 80
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 10
<223> OTHER INFORMATION: Xaa = Any Amino Acid

<400> SEQUENCE: 80

Gln Ile Val Ala Thr Thr Val Met Leu Xaa Arg Lys Leu
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 11
<223> OTHER INFORMATION: Xaa = Any Amino Acid

<400> SEQUENCE: 81

Gln Arg Ala Ile Thr Ile Leu Asp Thr Glu Xaa Ser
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 11
<223> OTHER INFORMATION: Xaa = Any Amino Acid

<400> SEQUENCE: 82

Gln Arg Ala Arg Thr Ile Leu Glu Phe Glu Xaa Met
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 11
<223> OTHER INFORMATION: Xaa = Any Amino Acid

<400> SEQUENCE: 83

Gln Trp Ala Thr Thr Ile Leu Asp Ile Glu Xaa Ser
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 11
<223> OTHER INFORMATION: Xaa = Any Amino Acid
```

```
<400> SEQUENCE: 84

Gln Lys Ala Ile Ser Val Leu Glu Met Glu Xaa Gly
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 11
<223> OTHER INFORMATION: Xaa = Any Amino Acid

<400> SEQUENCE: 85

Gln Val Val Ala Thr Thr Val Met Leu Glu Xaa Lys Leu
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 11
<223> OTHER INFORMATION: Xaa = Any Amino Acid

<400> SEQUENCE: 86

Gln Ile Val Ala Thr Thr Val Met Leu Glu Xaa Lys Leu
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 12
<223> OTHER INFORMATION: Xaa = Any Amino Acid

<400> SEQUENCE: 87

Gln Arg Ala Ile Thr Ile Leu Asp Thr Glu Lys Xaa
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 12
<223> OTHER INFORMATION: Xaa = Any Amino Acid

<400> SEQUENCE: 88

Gln Arg Ala Arg Thr Ile Leu Glu Phe Glu Lys Xaa
1               5                   10

<210> SEQ ID NO 89
<211> LENGTH: 12
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: VARIANT
<222> LOCATION: 12
<223> OTHER INFORMATION: Xaa = Any Amino Acid

<400> SEQUENCE: 89

Gln Trp Ala Thr Thr Ile Leu Asp Ile Glu Arg Xaa
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 12
<223> OTHER INFORMATION: Xaa = Any Amino Acid

<400> SEQUENCE: 90

Gln Lys Ala Ile Ser Val Leu Glu Met Glu Asn Xaa
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 12
<223> OTHER INFORMATION: Xaa = Any Amino Acid

<400> SEQUENCE: 91

Gln Val Val Ala Thr Thr Val Met Leu Glu Arg Xaa Leu
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 12
<223> OTHER INFORMATION: Xaa = Any Amino Acid

<400> SEQUENCE: 92

Gln Ile Val Ala Thr Thr Val Met Leu Glu Arg Xaa Leu
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 13
<223> OTHER INFORMATION: Xaa = Any Amino Acid

<400> SEQUENCE: 93

Gln Val Val Ala Thr Thr Val Met Leu Glu Arg Lys Xaa
1               5                   10
```

<210> SEQ ID NO 94
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: 13
<223> OTHER INFORMATION: Xaa = Any Amino Acid

<400> SEQUENCE: 94

Gln Ile Val Ala Thr Thr Val Met Leu Glu Arg Lys Xaa
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 95

Ala Ile Ile Ile Thr Ile Leu Asp Thr Glu Ile Ser
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 96

Tyr Gly Arg Lys Lys Arg Arg Gln Arg Arg Arg
1               5                   10

<210> SEQ ID NO 97
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 97

Arg Lys Lys Arg Arg Gln Arg Arg Arg
1               5

<210> SEQ ID NO 98
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 98

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 99
<211> LENGTH: 16
<212> TYPE: PRT

<213> ORGANISM: Artificial Sequence
<220> FEATURE:
<223> OTHER INFORMATION: Synthetic polypeptide

<400> SEQUENCE: 99

```
Arg Arg Trp Arg Arg Trp Trp Arg Arg Trp Trp Arg Arg Trp Arg Arg
1               5                   10                  15
```

<210> SEQ ID NO 100
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 100

```
Arg Arg Arg Arg Arg Arg Arg
1               5
```

<210> SEQ ID NO 101
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 101

```
Arg Pro Lys Lys Arg Lys Val Arg Arg Arg
1               5                   10
```

<210> SEQ ID NO 102
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 102

```
Lys Lys Lys Lys Lys Lys Lys Lys Gly Gly Cys
1               5                   10
```

<210> SEQ ID NO 103
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 103

```
Lys Trp Lys Lys Lys Trp Lys Lys Gly Cys Cys
1               5                   10
```

<210> SEQ ID NO 104
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 104

```
Arg Trp Arg Arg Arg Trp Arg Arg Gly Gly Cys
1               5                   10
```

<210> SEQ ID NO 105
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 105

Gly Ala Leu Phe Leu Gly Phe Leu Gly Ala Ala Gly Ser Thr Met
1               5                   10                  15

Gly Ala Trp Ser Gln Pro Lys Ser Lys Arg Lys Val
            20                  25

<210> SEQ ID NO 106
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 106

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 107
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 107

Lys Leu Ala Leu Lys Leu Ala Leu Lys Ala Leu Lys Ala Ala Leu Lys
1               5                   10                  15

Leu Ala

<210> SEQ ID NO 108
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 108

Leu Leu Ile Ile Leu Arg Arg Arg Ile Arg Lys Gln Ala His Ala His
1               5                   10                  15

Ser Lys

<210> SEQ ID NO 109
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 109

Arg Val Ile Arg Val Trp Phe Gln Asn Lys Arg Cys Lys Asp Lys Lys
1               5                   10                  15

<210> SEQ ID NO 110
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 110

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 111
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 111

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 112
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 112
ggccacagag gatctggaaa ag                                            22

<210> SEQ ID NO 113
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 113
caaccctgct ggttccctaa g                                             21

<210> SEQ ID NO 114
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 114
ctgacggcaa ggatgactac c                                             21

<210> SEQ ID NO 115
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 115
acctcaggga gaagctcagg                                               20

```
<210> SEQ ID NO 116
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 116

Ile Thr Ile Leu Asp Thr Glu Lys Ser
1               5
```

PEPTIDE MODULATORS OF SPECIFIC CALCINEURIN PROTEIN-PROTEIN INTERACTIONS

CROSS-REFERENCE

This application claims the benefit of U.S. Provisional Patent Application No. 62/306,244, filed Mar. 10, 2016, which application is incorporated herein by reference in its entirety.

GOVERNMENT RIGHTS

This invention was made with Government support under contract HL109212 awarded by the National Institutes of Health. The Government has certain rights in the invention.

INTRODUCTION

Clinical trials using remote conditioning or cyclosporine A are encouraging strategies to limit reperfusion injury during cardiac bypass surgery or percutaneous coronary intervention (PCI), yet have provided mixed results. However, the recently reported negative study for cyclosporine to limit reperfusion injury when given during PCI in the CIRCUS trial suggests further deciphering of the molecular mechanism for these treatment strategies is needed. Reperfusion injury attributes up to 50% of the myocardial infarct size when the heart undergoes ischemia-reperfusion.

The transient receptor potential vanilloid 1 (TRPV1) is a non-selective ion channel, which preferentially gates calcium from pain stimuli. Besides the traditional activation of TRPV1 by pain, TRPV1 recently can act as a general sensor for cellular insults including hypoxia. The TRPV1 receptor is present in the nervous system and cardiac C-fibers. The TRPV1 agonist capsaicin, which exclusively activates only TRPV1, opens the inner gate of the TRPV1 channel near a conserved region called the TRP box. Capsaicin passes the lipid membrane and binds intracellularly to a cytosolic domain of the TRPV1 receptor.

Compounds targeting TRPV1 have been developed via traditional ligand-receptor approach, however development of a TRPV1 antagonist has been unsuccessful. Small molecule TRPV1 antagonists such as AMG517 developed caused hyperthermia in human clinical trials.

SUMMARY

Aspects of the present disclosure provide an isolated peptidic agent that selectively modulates the interaction between calcineurin and a calcineurin-binding protein partner (e.g., a TRPV channel). Inhibition of the interaction between calcineurin and a TRPV channel (e.g., TRPV1) results in the maintaining of the TRPV channel in an inactive state. Peptidic agents are provided which find use in treatment methods for conditions such as reperfusion injury (e.g., from myocardial infarction, stroke, organ transplantation, percutaneous transluminal coronary angiography), cardiac hypertrophy, transplant rejection, pain, osteoporosis, endothelial dysfunction and itch. In some cases, peptidic agents may be used as an immunosuppressant.

Methods of modulating a TRPV channel in a cell are provided. Aspects of the subject methods include contacting a cell with a peptidic agent that modulates the interaction between calcineurin and a TRPV channel. Also provided are pharmaceutical compositions that comprise a peptidic agent that selectively modulates the interaction between calcineurin and a calcineurin-binding protein partner. Also provided are methods of treating a condition in a subject by selectively modulating the interaction between calcineurin and a calcineurin-binding TRPV channel. Also provided are screening methods to identify candidate agents that modulate calcineurin protein-protein interactions.

BRIEF DESCRIPTION OF THE FIGURES

The skilled artisan will understand that the drawings, described below, are for illustration purposes only. The drawings are not intended to limit the scope of the present teachings in any way.

FIG. 3, panels A-E, shows biochemical evidence that TRPV1 is present in cardiomyocytes.

FIG. 4, panels A-B, shows co-localization between TRPV1 and TOM20.

FIG. 5, panels A-D, shows that TRPV1 is present in the heart and the sequence of TRPV1 in rat neonatal primary cardiomyocytes (SEQ ID NO:1).

FIG. 9, panels A-C, shows the effect on cells of CPZ and CsA treatment.

FIG. 10, panels A-E, depicts the calcineurin A interaction site with TRPV1. The interaction site of calcineurin A with AKAP5 is shown (AKAP5 sequence, SEQ ID NO:2; TRPV1 sequence, SEQ ID NO:3). V1-cal sequence in FIG. 10, panel D comprises RAITILDTEKS (SEQ ID NO:4).

FIG. 12, panels A-C, shows the determination of peptide stability.

FIG. 19, panels A-D, depicts the rational design of exemplary peptidic agents. Panel A shows the start of the intracellular portion of TRPV1 (SEQ ID NO:6). Panel B shows the location of the peptide cargo, perpendicular to the inner pore forming unit of TRPV1. RAITILDTEKS refers to SEQ ID NO:4. Panel C depicts an alpha wheel representation. Panel D shows various peptide sequences of interest: P1, SEQ ID NO:4; P2, SEQ ID NO:7; P3, SEQ ID NO:8; P4, SEQ ID NO:9; P5, SEQ ID NO:10; P6, SEQ ID NO:11; P7, SEQ ID NO:12; P8, SEQ ID NO:13 and P9, SEQ ID NO:14.

FIG. 20, panels A-C, shows confocal images of transiently transfected F11 cells expressing wild type TRPV1 (TRPV1-WT), TRPV1-T704A, and TRPV1-T704E channels.

FIG. 21, panels A-B. Panel A shows the fluorescence activated cell sorter analysis of transiently transfected live F11 cells for cell surface expression of TRPV1-WT, TPV1-T704A, or TRPV1-T704E channels with a fluorescent conjugated antibody recognizing the TRPV1 channel surface expression. The relative fluorescent intensity of transiently transfected cells expressing TRPV1 channels at the cell surface (cell count or number of surface cells detected expressing TRPV1) versus the corresponding fluorescent intensity. Panel B shows the percent difference in the total number of cells detected at the cell surface expressing TRPV1.

FIG. 22, panels A-B, shows the results of a western blot depicting whole cell lysate obtained from un-transfected F11 cells and F11 cells transfected with TRPV1-WT, TRPV1-T704A, or TRPV1-T704E channel F11 cells expressing TRPV1-T704A channels display a greater amount of mature, glycosylated, protein than either F11 cells expressing for TRPV1-WT or TRPV1-T704E (panel B). F-actin was used as a loading control. Panel B shows the quantification of the percentage maturation (glycosylation) of TRPV1 channels from the blot in panel A.

DEFINITIONS

Figure 1:
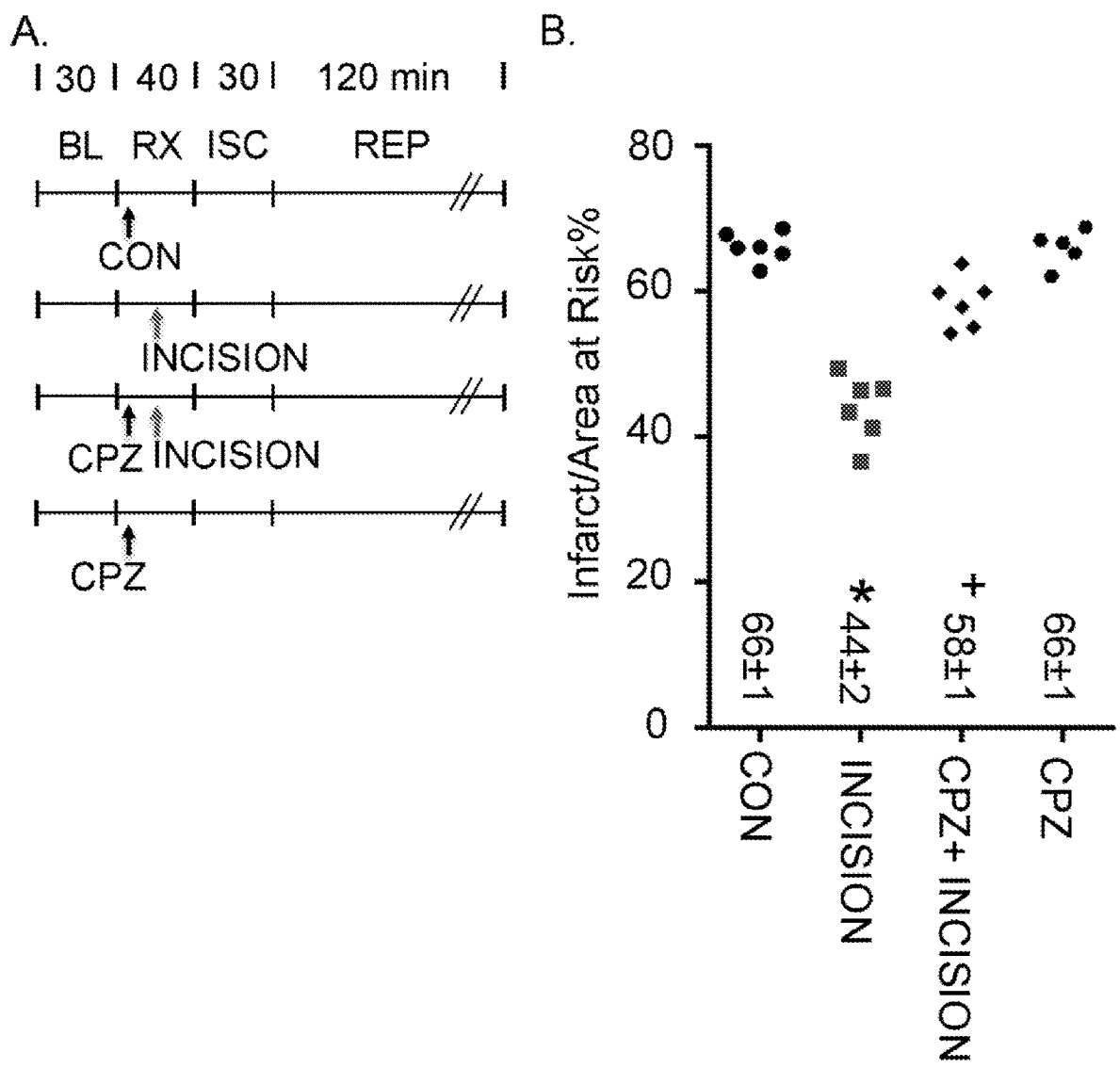
FIG. 1, panels A-B, shows that remote conditioning is mediated by TRPV1.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. As used herein, the term "peptidic" refers to a moiety that is composed of amino acid residues. The term "peptidic" includes compounds in which the conventional backbone has been replaced with non-naturally occurring or synthetic backbones, and peptides in which one or more naturally occurring amino acids have been replaced with one or more non-naturally occurring or synthetic amino acids, or a D-amino acid version thereof. Any of the depictions of sequences found herein (e.g., using one-letter or three-letter codes) may represent a L-amino acid or a D-amino acid version of the sequence. Unless noted otherwise, the capital and small letter codes for L- and D-amino acid residues, respectively, are not utilized.

The terms "polypeptide," "peptide," and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 50 amino acids. In some embodiments, peptides are between 5 and 30 amino acids in length.

The term "specific binding" refers to the ability of a capture agent to preferentially bind to a particular analyte that is present in a homogeneous mixture of different analytes. In some cases, a specific binding interaction will discriminate between desirable and undesirable analytes in a sample, typically more than about 10 to 100-fold or more (e.g., more than about 1000-fold). Typically, the affinity between a capture agent and analyte when they are specifically bound in a capture agent/analyte complex is at least $10^{-8}$ M, at least $10^{-9}$ M, usually up to about $10^{-10}$ M.

The term "assessing" any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent.

The term "isolated peptidic agent" means a peptidic agent which has been substantially separated from, or enriched relative to, other compounds with which it occurs in nature or during chemical synthesis. Any of the peptidic agents described herein may be isolated. Isolated peptidic agents are usually at least about 80% pure, or at least about 90% pure, at least about 98% pure, or at least about 99% pure, by weight. The present invention is meant to encompass diastereomers as well as their racemic and resolved, enantiomerically pure forms and pharmaceutically acceptable salts thereof.

"Reperfusion injury" refers to tissue damage caused when blood supply returns to the tissue after a period of ischemia. The absence of oxygen and nutrients from blood creates a condition in which the restoration of circulation results in inflammation and oxidative damage through the induction of oxidative stress rather than restoration of normal function It is known that restoration of blood flow following an ischemic episode can be equally if not more damaging than the ischemic episode, because reintroduction of oxygen results in an increased production of damaging free radicals that results in reperfusion injury. Necrosis can be greatly accelerated upon reperfusion, and therefore the compounds of the present invention may be delivered to an individual prior to, upon initiating restoration of blood flow, or during the restoration of blood flow to the body part.

"In combination with" as used herein refers to uses where, for example, the first compound (e.g., a peptidic agent) is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

As used herein, the term "sample" relates to a material or mixture of materials, in some cases in liquid form, containing one or more analytes of interest. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample". As used herein, the term "a biological sample" refers to a whole organism or a subset of its tissues, cells or component parts (e.g. body fluids, including, but not limited to, blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

A "variant" protein means a biologically active protein as defined below having less than 100% sequence identity with a native protein sequence. Such variants include proteins wherein one or more amino acid residues are added at the N- or C-terminus of, or within, the native sequence; from about one to forty amino acid residues are deleted, and optionally substituted by one or more amino acid residues; and derivatives of the above proteins, wherein an amino acid residue has been covalently modified so that the resulting product has a non-naturally occurring amino acid. Ordinarily, for example, a biologically active calcineurin variant will have an amino acid sequence having at least about 80% amino acid sequence identity with a native sequence of calcineurin, in some cases, at least about 90%, or in some cases at least about 95%.

"Treating" or "treatment" of a condition or disease includes: (1) preventing, ameliorating or altering at least one symptom of the conditions in a beneficial manner, i.e., causing a clinical symptom to not significantly develop in an animal (e.g., mammal) that may be exposed to or predisposed to the disease but does not yet experience or display symptoms of the disease, (2) inhibiting the disease, i.e., arresting or reducing the development of the disease and/or its symptoms, or (3) relieving the disease, i.e., causing regression or cure of the disease or its clinical symptoms. As used herein, amelioration of the symptoms of a particular disorder by administration of a particular compound or pharmaceutical composition refers to any lessening of disease symptoms and/or progression, whether permanent or temporary or lasting or transient, that is or can be attributed to or associated with the administration of the subject compound or composition.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The term "subject" means an animal (e.g., mammal) that may have a need for the pharmaceutical methods, compositions and treatments described herein. Subjects thus include, without limitation, primate (including humans), canine, feline, ungulate (e.g., equine, bovine, swine (e.g., pig)), and other subjects. Humans and non-human animals having commercial importance (e.g., livestock and domesticated animals) are of particular interest. "Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is preferably sterile, and free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

The term "organic group" and "organic radical" as used herein means any carbon-containing group, including hydrocarbon groups that are classified as an aliphatic group, cyclic group, aromatic group, functionalized derivatives thereof and/or various combinations thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, iso-propyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, trifloromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include fluoro, chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl)hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(iso-propyl)phenyl, 2, 3, or 4-ethylphenyl, 2, 3 or 4-(n-propyl)phenyl and the like; a mono or di(alkoxy)phenyl group, for example, 2,6-dimethoxyphenyl, 2, 3 or 4-(iso-propoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy) phenyl group such as 2, 3 or 4-carboxyphenyl or 2,4-di (protected carboxy)phenyl; a mono- or di(hydroxymethyl) phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl) phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl) ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynaphth-2-yl) methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl) alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Screen" or "screening", as well as the terms "selection" or "selecting", are used herein to refer to treatment of a population so as to facilitate separation of members in the population having a desired attribute (e.g., enzymatically 'switchable") from those that have a less desirable attribute (e.g., no detectable enzymatically switchable phenotype or an enzymatically switchable phenotype that is not of a desired dynamic range). A screen can be effected on a population of members using one or more criterion. Screening can be accomplished by means that maintain the recoverability and/or viability of the separated populations (e.g., by cell sorting using, e.g., FACS) or can be accomplished by reducing viability or recoverability of undesired members of the population.

A screen (or selection) can be a "positive screen" or a "negative screen" (also referred to herein as a "positive selection" or a "negative selection", respectively). In a "positive screen" members exhibiting a desirable attribute are selected according to the presence of a positive signal (e.g., the presence of a detectable signal, growth in the presence of an agent that inhibits growth of members deficient in a desirable attribute, etc.). In "negative screen" members exhibiting a desirable attribute are selected according to a decreased or undetectable signal (e.g., a relatively decreased or undetectable signal; reduced growth in the presence of an agent that inhibits growth of members exhibiting a desirable attribute, etc.)

As used herein, "contacting" has its normal meaning and refers to combining two or more entities (e.g., a peptidic agent, a candidate agent, a cell, etc.). Contacting can occur in, for example, a test tube or other container (e.g., combining of two or more agents, in a cell-based system (e.g., contacting of a peptidic agent with a suitable cell).

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, methods for modulating calcineurin protein-protein interactions are described first in greater detail. Next, methods of treatment and pharmaceutical compositions of interest for practicing the subject methods are reviewed. Screening methods are also described.

Methods for Modulating Calcineurin Protein-Protein Interactions

The present disclosure provides agents and methods of using the same for modulating the interaction of calcineurin with one or more of a family of TRPV ion channels. In some cases, the agents are peptidic (e.g., as described herein). The agents were designed to limit interactions with TRPV receptors in order to reverse pathological states without disturbing the natural physiological function of the TRPV receptors itself. The innovative approach described herein can be used to develop peptidic compounds that limit the interaction of calcineurin with a TRPV to, e.g., prevent or reverse a target pathological state. For example, the present disclosure demonstrates how limiting the interaction of calcineurin and TRPV1 using a peptide therapeutic can reduce cellular death after a heart attack. The subject agents provide therapeutics for a variety of indications e.g., myocardial reperfusion injury and additional cardiovascular diseases/states where limiting changes in mitochondrial membrane potential is beneficial.

The pain receptor channel, TRPV1, has a role in regulating remote conditioning. From this initial discovery, we elucidated that TRPV1 regulates mitochondrial membrane potential and is localized to the mitochondria. The present disclosure provides agents to modulate the interaction of calcineurin (a target of cyclosporine A) and TRPV family channels (e.g., TRPV1). In some cases, the subject agents find use in substantially limited reperfusion injury in both isolated heart and in vivo rodent models of myocardial ischemia-reperfusion injury, in some cases, one standard deviation more than remote conditioning or cyclosporine. The infarct size reduction observed with this peptide is one of the most efficacious we have achieved in the 10 years using the in vivo model of rat ischemia-reperfusion injury described herein.

The TRPV1 channel exists in an open, closed or inactive state. After TRPV1 activation and calcium influx, when TRPV1 is in an inactive state, it is re-activated by calcium-dependent interaction with calcineurin. The interaction of calcineurin is important for regulation of the TRPV1 channel state and the calcineurin-TRPV1 interaction is inducible upon activation of TRPV1. When activated a second time, the TRPV1 response is less; a phenomenon of desensitization.

Cyclosporine A (CsA) is an immunosuppressant drug whose therapeutic and toxic actions are mediated through inhibition of calcineurin (CN), a calcium- and calmodulin-dependent phosphatase. A target of cyclosporine A is the protein phosphatase 2B, calcineurin, which is important in regulating a number of cellular processes and pathophysiological states. Calcineurin is a heterodimer of a 61-kD calmodulin-binding catalytic subunit, calcineurin A and a 19-kD $Ca^{2+}$-binding regulatory subunit, calcineurin B. The calcineurin A subunit is known to interact with a family of six ion channels, the TRPV channels. The TRPV family of ion channels comprises six members: TRPV1, TRPV2, TRPV3, TRPV4, TRPV5 and TRPV6. Each member of the TRPV family can have a different physiological function.

Aspects of the present disclosure include methods of selectively modulating the activity of a calcineurin interacting protein partner in a cell. In some cases, the method comprises contacting the cell with an agent that selectively modulates the interaction between calcineurin and the interacting protein partner. In some embodiments, a method for selectively modulating the activity of a calcineurin interacting protein partner comprises selectively modulating the ability of calcineurin to interact with its protein partner, such as a member of the TRPV family of ion channels. In some cases, the method selectively and specifically inhibits the interaction between calcineurin and TRPV1. In some cases, the method selectively and specifically inhibits the interaction between calcineurin and TRPV2. In some cases, the method selectively and specifically inhibits the interaction between calcineurin and TRPV3. In some cases, the method selectively and specifically inhibits the interaction between calcineurin and TRPV4. In some cases, the method selectively and specifically inhibits the interaction between calcineurin and TRPV5. In some cases, the method selectively and specifically inhibits the interaction between calcineurin and TRPV6.

In some embodiments, a method for selectively modulating the ability of calcineurin to interact with a protein partner includes the use of an isolated peptidic agent that selectively modulates a calcineurin interacting protein partner. In some cases, the isolated peptidic agent selectively modulates the interaction between calcineurin and a TRPV channel. In some cases, the isolated peptidic agent selectively inhibits the interaction between calcineurin and a TRPV channel.

Aspects of the subject methods include contacting a sample with an agent. In certain cases, the sample comprises cells. Any convenient samples and cells may be contacted according to the subject methods. Any convenient method may be used to contact the sample with a subject agent that modulates the interaction between calcineurin and a TRPV channel A variety of cells may be targeted according to the subject methods. Cells of interest include any convenient cell which includes a TRPV channel.

In some instances, a method comprises contacting a cell with a peptidic agent that selectively modulates the interaction between calcineurin and a TRPV channel, leading to the inhibition of the interaction between calcineurin and a TRPV channel. In some cases, the method includes selectively inhibiting the interaction between calcineurin and a TRPV channel selected from TRPV1, TRPV2, TRPV3, TRPV4, TRPV5 and TRPV6. In some embodiments, selective inhibition of the interaction between calcineurin and TRPV1, TRPV2, TRPV3, TRPV4, TRPV5 or TRPV6, can lead to a 2-fold reduction or more in the interaction between calcineurin and the TRPV channel (e.g., a 3-fold or more reduction, a 4-fold or more reduction, a 5-fold or more reduction, a 6-fold or more reduction, a 7-fold or more reduction, a 8-fold or more reduction, a 9-fold or more reduction, a 10-fold or more reduction, a 15-fold or more reduction, a 20-fold or more reduction or more, etc.). A reduction in the interaction can be measured using any convenient method, including binding assays and functional assays.

In some instances, a method comprises contacting a cell with a peptidic agent that selectively modulates the interaction between calcineurin and a TRPV channel, leading to the enhancement of the interaction between calcineurin and a TRPV channel. In some cases, the method selectively enhances the interaction between calcineurin and TRPV1, TRPV2, TRPV3, TRPV4, TRPV5 or TRPV6. In some embodiments, selective enhancement of the interaction between calcineurin and TRPV1, TRPV2, TRPV3, TRPV4, TRPV5 or TRPV6, may lead to about a 10-fold enhancement in the interaction between calcineurin and the TRPV channel (e.g., about a 5-fold enhancement, about a 2-fold enhancement, about a 3-fold enhancement, about a 6-fold enhancement, about a 7-fold enhancement, about a 8-fold enhancement, about a 9-fold enhancement, at least a 10-fold enhancement, at least a 15-fold enhancement, at least a 20-fold enhancement or more, etc.).

The temperature at which selective modulation of the interaction between calcineurin and a TRPV channel takes place may vary, and in some instances may range from 5° C. to 50° C., such as from 10° C. to 40° C., 15° C. to 40° C., 20° C. to 40° C., e.g., 20° C., 25° C., 30° C., 35° C. or 37° C. (e.g., as described above). In some instances, the temperature at which selectively modulation takes place is selected to be compatible with the biological activity of the TRPV channel and/or the target cell. In certain instances, the temperature is 25° C., 30° C., 35° C. or 37° C.

Peptidic Agents

Aspects of the present disclosure provide a peptidic agent that selectively modulates the interaction between calcineurin and a TRPV channel A subject peptidic agent is isolated, and in many instances is purified, i.e., substantially pure. In some cases, a subject peptidic agent is synthetic, e.g., comprises a sequence of amino acids that is made in a laboratory by chemical synthesis methods or by recombinant methods. In some cases, a peptidic agent that selectively modulates the interaction between calcineurin and a TRPV channel results in the TRPV channel remaining in an inactive state Maintaining a TRPV channel in an inactive state may limit changes in mitochondrial membrane potential.

Peptidic agents of interest include any one of those described in FIG. 19, such as any one of P1 through P9 (FIG. 19, panel D). FIG. 19 describes the design of peptidic agents of interest that bind to the proposed structure of TRPV1.

In some cases, the peptidic agent comprises the following sequence: AIXIXDTEXS (SEQ ID NO:15), wherein X is any amino acid residue. In some instances, the peptidic agent comprises the following sequence: RAITILDTEKS (SEQ ID NO:4). In certain cases, the peptidic agent comprises 6 or more residues (e.g., 6, 7, 8, 9, 10 or 11 residues, or more) of RAITILDTEKS (SEQ ID NO:4). In certain cases, the peptidic agent comprises 6 or more residues (e.g., 6, 7, 8, 9, 10 or 11 residues, or more) of QRAITILDTEKSFLKCMRKAFR (SEQ ID NO:7). In certain cases, the peptidic agent comprises 6 or more residues (e.g., 6, 7, 8, 9, 10 or 11 residues, or more) of QRAITILDTEKS (SEQ ID NO:8). In certain cases, the peptidic agent comprises 6 or more residues (e.g., 6, 7, 8, 9, 10 or 11 residues, or more) of AITILDTEKSFLK (SEQ ID NO:9). In certain cases, the peptidic agent comprises 6 or more residues (e.g., 6, 7, 8, 9, 10 or 11 residues, or more) of ITILDTEKSFLKCMRKAFR (SEQ ID NO:10). In certain cases, the peptidic agent comprises 6 or more residues (e.g., 6, 7, 8, 9, 10 or 11 residues, or more) of ITILDTEKSFLKCMRK (SEQ ID NO:11). In certain cases, the peptidic agent comprises 6 or more residues (e.g., 6, 7, 8, 9, 10 or 11 residues, or more) of AITILDTEKSFLK (SEQ ID NO:12). In certain cases, the peptidic agent comprises 6 or more residues (e.g., 6, 7, 8, 9, 10 residues, or more) of ITILDTEKSF (SEQ ID NO:13). In certain cases, the peptidic agent comprises 6 or more residues (e.g., 6, 7, 8, 9, 10 or 11 residues, or more) of ITILDTEKSFLKCM (SEQ ID NO:14).

In certain cases, the peptidic agent comprises 6 or more residues (e.g., 6, 7, 8, 9, 10 or 11 residues, or more) of TRPV1(699-711). In certain cases, the peptidic agent comprises 6 or more residues (e.g., 6, 7, 8, 9, 10 or 11 residues, or more) of QRARTILEFEKM (SEQ ID NO:16). In certain cases, the peptidic agent comprises 6 or more residues (e.g., 6, 7, 8, 9, 10 or 11 residues, or more) of QWATTILDIERS (SEQ ID NO:17). In certain cases, the peptidic agent comprises 6 or more residues (e.g., 6, 7, 8, 9, 10 or 11 residues, or more) of QKAISVLEMENG (SEQ ID NO:18). In certain cases, the peptidic agent comprises 6 or more residues (e.g., 6, 7, 8, 9, 10 or 11 residues, or more) of QVVATTVMLERKL (SEQ ID NO:19). In certain cases, the peptidic agent comprises 6 or more residues (e.g., 6, 7, 8, 9, 10 or 11 residues, or more) of QIVATTVMLERKL (SEQ ID NO:20).

In certain cases, the peptidic agent comprises 6 or more residues (e.g., 6, 7, 8, 9, 10 or 11 residues, or more) of one of the following sequences:

```
                                              (SEQ ID NO: 21)
XRAITILDTEKS (SEQ ID NO: 22)
XRARTILEFEKM
```

```
                                    (SEQ ID NO: 23)
XWATTILDIERS (SEQ ID NO: 24)
XKAISVLEMENG.

(SEQ ID NO: 25)
XVVATTVMLERKL
or (SEQ ID NO: 26)
XIVATTVMLERKL,
``` wherein X is any amino acid residue.

In certain cases, the peptidic agent comprises 6 or more residues (e.g., 6, 7, 8, 9, 10 or 11 residues, or more) of one of the following sequences:

```
                                    (SEQ ID NO: 27)
QXAITILDTEKS (SEQ ID NO: 28)
QXARTILEFEKM (SEQ ID NO: 29)
QXATTILDIERS (SEQ ID NO: 30)
QXAISVLEMENG.

(SEQ ID NO: 31)
QXVATTVMLERKL
or (SEQ ID NO: 32)
QXVATTVMLERKL,
``` wherein X is any amino acid residue.

In certain cases, the peptidic agent comprises 6 or more residues (e.g., 6, 7, 8, 9, 10 or 11 residues, or more) of one of the following sequences:

```
                                    (SEQ ID NO: 33)
QRXITILDTEKS (SEQ ID NO: 34)
QRXRTILEFEKM (SEQ ID NO: 35)
QWXTTILDIERS (SEQ ID NO: 36)
QKXISVLEMENG.

(SEQ ID NO: 37)
QVXATTVMLERKL
or (SEQ ID NO: 38)
QIXATTVMLERKL,
``` wherein X is any amino acid residue.

In certain cases, the peptidic agent comprises 6 or more residues (e.g., 6, 7, 8, 9, 10 or 11 residues, or more) of one of the following sequences:

```
                                    (SEQ ID NO: 39)
QRAXTILDTEKS (SEQ ID NO: 40)
QRAXTILEFEKM (SEQ ID NO: 41)
QWAXTILDIERS (SEQ ID NO: 42)
QKAXSVLEMENG.

(SEQ ID NO: 43)
QVVXTTVMLERKL
or (SEQ ID NO: 44)
QIVXTTVMLERKL,
``` wherein X is any amino acid residue.

In certain cases, the peptidic agent comprises 6 or more residues (e.g., 6, 7, 8, 9, 10 or 11 residues, or more) of one of the following sequences:

```
                                    (SEQ ID NO: 45)
QRAIXILDTEKS (SEQ ID NO: 46)
QRARXILEFEKM (SEQ ID NO: 47)
QWATXILDIERS (SEQ ID NO: 48)
QKAIXVLEMENG.

(SEQ ID NO: 49)
QVVAXTVMLERKL
or (SEQ ID NO: 50)
QIVAXTVMLERKL,
``` wherein X is any amino acid residue.

In certain cases, the peptidic agent comprises 6 or more residues (e.g., 6, 7, 8, 9, 10 or 11 residues, or more) of one of the following sequences:

```
                                    (SEQ ID NO: 51)
QRAITXLDTEKS (SEQ ID NO: 52)
QRARTXLEFEKM (SEQ ID NO: 53)
QWATTXLDIERS (SEQ ID NO: 54)
QKAISXLEMENG.

(SEQ ID NO: 55)
QVVATXVMLERKL
or (SEQ ID NO: 56)
QIVATXVMLERKL,
``` wherein X is any amino acid residue.

In certain cases, the peptidic agent comprises 6 or more residues (e.g., 6, 7, 8, 9, 10 or 11 residues, or more) of one of the following sequences:

```
                                    (SEQ ID NO: 57)
QRAITIXDTEKS (SEQ ID NO: 58)
QRARTIXEFEKM (SEQ ID NO: 59)
QWATTIXDIERS
```

QKAISVXEMENG. (SEQ ID NO: 60)

QVVATTXMLERKL (SEQ ID NO: 61)
or
QIVATTXMLERKL, (SEQ ID NO: 62)

wherein X is any amino acid residue.

In certain cases, the peptidic agent comprises 6 or more residues (e.g., 6, 7, 8, 9, 10 or 11 residues, or more) of one of the following sequences:

QRAITILXTEKS (SEQ ID NO: 63)

QRARTILXFEKM (SEQ ID NO: 64)

QWATTILXIERS (SEQ ID NO: 65)

QKAISVLXMENG. (SEQ ID NO: 66)

QVVATTVXLERKL (SEQ ID NO: 67)
or
QIVATTVXLERKL, (SEQ ID NO: 68)

wherein X is any amino acid residue.

In certain cases, the peptidic agent comprises 6 or more residues (e.g., 6, 7, 8, 9, 10 or 11 residues, or more) of one of the following sequences:

QRAITILDXEKS (SEQ ID NO: 69)

QRARTILEXEKM (SEQ ID NO: 70)

QWATTILDXERS (SEQ ID NO: 71)

QKAISVLEXENG. (SEQ ID NO: 72)

QVVATTVMXERKL (SEQ ID NO: 73)
or
QIVATTVMXERKL, (SEQ ID NO: 74)

wherein X is any amino acid residue.

In certain cases, the peptidic agent comprises 6 or more residues (e.g., 6, 7, 8, 9, 10 or 11 residues, or more) of one of the following sequences:

QRAITILDTXKS (SEQ ID NO: 75)

QRARTILEFXKM (SEQ ID NO: 76)

QWATTILDIXRS (SEQ ID NO: 77)

QKAISVLEMXNG. (SEQ ID NO: 78)

QVVATTVMLXRKL (SEQ ID NO: 79)
or
QIVATTVMLXRKL, (SEQ ID NO: 80)

wherein X is any amino acid residue.

In certain cases, the peptidic agent comprises 6 or more residues (e.g., 6, 7, 8, 9, 10 or 11 residues, or more) of one of the following sequences:

QRAITILDTEXS (SEQ ID NO: 81)

QRARTILEFEXM (SEQ ID NO: 82)

QWATTILDIEXS (SEQ ID NO: 83)

QKAISVLEMEXG. (SEQ ID NO: 84)

QVVATTVMLEXKL (SEQ ID NO: 85)
or
QIVATTVMLEXKL, (SEQ ID NO: 86)

wherein X is any amino acid residue.

In certain cases, the peptidic agent comprises 6 or more residues (e.g., 6, 7, 8, 9, 10 or 11 residues, or more) of one of the following sequences:

QRAITILDTEKX (SEQ ID NO: 87)

QRARTILEFEKX (SEQ ID NO: 88)

QWATTILDIERX (SEQ ID NO: 89)

QKAISVLEMENX. (SEQ ID NO: 90)

QVVATTVMLERXL (SEQ ID NO: 91)
or
QIVATTVMLERXL, (SEQ ID NO: 92)

wherein X is any amino acid residue.

In certain cases, the peptidic agent comprises 6 or more residues (e.g., 6, 7, 8, 9, 10 or 11 residues, or more) of one of the following sequences:

QVVATTVMLERKX (SEQ ID NO: 93)
or
QIVATTVMLERKX, (SEQ ID NO: 94)

wherein X is any amino acid residue.

In some embodiments, a peptidic agent has sequence similarity to a carboxyl-terminal portion of the human A-kinase anchor protein 5 (AKAP5; also known as AKAP79 or AKAP150) that encompasses a calcineurin anchoring site (see, Li et al., *Nature Struc. & Mol. Biology*, 2012. 19:337-

345). In some cases, a peptidic agent can comprise an amino acid sequence having more than 50% sequence homology to the portion of AKAP5 that encompasses the calcineurin anchoring site. In some cases, the peptidic agent comprises an amino acid sequence having at least about 50% sequence homology to the amino acid sequence EPIAIIITDTEIS (SEQ ID NO:2). A peptidic agent can comprise an amino acid sequence having at least about 60%, at least about 70%, at least about 75%, at least about 80%, at least about 85%, at least about 90%, at least about 95%, at least about 97%, at least about 98%, at least about 99%, or 100% amino acid sequence identity to the amino acid sequence set forth in SEQ ID NO:2. In some cases, a peptidic agent may selectively modulate the interaction between calcineurin and AKAP5. A peptidic agent that selectively inhibits the interaction between calcineurin and AKAP5 can comprise an amino acid sequence having at least about 70%, at least about 75%, at least about 80%, at least about 85%, at least about 90%, at least about 95%, at least about 97%, at least about 98%, at least about 99%, or 100% amino acid sequence AIIITILDTEIS (SEQ ID NO:95).

In some cases, a peptidic agent of the present disclosure selectively modulates the interaction between calcineurin and a TRPV channel (e.g., TRPV1, TRPV2, TRPV3, TRPV4, TRPV5 or TRPV6). In some cases, a peptidic agent may selectively inhibit the interaction between calcineurin and TRPV1. A peptidic agent that selectively inhibits the interaction between calcineurin and TRPV1 can comprise an amino acid sequence having at least about 70%, at least about 75%, at least about 80%, at least about 85%, at least about 90%, at least about 95%, at least about 97%, at least about 98%, at least about 99%, or 100% amino acid sequence identity to the amino acid sequence QRAITILDTEKS (SEQ ID NO:8). In certain cases, a peptidic agent that selectively inhibits the interaction between calcineurin and TRPV1 can comprise an amino acid sequence having at least about 70%, at least about 75%, at least about 80%, at least about 85%, at least about 90%, at least about 95%, at least about 97%, at least about 98%, at least about 99%, or 100% amino acid sequence identity to the amino acid sequence QRAITILDTEKS (SEQ ID NO:8) and comprise a length of 12 or more residues (e.g., 12, 13, 14, 15, 16, 17, 18, 19, 20, 21, 22, 23, 24, 25, 26, 27, 28, 29, 30, 31, 32, 33 or 34 residues, or more). In some cases, a peptidic agent that selectively inhibits the interaction between calcineurin and TRPV1 may have at least 1 residue (e.g., 3, 4, 5, 6, 7, 8, 9, 10, at least 10 residues) that flanks each terminal of the amino acid sequence QRAITILDTEKS (SEQ ID NO:8).

In some cases, a peptidic agent may selectively inhibit the interaction between calcineurin and TRPV2. A peptidic agent that selectively inhibits the interaction between calcineurin and TRPV2 can comprise an amino acid sequence having at least about 70%, at least about 75%, at least about 80%, at least about 85%, at least about 90%, at least about 95%, at least about 97%, at least about 98%, at least about 99%, or 100% amino acid sequence QKAISVLEMENG (SEQ ID NO:18). In certain cases, a peptidic agent that selectively inhibits the interaction between calcineurin and TRPV2 can comprise an amino acid sequence having at least about 70%, at least about 75%, at least about 80%, at least about 85%, at least about 90%, at least about 95%, at least about 97%, at least about 98%, at least about 99%, or 100% amino acid sequence QKAISVLEMENG (SEQ ID NO:18) and comprise a length of 12 or more residues (e.g., 12, 13, 14, 15, 16, 17, 18, 19, 20, 21, 22, 23, 24, 25, 26, 27, 28, 29, 30, 31, 32, 33 or 34 residues, or more). In some cases, a peptidic agent that selectively inhibits the interaction between calcineurin and TRPV2 may have at least 1 residue (e.g., 3, 4, 5, 6, 7, 8, 9, 10, at least 10 residues) that flanks each terminal of the amino acid sequence QKAISVLEMENG (SEQ ID NO:18).

In some cases, a peptidic agent may selectively inhibit the interaction between calcineurin and TRPV3. A peptidic agent that selectively inhibits the interaction between calcineurin and TRPV3 can comprise an amino acid sequence having at least about 70%, at least about 75%, at least about 80%, at least about 85%, at least about 90%, at least about 95%, at least about 97%, at least about 98%, at least about 99%, or 100% amino acid sequence QRARTILEFEKM (SEQ ID NO:16). In certain cases, a peptidic agent that selectively inhibits the interaction between calcineurin and TRPV3 can comprise an amino acid sequence having at least about 70%, at least about 75%, at least about 80%, at least about 85%, at least about 90%, at least about 95%, at least about 97%, at least about 98%, at least about 99%, or 100% amino acid sequence QRARTILEFEKM (SEQ ID NO:16) and comprise a length of 12 or more residues (e.g., 12, 13, 14, 15, 16, 17, 18, 19, 20, 21, 22, 23, 24, 25, 26, 27, 28, 29, 30, 31, 32, 33 or 34 residues, or more). In some cases, a peptidic agent that selectively inhibits the interaction between calcineurin and TRPV3 may have at least 1 residue (e.g., 3, 4, 5, 6, 7, 8, 9, 10, at least 10 residues) that flanks each terminal of the amino acid sequence QRARTILEFEKM (SEQ ID NO:16).

In some cases, a peptidic agent may selectively inhibit the interaction between calcineurin and TRPV4. A peptidic agent that selectively inhibits the interaction between calcineurin and TRPV4 can comprise an amino acid sequence having at least about 70%, at least about 75%, at least about 80%, at least about 85%, at least about 90%, at least about 95%, at least about 97%, at least about 98%, at least about 99%, or 100% amino acid sequence QWATTILDIERS (SEQ ID NO:17). In certain cases, a peptidic agent that selectively inhibits the interaction between calcineurin and TRPV4 can comprise an amino acid sequence having at least about 70%, at least about 75%, at least about 80%, at least about 85%, at least about 90%, at least about 95%, at least about 97%, at least about 98%, at least about 99%, or 100% amino acid sequence QWATTILDIERS (SEQ ID NO:17) and comprise a length of 12 or more residues (e.g., 12, 13, 14, 15, 16, 17, 18, 19, 20, 21, 22, 23, 24, 25, 26, 27, 28, 29, 30, 31, 32, 33 or 34 residues, or more). In some cases, a peptidic agent that selectively inhibits the interaction between calcineurin and TRPV4 may have at least 1 residue (e.g., 3, 4, 5, 6, 7, 8, 9, 10, at least 10 residues) that flanks each terminal of the amino acid sequence QWATTILDIERS (SEQ ID NO:17).

In some cases, a peptidic agent may selectively inhibit the interaction between calcineurin and TRPV5. A peptidic agent that selectively inhibits the interaction between calcineurin and TRPV5 can comprise an amino acid sequence having at least about 70%, at least about 75%, at least about 80%, at least about 85%, at least about 90%, at least about 95%, at least about 97%, at least about 98%, at least about 99%, or 100% amino acid sequence QVVATTVMLERKL (SEQ ID NO:19). In certain cases, a peptidic agent that selectively inhibits the interaction between calcineurin and TRPV5 can comprise an amino acid sequence having at least about 70%, at least about 75%, at least about 80%, at least about 85%, at least about 90%, at least about 95%, at least about 97%, at least about 98%, at least about 99%, or 100% amino acid sequence QVVATTVMLERKL (SEQ ID NO:19) and comprise a length of 13 or more residues (e.g., 13, 14, 15, 16, 17, 18, 19, 20, 21, 22, 23, 24, 25, 26, 27, 28, 29, 30, 31, 32, 33 or 34 residues, or more). In some cases, a peptidic agent that selectively inhibits the interaction between calcineurin and TRPV5 may have at least 1 residue (e.g., 3, 4, 5, 6, 7, 8, 9, 10, at least 10 residues) that flanks each terminal of the amino acid sequence QVVATTVM-LERKL (SEQ ID NO:19).

In some cases, a peptidic agent may selectively inhibit the interaction between calcineurin and TRPV6. A peptidic agent that selectively inhibits the interaction between calcineurin and TRPV6 can comprise an amino acid sequence having at least about 70%, at least about 75%, at least about 80%, at least about 85%, at least about 90%, at least about 95%, at least about 97%, at least about 98%, at least about 99%, or 100% amino acid sequence QIVATTVMLERKL (SEQ ID NO:20). In certain cases, a peptidic agent that selectively inhibits the interaction between calcineurin and TRPV6 can comprise an amino acid sequence having at least about 70%, at least about 75%, at least about 80%, at least about 85%, at least about 90%, at least about 95%, at least about 97%, at least about 98%, at least about 99%, or 100% amino acid sequence QIVATTVMLERKL (SEQ ID NO:20) and comprise a length of 13 or more residues (e.g., 13, 14, 15, 16, 17, 18, 19, 20, 21, 22, 23, 24, 25, 26, 27, 28, 29, 30, 31, 32, 33 or 34 residues, or more). In some cases, a peptidic agent that selectively inhibits the interaction between calcineurin and TRPV6 may have at least 1 residue (e.g., 3, 4, 5, 6, 7, 8, 9, 10, at least 10 residues) that flanks each terminal of the amino acid sequence QIVATTVMLERKL (SEQ ID NO:20).

In certain instances of the subject peptidic agents (e.g., as described herein), the peptidic agent has a peptidic sequence having a length of 30 amino acid residues or less in total, such as 25 residues or less, 20 residues of less, 18 residues of less, 16 residues of less, 15 residues of less, 14 residues of less, 13 residues of less, or 12 residues of less. In certain cases, the peptidic agent has a sequence of at least 8 residues, such as at least 9 residues or at least 10 residues. In some cases, the peptide agent is an isolated peptidic agent.

The present disclosure provides methods for the identification of peptidic agents which may selectively modulate the interaction between calcineurin and other calcineurin interacting proteins. Such peptidic agents may result in the modulation of a variety of signaling pathways that regulate various physiological processes, see, Li et al., *Trends Cell Biol.*, 2012. 21(2):91-103. Examples of calcineurin substrates and binding partners of interest include those that are involved in transcriptional regulation, e.g., nuclear factor of activated T-cells (NFAT), transducer of regulated CREB protein 2 (TORC2; also known as CRTC2), ETS domain containing protein (Elk-1), retinoblastoma protein (Rb), myocyte enhancer factor 2A (MEF2A). Other examples include those that are receptors and ion channels, e.g., the vasopressin V1A receptor, TWIK-related spinal cord potassium channel (TRESK; also known as KCNK18), α-amino-3-hydroxy-5-methyl-4-isoxazolepropionic acid (AMPA) receptor, N-methyl-D-aspartate (NMDA) receptor, γ-aminobutyric acid (GABA) A receptor, GABA beta 2 subunit, inositol triphosphate receptor (IP3R), potassium voltage gated channel 2.1 (Kv2.1), ATP-sensitive potassium channel (KATP). Other examples include those that are scaffold and regulator proteins, e.g., protein kinase-A (PKA) RII subunit, Dopamine- and cyclic AMP-regulated phosphoprotein (DARPP-32; also known as PPP1R1B), Inhibitor-1, regulator of calcineurin (RCAN) family proteins, Cabin/Cain, kinase suppressor of Ras2 (KSR2), receptor for activated C kinase 1 (RACK1), calcium and integrin-binding protein 1 (CIB1). Membrane trafficking proteins such as Dephosphins are also examples of calcineurin substrates and binding partners. Cytoskeletal substrates and binding partners of calcineurin include, e.g., microtubule-associated protein 2 (MAP2), tubulin, Tau, Slingshot1L. Examples that are involved in the cell cycle and apoptosis include, e.g., Fizzy/Cdc20, Bcl-2-associated death promoter protein (BAD), dynamin-related protein 1 (Drp1). Other examples include, e.g., calcium-regulated heat-stable protein of 24 kDa (CRHSP-24), calcineurin-responsive zinc finger transcription factor 1 (Crz1), Hph1, Slm1 and Slm2, Calsarcin-1, -2, -3, muscle LIM protein (MLP).

In some cases, a peptidic agent comprises one or more modifications. For example, a peptidic agent can be cyclized. In certain cases, a peptidic agent can be a stapled or stitched peptide (e.g., comprises one or more synthetic braces). As another example, a peptidic agent can have one or more amino acid modifications. A peptidic agent may include one or more D-amino acids.

Modifications of interest that do not alter primary sequence include chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are peptides that have phosphorylated amino acid residues, e.g. phosphotyrosine, phosphoserine, or phosphothreonine. In some instances, a subject anti-microbial peptide comprises one or more phosphorylated amino acids. In some instances, a peptidic agent comprises one or more phosphotyrosine residues.

Aspects of the present disclosure provide peptidic agents that have been modified using ordinary molecular biological techniques and synthetic chemistry so as to improve their resistance to proteolytic degradation or to optimize solubility properties or to render them more suitable as a therapeutic agent. Analogs of such peptidic agents include those containing residues other than naturally occurring L-amino acids, e.g., D-amino acids or non-naturally occurring synthetic amino acids. For example, a modified peptidic agent can be a peptidic agent that comprises one or more (e.g., two or more, three or more, four or more, etc.) non-natural amino acid substitution(s).

The following are non-limiting examples of amino acid modifications that can be made to a peptidic agent:
a) substitution of alkyl-substituted hydrophobic amino acids: including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions; b) substitution of aromatic-substituted hydrophobic amino acids: including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine; c) substitution of amino acids containing basic side chains: including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid; d) substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids; e) substitution of side chain amide residues: including asparagine, glutamine, and alkyl or aromatic substituted derivatives of asparagine or glutamine; and f) substitution of hydroxyl containing amino acids: including serine, threonine, homoserine, 2,3-diaminopropionic acid, and alkyl or aromatic substituted derivatives of serine or threonine.

In some cases, a peptidic agent comprises one or more naturally occurring non-genetically encoded L-amino acids, synthetic L-amino acids or D-enantiomers of an amino acid. For example, a peptidic agent can comprise only D-amino acids. For example, a peptidic agent can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, Ω-aminohexanoic acid, Ω-aminoheptanoic acid, .omega.-aminooctanoic acid, .omega.-aminodecanoic acid, Ω-aminotetradecanoic acid, cyclohexylalanine, α,γ-diaminobutyric acid, α,β-diaminopropionic acid, δ-amino valeric acid, and 2,3-diaminobutyric acid.

In some cases, a peptidic agent includes one or more linkages other than peptide bonds, e.g., at least two adjacent amino acids are joined via a linkage other than an amide bond. For example, to reduce or eliminate undesired proteolysis or other degradation pathways and/or to increase serum stability and/or to restrict or increase conformational flexibility, one or more amide bonds within the backbone of a peptidic agent can be substituted.

For example, one or more amide linkages (—CO—NH—) in a peptidic agent can be replaced with another linkage which is an isostere such as: —$CH_2NH$—, $CH_2S$—, —$CH_2CH_2$—, —CH=CH-(cis and trans), —$COCH_2$—, —CH(OH)$CH_2$— and —$CH_2SO$—. This replacement can be made by methods known in the art.

As another example, one or more amide linkages in a peptidic agent can be replaced with a reduced isostere pseudopeptide bond. Couder et al. (1993) Int. J. Peptide Protein Res. 41:181-184.

The peptidic agent may be joined to a wide variety of other oligopeptides or proteins for a variety of purposes. By providing for expression of the subject peptides, various post-translational modifications may be achieved. For example, by employing the appropriate coding sequences, one may provide farnesylation or prenylation. In this situation, the peptide will be bound to a lipid group at a terminus, so as to be able to be bound to a lipid membrane, such as a liposome.

A cysteine residue or a cysteine analog can be introduced into a peptidic agent to provide for linkage to another peptide via a disulfide linkage or to provide for cyclization of a peptidic agent. Methods of introducing a cysteine or cysteine analog are known in the art; see, e.g., U.S. Pat. No. 8,067,532.

A peptidic agent can be cyclized. One or more cysteine or cysteine analogs can be introduced into a peptidic agent, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moiety) that can form a cyclizing bond can be used and/or introduced. A cyclizing bond can be generated with any combination of amino acids (or with amino acid and —$(CH_2)_n$—CO— or —$(CH_2)_n$—$C_6H_4$—CO—) with functional groups which allow for the introduction of a bridge. Some examples are disulfides, disulfide mimetics such as the —$(CH_2)_n$—carba bridge, thioacetal, thioether bridges (cystathionine or lanthionine) and bridges containing esters and ethers.

A peptidic agent may be a stapled or stitched peptide. By "stapled peptide", as used herein, is meant a peptide that comprises an intramolecular linkage used to enhance certain pharmacologic characteristics of the peptide. A "stitched peptide" refers to any peptides that comprise multiple or multiple tandem intramolecular linkages. Generally, a peptide is stapled by attachment of linkers through the amino acid side chains of two key residues within the peptide. Once synthesized, the linkers are connected, e.g., through a catalyst or any convenient coupling reagents or methods, thereby creating a bridge that physically constrains the peptide into its native c'-helical shape. In addition to helping retain the native structure needed to interact with a target molecule, this conformation also provides stability against peptidases as well as cell-permeating properties. U.S. Pat. No. 7,192,713, describing this technology, is hereby incorporated by reference.

Other modifications include, for example, an N-alkyl (or aryl) substitution, or backbone crosslinking to construct lactams and other cyclic structures. Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides.

In some cases, one or more L-amino acids in a peptidic agent is replaced with a D-amino acid.

In some cases, a peptidic agent is a retroinverso analog. Sela and Zisman (1997) FASEB J. 11:449. Retro-inverso peptide analogs are isomers of linear peptides in which the direction of the amino acid sequence is reversed (retro) and the chirality, D- or L-, of one or more amino acids therein is inverted (inverso) e.g., using D-amino acids rather than L-amino acids. See, e.g., Jameson et al. (1994) Nature 368:744; and Brady et al. (1994) Nature 368:692.

The carboxyl group $COR_3$ of the amino acid at the C-terminal end of a peptidic agent can be present in a free form ($R_3$=OH) or in the form of a physiologically tolerated alkaline or alkaline earth salt such as e.g. a sodium, potassium or calcium salt. The carboxyl group can also be esterified with primary, secondary or tertiary alcohols such as e.g., methanol, branched or unbranched $C_1$-$C_6$-alkyl alcohols, e.g., ethyl alcohol or tert-butanol. The carboxyl group can also be amidated with primary or secondary amines such as ammonia, branched or unbranched $C_1$-$C_6$-alkylamines or $C_1$-$C_6$ di-alkylamines, e.g., methylamine or dimethylamine.

The amino group of the amino acid $NR_1R_2$ at the N-terminus of a peptidic agent can be present in a free form ($R_1$=H and $R_2$=H) or in the form of a physiologically tolerated salt such as e.g., a chloride or acetate. The amino group can also be acetylated with acids so that $R_1$=H and $R_2$=acetyl, trifluoroacetyl, or adamantyl. The amino group can be present in a form protected by conventional amino protecting groups of peptide chemistry such as e.g., Fmoc, Z, Boc, or Alloc. The amino group can be N-alkylated in which $R_1$ and/or $R_2$=$C_1$—$C_6$ alkyl or $C_{-2}$—$C_8$ alkenyl or $C_7$—$C_9$ aralkyl.

Alkyl residues can be straight-chained, branched or optionally cyclic alkyl residues, e.g., methyl, ethyl, isopropyl and cyclohexyl.

One way to modify a peptidic agent is to conjugate (e.g. link) one or more additional elements at the N- and/or C-terminus of the peptide, such as another protein (e.g. having an amino acid sequence heterologous to the subject peptide) and/or a carrier molecule. Thus, an exemplary protein can be provided as fusion proteins with a polypeptide(s) derived from a peptidic agent.

Modifications that can enhance serum half-life of a peptidic agent are of interest. A peptidic agent may be "PEGylated", as containing one or more poly(ethylene glycol) (PEG) moieties. Methods and reagents suitable for PEGylation of a protein are well known in the art and may be found in U.S. Pat. No. 5,849,860, disclosure of which is incorporated herein by reference. PEG suitable for conjugation to a protein is generally soluble in water at room temperature, and has the general formula R(O—$CH_2$—$CH_2$)$_n$O—R, where R is hydrogen or a protective group such as an alkyl or an alkanol group, and where n is an integer from 1 to 1000. Where R is a protective group, it generally has from 1 to 8 carbons.

The PEG conjugated to the subject protein can be linear. The PEG conjugated to the subject protein may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

Where a peptidic agent is to be incorporated into a liposome, carbohydrate, lipid moiety, including N-fatty acyl groups such as N-lauroyl, N-oleoyl, fatty amines such as dodecyl amine, oleoyl amine, and the like (e.g., see U.S. Pat. No. 6,638,513) may also be used to modify the peptidic agent.

In some embodiments, a peptidic agent of the present disclosure may comprise a cell-penetrating peptide (e.g., transactivator of transcription (TAT) peptide) for intracellular delivery. Suitable cell penetrating peptides include those discussed in U.S. Patent Publication No. 2007/0129305. The cell penetrating peptides can be based on known peptides, including, but not limited to, penetratins; transportans; membrane signal peptides; viral proteins (e.g., TAT protein, VP22 protein, etc.); and translocating cationic peptides. TAT peptides comprising the sequence YGRKKRRQRRR (SEQ ID NO:96) are sufficient for protein translocating activity. $TAT_{47-57}$ peptides comprising the sequence YGRKKRRQRRR (SEQ ID NO:96). Additionally, branched structures containing multiples copies of TAT sequence RKKRRQRRR (SEQ ID NO:97; Tung, C. H. et al., Bioorg. Med. Chem 10:3609-3614 (2002)) can translocate efficiently across a cell membrane. Variants of TAT peptides capable of acting as a cell penetrating agent are described in Schwarze, S. R. et al., Science 285:1569-1572 (1999). A composition containing the C-terminal amino acids 159-301 of HSV VP22 protein is capable of translocating different types of cargoes into cells. Translocating activity is observed with a minimal sequence of DAATATR-GRSAASRPTERPRAPARSASRPRRPVE (SEQ ID NO:98). Active peptides with arginine rich sequences are present in the Grb2 binding protein, having the sequence RRWRRWWRRWWRRWRR (SEQ ID NO:99; Williams, E. J. et al., J. Biol. Chem. 272:22349-22354 (1997)) and polyarginine heptapeptide RRRRRRR (SEQ ID NO:100; Chen, L. et al., Chem. Biol. 8:1123-1129 (2001); Futaki, S. et al., J. Biol. Chem. 276:5836-5840 (2001); and Rothbard, J. B. et al., Nat. Med. 6(11):1253-7 (2000)). An exemplary cell penetrating peptide has the sequence RPKKRKVRRR (SEQ ID NO:101), which is found to penetrate the membranes of a variety of cell types. Also useful are branched cationic peptides capable of translocation across membranes, e.g., (KKKK)$_2$GGC (SEQ ID NO:102), (KWKK)$_2$GCC (SEQ ID NO:103), and (RWRR)$_2$GGC (SEQ ID NO:104) (Plank, C. et al., Human Gene Ther. 10:319-332 (1999)). A cell penetrating peptide can comprise chimeric sequences of cell penetrating peptides that are capable of translocating across cell membrane. An exemplary molecule of this type is transportan GALFLGFLG-GAAGSTMGAWSQPKSKRKV (SEQ ID NO:105), a chimeric peptide derived from the first twelve amino acids of galanin and a 14 amino acid sequence from mastoporan (Pooga, M et al., Nature Biotechnol. 16:857-861 (1998). Other types of cell penetrating peptides are the VT5 sequences DPKGDPKGVTVTVTVTVTGKGDPKPD (SEQ ID NO:106), which is an amphipathic, beta-sheet forming peptide (Oehlke, J., FEBS Lett. 415(2):196-9 (1997); unstructured peptides described in Oehlke J., Biochim Biophys Acta. 1330(1):50-60 (1997); alpha helical amphipathic peptide with the sequence KLALKLALKAL-KAALKLA (SEQ ID NO:107; Oehlke, J. et al., Biochim Biophys Acta. 1414(1-2):127-39 (1998); sequences based on murine cell adhesion molecule vascular endothelial cadherin, amino acids 615-632 LLIILRRRIRKQAHAHSK (SEQ ID NO:108; Elmquist, A. et al., Exp Cell Res. 269 (2):237-44 (2001); sequences based on third helix of the islet 1 gene enhancer protein RVIRVWFQNKRCKDKK (SEQ ID NO:109; Kilk, K. et al., Bioconjug. Chem. 12(6):911-6 (2001)); amphipathic peptide carrier Pep-1 KETWWETWWTEWSQPKKKRKV (SEQ ID NO:110; Morris, M. C. et al., Nat. Biotechnol. 19(12):1173-6 (2001)); and the amino terminal sequence of mouse prion protein MANLGYWLLALFVTMWTDVGLCKKRPKP (SEQ ID NO:111; Lundberg, P. et al., Biochem. Biophys. Res. Commun. 299(1):85-90 (2002).

Peptidic agents of the present disclosure may also comprise a spacer group. The spacer can provide for the linking of a cargo moiety to the agent. A wide variety of spacers are known in the art, and include by way of example and not limitation, alkyl, heteroalkyl, acyclic heteroatomic bridges, aryl, arylaryl, arylalkyl, heteroaryl, heteroarylalkyl, alcohols, amines and the like. Thus, spacers may include, for example, single, double, triple or aromatic carbon-carbon bonds, nitrogen-nitrogen bonds, carbon-nitrogen bonds, carbon-oxygen bonds and/or carbon-sulfur bonds, and may therefore include functionalities such as carbonyls, ethers, thioethers, carboxamides, sulfonamides, ureas, urethanes, hydrazines, etc. In one embodiment, the spacers can be alcohols or amines, which can quench the quinone methide. Examples of suitable spacers include, but are not limited to, aryl, biaryl, heteroaryl, etc. Cargo moieties of interest include, but are not limited to, cell permeable peptides (e.g., a TAT peptide), a detectable label (e.g., a dye), and the like.

Methods of Treatment

Aspects of the present disclosure provide a method of treating reperfusion injury in a subject, the method comprising administering to the subject an effective amount of a peptidic agent. Treatment methods of the present disclosure provide non-narcotic pain therapeutics (e.g., for pain relief). Treatment methods also provide means to reduce cellular injury (from, e.g. ischemia-reperfusion injury such as during, but not limited to myocardial infarction, stroke, organ transplants), treat cardiac hypertrophy, reduce transplant rejection, and treat osteoporosis. Treatment methods also provide means to reduce injury from percutaneous transluminal coronary angiography, to reduce itch, and to reverse endothelial dysfunction. Treatment methods may comprise the use of a peptidic agent as an immunosuppressant.

For in vivo protocols, any convenient administration protocol may be employed. Depending upon the binding affinity of the agent, the response desired, the manner of administration, the half-life, the number of cells present, various protocols may be employed. The number of administrations will depend upon the factors described above. The precise dose and particular method of administration will vary and may be readily determined by the attending physician or human or animal healthcare provider, e.g., the dose and method may be determined empirically. The particular dosage of the agent for any application may be determined in accordance with the procedures used for therapeutic dosage monitoring.

Peptidic agents described herein can be selected for use in methods of treatment of suitable subjects. The peptidic agents can be administered by any suitable means, including parenteral, subcutaneous, intraperitoneal, intravenous, intramuscular, subdermal, transdermal, intrathecal, intracranial, intrapulmonary, intranasal, and, if desired for local injection (e.g., at the site of reperfusion). In some cases, the agent may be administered parenterally, topically, or orally. Conventional and pharmaceutically acceptable routes of administration include intranasal, intramuscular, intratracheal, intracranial, subcutaneous, intradermal, topical application, intravenous, rectal, nasal, oral and other enteral and parenteral routes of administration. Routes of administration may be combined, if desired, or adjusted depending upon the agent and/or the desired effect. The composition can be administered in a single dose or in multiple doses. In some embodiments, the composition is administered orally. In other cases, the composition is administered intravenously. In other cases, the composition is administered via an inhalational route. In other cases, the composition is administered intramuscularly.

Parenteral administration routes include intramuscular, intravenous, intraarterial, intraperitoneal, or subcutaneous administration. Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Peptidic agents do not have to be given directly to a cellular target to reduce injury, and may, e.g. be given on the skin to provide protection from ischemic injury. Peptidic agents of the present disclosure can also be administered via a topic application (e.g., topical cream, ointment, patch), as a mouth wash (e.g., swish and swallow, swish and spit) as an acute intervention of prophylactic agent for those with cardiac risk factors.

The embodiments include compositions comprising a container suitable for containing a composition of the present disclosure for administration to an individual. For example, a subject composition can be disposed within a container suitable for containing a pharmaceutical composition. The container can be, for example, a bottle (e.g., with a closure device, such as a cap), a blister pack (e.g., which can provide for enclosure of one or more doses per blister), a vial, flexible packaging (e.g., sealed Mylar or plastic bags), an ampule (for single doses in solution), a dropper, a syringe, thin film, a tube and the like. In some cases, a container, such as a sterile container, comprises a subject pharmaceutical composition. In some embodiments the container is a bottle or a syringe. In some embodiments the container is a bottle. In some embodiments the container is a syringe.

The appropriate dosage of peptidic agent will depend on the type of disease to be treated, the severity and course of the disease, the patient's clinical history and response to the peptidic agent, and the discretion of the attending physician. Peptidic agents can suitably be administered to the patient at one time or over a series of treatments.

Depending on the type and severity of the disease, about 1 µg/kg to 15 mg/kg (e.g., 0.1-20 mg/kg) of the peptidic agent can serve as an initial candidate dosage for administration to the patient, whether, for example, by one or more separate administrations, or by continuous infusion. A typical daily dosage might range from about 1 µg/kg to 100 mg/kg or more, depending on factors such as those mentioned herein. For repeated administrations over several days or longer, depending on the condition, the treatment is sustained until a desired suppression of disease symptoms occurs. However, other dosage regimens may be useful.

As will be readily apparent to the ordinarily skilled artisan, the dosage is adjusted for a peptidic agent according to their potency and/or efficacy relative existing treatment options. A dose may be in the range of about 0.001 µg to 100 mg, given 1 to 20 times daily, and can be up to a total daily dose of about 0.01 µg to 100 mg. If applied topically, for the purpose of a systemic effect, the patch or cream would be designed to provide for systemic delivery of a dose in the range of about 0.01 µg to 100 mg. If injected for the purpose of a systemic effect, the matrix in which the peptidic agent of the present disclosure is administered is designed to provide for a systemic delivery of a dose in the range of about 0.001 µg to 1 mg. If injected for the purpose of a local effect, the matrix is designed to release locally an amount of peptidic agent of the present disclosure in the range of about 0.001 µg to 100 mg.

The peptidic agent composition will be formulated, dosed, and administered in a fashion consistent with good medical practice. Factors for consideration in this context include the particular disease being treated, the particular mammal being treated, the clinical condition of the individual patient, the cause of the disorder, the site of delivery of the peptidic agent, the method of administration, the scheduling of administration, and other factors known to medical practitioners. The "therapeutically effective amount" of an peptidic agent to be administered will be governed by such considerations, and is the minimum amount necessary to prevent, ameliorate, or treat a disease or disorder.

Generally, alleviation or treatment of a disease or disorder involves the lessening of one or more symptoms or medical problems associated with the disease or disorder. For example, in the case of reperfusion injury, the therapeutically effective amount of the peptidic agent can accomplish one or a combination of the following: reduce cellular injury from ischemia-reperfusion injury (such as during, but not limited to myocardial infarction, stroke, organ transplants); reduce the risk of transplant rejection; reduce the levels of osteoporosis; relieve pain when used alone or as an adjuvant to opiods; reduce the level of cardiac hypertrophy; reduce myocardial infarct size. In some cases, treatment may result in complete alleviation of any of the symptoms described herein. In some embodiments, a composition of the present disclosure can be used to prevent the onset or reoccurrence of the disease or disorder in a subject or mammal.

Peptidic agents can be used in combination (e.g., in the same formulation or in separate formulations) with one or more additional therapeutic agents or treatment methods ("combination therapy"). A peptidic agent can be administered in admixture with another therapeutic agent or can be administered in a separate formulation. Therapeutic agents and/or treatment methods that can be administered in combination with a peptidic agent of the present disclosure, and which are selected according to the condition to be treated, include surgery (e.g., surgical removal of ischemic tissue), myocardial infarction treatment, transplantation surgery treatment, cardiac arrest treatment, percutaneous coronary interventions, certain combinations of the foregoing, and the like. For example, peptidic agents of the present disclosure may be used in combination with a TRPV1 agonist, e.g., capsaicin. For example, peptidic agents of the present disclosure may be used in combination with a TRPV1 antagonist, e.g., capsazepine. For example, peptidic agents of the present disclosure may be used in combination with a calcineurin inhibitor, e.g., cyclosporine.

Kits with unit doses of a subject composition, e.g. in oral or topical doses, are provided. In such kits, in addition to the containers containing the unit doses will be an informational package insert describing the use and attendant benefits of the composition in treating pathological condition of interest. Preferred peptidic agents and unit doses are those described herein above.

A variety of subjects (wherein the term "subject" is used interchangeably herein with the terms "host" and "patient") are treatable according to the methods of the present disclosure. Generally such subjects are "mammals" or "mammalian," where these terms are used broadly to describe organisms which are within the class mammalia, including the orders carnivore (e.g., dogs and cats), rodentia (e.g., mice, guinea pigs, and rats), non-human primates, and primates (e.g., humans, chimpanzees, and monkeys). In some cases, a suitable subject for treatment methods of the present disclosure is a human.

Subjects suitable for treatment with a subject method include individuals undergoing treatment for a cardiac condition, thus the condition increases the subject's risk for ischemia, developing a stroke, or hemorrhage. The treatment, for example, may comprise the use of thrombolytic agents to treat myocardial infarctions. Still further, the subject may be at risk of ischemia or developing a stroke because the subject suffers from atrial fibrillation or a clotting disorder, for example. Other subjects that are at risk for ischemia or developing a stroke include subjects that are at risk of developing pulmonary emboli, subjects undergoing surgery (e.g., vascular surgery or neurological surgery), or subjects undergoing treatments that increase their risk for developing a stroke, for example, the treatment may comprise cerebral/endovascular treatment, angiography or stent placement. In other embodiments, the subject may be undergoing treatment for vascular disease that could place the spinal cord at risk for ischemia, such as surgery requiring aortic cross-clamping, surgery for abdominal aortic aneurysm, etc. In some embodiments of the invention, the subject has a chronic condition, whereas in other embodiments of the invention, the subject does not have a chronic condition, such as a short-term condition.

In some embodiments of the method, the method further comprises assessing modulation of the interaction between calcineurin and a TRPV channel (e.g., TRPV1, TRPV2, TRPV3, TRPV4, TRPV5 or TRPV6) in the subject. In some cases, the assessing may be performed by obtaining a sample (e.g., a cell sample) from the subject and performing an in vitro assay (e.g., as described herein). Any convenient methods can be used to assess modulation of the interaction between calcineurin and a TRPV channel Pharmaceutical Compositions Pharmaceutical compositions are provided herein which contain therapeutically effective amounts of one or more agents (e.g., peptidic agents, as described herein) in a pharmaceutically acceptable carrier that are useful in the prevention, treatment, or amelioration of one or more of the symptoms of diseases or disorders of interest, such as conditions associated with reperfusion, myocardial infarction, stroke, organ transplants, cardiac hypertrophy, osteoporosis. Pharmaceutical carriers suitable for administration of the peptidic agents provided herein include any such carriers known to those skilled in the art to be suitable for the particular mode of administration.

In addition, the peptidic agents may be formulated as the sole pharmaceutically active ingredient in the composition or may be combined with other active ingredients.

The compositions contain one or more peptidic agents provided herein. The peptidic agents are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the peptidic agents described above are formulated into pharmaceutical compositions using techniques and procedures well known in the art (see, e.g., Ansel Introduction to Pharmaceutical Dosage Forms, Fourth Edition 1985, 126). In certain preferable embodiments, the peptidic agents are formulated into suitable pharmaceutical preparations for oral administration to a subject.

In the compositions, effective concentrations of one or more peptidic agents or pharmaceutically acceptable derivatives thereof are mixed with a suitable pharmaceutical carrier. The peptidic agents may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the peptidic agents in the compositions are effective for delivery of an amount, upon administration, that treats, prevents, or ameliorates one or more of the symptoms of diseases or disorders associated with reperfusion, myocardial infarction, stroke, organ transplants, cardiac hypertrophy, and osteoporosis, is implicated.

In certain embodiments, the compositions are formulated for single dosage administration. To formulate a composition, the weight fraction of the peptidic agent is dissolved, suspended, dispersed or otherwise mixed in a selected carrier at an effective concentration such that the treated condition is relieved, prevented, or one or more symptoms are ameliorated.

The active peptidic agent is included in the pharmaceutically acceptable carrier in an amount sufficient to exert a therapeutically useful effect in the absence of undesirable side effects on the patient treated. The therapeutically effective concentration may be determined empirically by testing the peptidic agents in in vitro and in vivo systems described and then extrapolated therefrom for dosages for humans.

The concentration of active peptidic agent in the pharmaceutical composition will depend on absorption, inactivation and excretion rates of the active peptidic agent, the physicochemical characteristics of the peptidic agent, the dosage schedule, and amount administered as well as other factors known to those of skill in the art. For example, the amount that is delivered is sufficient to ameliorate one or more of the symptoms of diseases or disorders associated with with reperfusion, myocardial infarction, stroke, organ transplants, cardiac hypertrophy, and osteoporosis, as described herein.

In one embodiment, a therapeutically effective dosage should produce a serum concentration of active ingredient of from about 0.1 ng/ml to about 50-100 µg/ml. The pharmaceutical compositions, in another embodiment, should provide a dosage of from about 0.001 mg to about 2000 mg of peptidic agent per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the peptidic agents exhibit insufficient solubility, methods for solubilizing peptidic agents may be used. Such methods are known to those of skill in this art, and include, but are not limited to, using surfactants, such as TWEEN, or dissolution in aqueous sodium bicarbonate. Derivatives of the peptidic agents may also be used in formulating effective pharmaceutical compositions.

Upon mixing or addition of the peptidic agent(s), the resulting mixture may be a solution, suspension, emulsion or the like. The form of the resulting mixture depends upon a number of factors, including the intended mode of administration and the solubility of the peptidic agent in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the peptidic agent or pharmaceutically acceptable derivatives thereof. The pharmaceutically therapeutically active peptidic agents and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active peptidic agent sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active peptidic agent as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Dosage forms or compositions containing active peptidic agent in the range of 0.005% to 100% with the balance made up from non-toxic carrier may be prepared. Methods for preparation of these compositions are known to those skilled in the art. For example, subject compositions may contain 0.001%-100% active peptidic agent, in one embodiment 0.1-95%, in another embodiment 75-85%.

Compositions for Oral Administration

Oral pharmaceutical dosage forms may be solid, gel or liquid. In certain embodiments, the solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration

In certain embodiments, the formulations are solid dosage forms, in one embodiment, capsules or tablets. The tablets, pills, capsules, troches and the like can contain one or more of the following ingredients, or peptidic agents of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of peptidic agents which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The peptidic agent, or pharmaceutically acceptable derivative thereof, could be provided in a composition that protects it from the acidic environment of the stomach. For example, the composition can be formulated in an enteric coating that maintains its integrity in the stomach and releases the active peptidic agent in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The peptidic agents can also be administered as a component of an elixir, suspension, syrup, wafer, sprinkle, chewing gum or the like. A syrup may contain, in addition to the active peptidic agents, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a peptidic agent or pharmaceutically acceptable derivative thereof as described herein. Higher concentrations, up to about 98% by weight of the active ingredient may be included.

In all embodiments, tablet and capsule formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of peptidic agents which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545, the disclosures of which are herein incorporated by reference. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active peptidic agent or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603, the disclosures of which are herein incorporated by reference. Briefly, such formulations include, but are not limited to, those containing a peptidic agent provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained is also contemplated herein. Briefly, a peptidic agent provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The peptidic agent diffuses through the outer polymeric membrane in a release rate controlling step. The percentage of active peptidic agent contained in such parenteral compositions is highly dependent on the specific nature thereof, as well as the activity of the peptidic agent and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include sodium chloride injection, Ringers injection, isotonic dextrose injection, sterile water injection, dextrose and lactated Ringers injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEENa 80). Sequestering or chelating agents of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active peptidic agent is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active peptidic agent is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active peptidic agent to the treated tissue(s).

The peptidic agent may be suspended in micronized or other suitable form or may be derivatized to produce a more soluble active product or to produce a prodrug. The form of the resulting mixture depends upon a number of factors, including the intended mode of administration and the solubility of the peptidic agent in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a peptidic agent provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the peptidic agent. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected peptidic agent. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The peptidic agents or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. Where compositions are formulated as aerosols for inhalation or administration to the respiratory tract, the particles of the formulation may have diameters of 50 microns or less, such as 40 microns or less, such as 30 microns or less, such as 25 microns or less, such as 15 microns or less, such as 10 microns or less, such as 5 microns or less and including having diameters of 1 micron or less.

The peptidic agents may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active peptidic agent alone or in combination with other pharmaceutically acceptable excipients can also be administered.

These solutions, such as for example for ophthalmic use, may be formulated as 0.01%-10% isotonic solutions, pH about 5-7, with appropriate salts.

Compositions for Other Routes of Administration

Other routes of administration, such as transdermal patches, including iontophoretic and electrophoretic devices, and buccal and rectal administration, are also contemplated herein.

Transdermal patches, including iotophoretic and electrophoretic devices of interest may include, but are not limited to those disclosed in U.S. Pat. Nos. 6,267,983, 6,261,595, 6,256,533, 6,167,301, 6,024,975, 6,010,715, 5,985,317, 5,983,134, 5,948,433, and 5,860,957, the disclosures of which are herein incorporated by reference.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Methods of Screening

Aspects of the present disclosure also include screening assays configured to identify agents that find use in methods of the present disclosure, e.g., as reviewed above. Aspects of the present disclosure provide screening methods to assess whether a test compound modulates the interaction between calcineurin and a calcineurin interacting protein partner. In some cases, a screening method of the present disclosure comprises a) contacting a cell with a candidate agent (e.g., a small molecule) and a peptidic agent that selectively modulates the interaction between calcineurin and a calcineurin interacting protein partner; b) detecting a cellular parameter, wherein a change in the parameter in the cell as compared to in a cell not contacted with the candidate agent indicates that the candidate agent modulates the interaction between calcineurin and a calcineurin interacting protein partner.

The candidate agent may be a small molecule, an oligonucloetide, an antibody and a polypeptide.

Drug screening may be performed using an in vitro model, a genetically altered cell or animal, or purified peptidic agent. One can identify ligands that compete with, modulate or mimic the action of a lead agent. Drug screening identifies agents that modulate the interaction between calcineurin and one of its protein binding partners. A wide variety of assays may be used for this purpose, including labeled in vitro binding assays, electrophoretic mobility shift assays, immunoassays for protein binding, and the like. Knowledge of the 3-dimensional structure of calcineurin, derived from the structural studies described herein, can also lead to the rational design of small drugs that specifically modulate the interaction between calcineurin and its protein binding partners.

A wide variety of assays may be used to assess the level of modulation of the interaction between calcineurin and a calcineurin binding protein partner. As an example, the following assays are described for when the calcineurin binding protein partner is a TRPV channel (e.g., TRPV1). As summarized above, the interaction of calcineurin is important for regulation of the TRPV1 channel state and the calcineurin-TRPV1 interaction is inducible upon activation of TRPV1. For example, a competitive in vitro calcineurin activity assay may be employed, comprising contacting a cell (e.g., of a cell culture model of ischemia-reoxygenation) with both a peptidic agent of the present disclosure and a candidate agent; detecting a cellular parameter, wherein a change in the parameter in the cell as compared to in a cell not contacted with the candidate agent indicates that the candidate agent modulates the interaction between calcineurin and a calcineurin interacting protein partner. In some cases, the parameter may be detected, e.g., by measuring mitochondrial membrane potential. In some cases, the parameter may be the level of dephosphorylation of a calcineurin substrate which can be measured by free phosphate release. In some embodiments, an in vitro assay may use isolated hearts (e.g., isolated heart model of ischemia-reperfusion injury).

In some embodiments, an in vivo screening method may be performed using an animal, e.g., a rat, a mouse and the like. In such embodiments, a screening method of the present disclosure comprises a) delivering into an animal, a candidate agent (e.g., a small molecule) and a peptidic agent that selectively modulates the interaction between calcineurin and a calcineurin interacting protein partner; b) detecting a parameter, wherein a change in the parameter in the animal as compared to an animal not contacted with the candidate agent indicates that the candidate agent modulates the interaction between calcineurin and a calcineurin interacting protein partner. In such embodiments, detecting a parameter involves detecting a measurable output, e.g., measuring the myocardial infarct size, measuring the area at risk/left ventricle percent, measuring hemodynamics (e.g., heart rate, blood pressure, rate pressure product, etc.), or combinations thereof.

A candidate agent of a screening method of the present disclosure may be an agonist of the calcineurin binding protein partner (e.g., the TRPV1 agonist, capsaicin). A candidate agent of a screening method of the present disclosure may be an antagonist of the calcineurin binding protein partner (e.g., the TRPV1 antagonist, capsazepine). A candidate agent of a screening method of the present disclosure may be a calcineurin inhibitor (e.g., cyclosporine).

In some cases, a screening method employs the use of a transgenic subject, wherein the subject stably expresses, e.g. a variant of calcineurin, a variant of a calcineurin interacting protein partner (e.g., mutant TRPV1). In some cases, the candidate agent and the peptidic agent can be administered at the same time. In some cases, a mixture comprising the candidate agent and the peptidic agent is administered. In some cases the candidate agent and the peptidic agent can be administered sequentially, i.e., the peptidic agent is administered a duration after the candidate agent is administered.

In some cases, the subject is a non-human subject. In some cases, the subject can be a variety of subjects that are capable of receiving reperfusion injury. Generally, such subjects are non-human. Generally, such subjects are "mammals" or "mammalian", where these terms are used broadly to describe organisms which are within the class mammalia, including the orders carnivore (e.g., dogs and cats), rodentia (e.g., mice, guinea pigs and rats), and primates (e.g., chimpanzees and monkeys). In some cases, non-mammalian subjects can be used (e.g., *Drosophila, C. elegans* and zebrafish).

In some cases, a class of candidate agent that is of interest is a candidate agent that reduces reperfusion injury (e.g., myocardial infarct size). Such a candidate agent may reduce the myocardial infarct size by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75% or more, compared to the myocardial infarct size of a subject in the absence of the candidate agent. Such a candidate agent may reduce the level of the parameter measured in the cell, or, e.g. in an isolated heart, of an in vitro screening method by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75% or more, compared to the level of the parameter in the absence of the candidate agent. In other instances, a class of candidate agent that is of interest is a candidate agent that increases reperfusion injury (e.g., myocardial infarct size). Such a candidate agent may increase the level of reperfusion by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75% or more, compared to the level of reperfusion injury experienced by the subject in the absence of the candidate agent. Such a candidate agent may increase the level of the quantifiable event in the cell of an in vitro screening method by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75% or more, compared to the level of the parameter in the absence of the candidate agent.

In some cases, the present disclosure provides candidate agents that can be further developed into therapeutic agents. For example, a candidate agent that reduces the level of reperfusion injury in a subject (e.g., by at least about 40%) can be further developed into a therapeutic agent for the treatment of reperfusion injury.

The terms "candidate agent," "test agent," "agent," "substance," and "test compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Screening may be directed to known pharmacologically active compounds and chemical analogs thereof, or to new agents with unknown properties such as those created through rational drug design.

Candidate agents may be small organic or inorganic compounds having a molecular weight of more than 50 and less than about 10,000 daltons, e.g., from about 50 daltons to about 100 daltons, from about 100 daltons to about 500 daltons, from about 500 daltons to about 1000 daltons, from about 1000 daltons to about 5000 daltons, or from about 5000 daltons to about 10,000 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Subject screening methods may include controls, where suitable controls include, e.g., a sample (e.g., a sample comprising the test subject) in the absence of the candidate agent. Generally, a plurality of assay mixtures is run in parallel with different candidate agent concentrations to obtain a differential response to the various concentrations. Typically, one of these concentrations serves as a negative control, i.e. at zero concentration or below the level of detection.

Candidate agents that have an effect in a subject screening method may be further tested for cytotoxicity, bioavailability, and the like, using well known assays. Candidate agents that have an effect in a subject assay method may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barrier.

A variety of other reagents may be included in the screening assay. These include reagents like salts, neutral proteins, e.g. albumin, detergents, etc., that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hour will be sufficient.

A candidate agent is assessed for any cytotoxic activity it may exhibit toward the subject used in a screening method of the present disclosure, using well-known assays, such as trypan blue dye exclusion, an MTT ([3-(4,5-dimethylthiazol-2-yl)-2,5-diphenyl-2 H-tetrazolium bromide]) assay, and the like. Test compounds that do not exhibit significant cytotoxic activity may be considered as candidate agents.

Any candidate agent identified can be further evaluated, for example, in a secondary screen to determine efficacy in other cell types, to determine cell type specific effects, and the like.

Utility

The subject agents and methods find use in a variety of applications, including therapeutic applications and research applications. The subject agents and methods find use in any application where modulation of the calcineurin interaction with a TRPV channel, or component thereof is of interest. In certain instances, the subject agents find use in any convenient application where cyclosporine is utilized. Cyclosporin can lead to a variety of undesirable side effects, which in some cases, can be minimized or avoided by utilizing the subject agents and methods. TRPV channel family members are involved in a variety of indications, including but not limited to, pain, ischemia-reperfusion, itch, psoriasis, regulation of pain, osmoregulation, immune function, cancer, osteoporosis, and regulation of calcium in bone. In some cases, the subject agents and methods find use in the treatment of an ischemia-reperfusion injury, such as heart attack or stroke, or during bypass surgery, or during reperfusion of transplanted tissue or organs, such as heart, kidney, liver or lung transplants. In certain instances, the subject agents and methods find use in the control of inflammatory pain.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Materials and Methods

Procedures and protocols were approved by the Animal Care and Use Committee at both Stanford University and Medical College of Wisconsin. Animal studies conformed to the National Institute of Health *Guide for the Care and Use of Laboratory Animals*. Eight to 10 week old male Sprague-Dawley rats (Charles River) and TRPV1 knockout rats (SAGE laboratories) were used for the studies outlined. The total number of animals used, number included and excluded for this study including from which groups were documented (TABLE 1).

TABLE 1

Sprague-Dawley rats used

Figure 2:
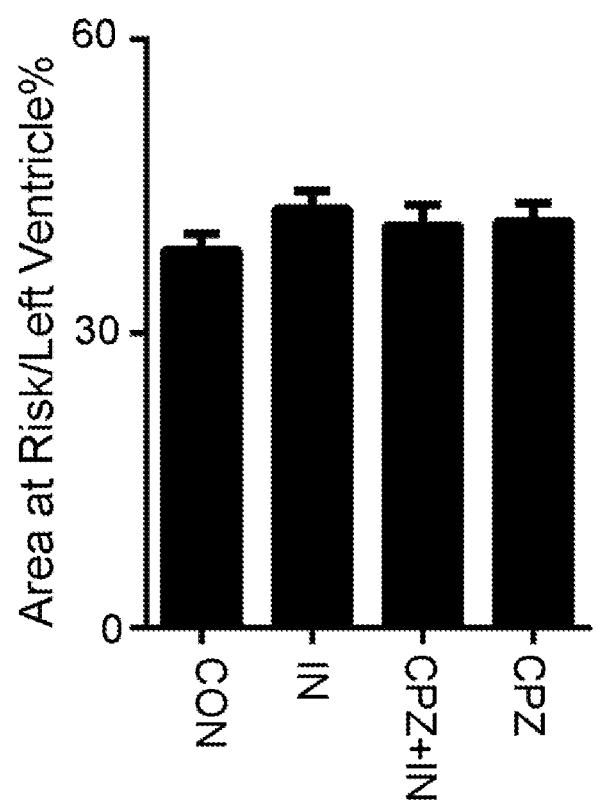
FIG. 2 shows the area at risk per left ventricle for each individual group.
Figure 6:
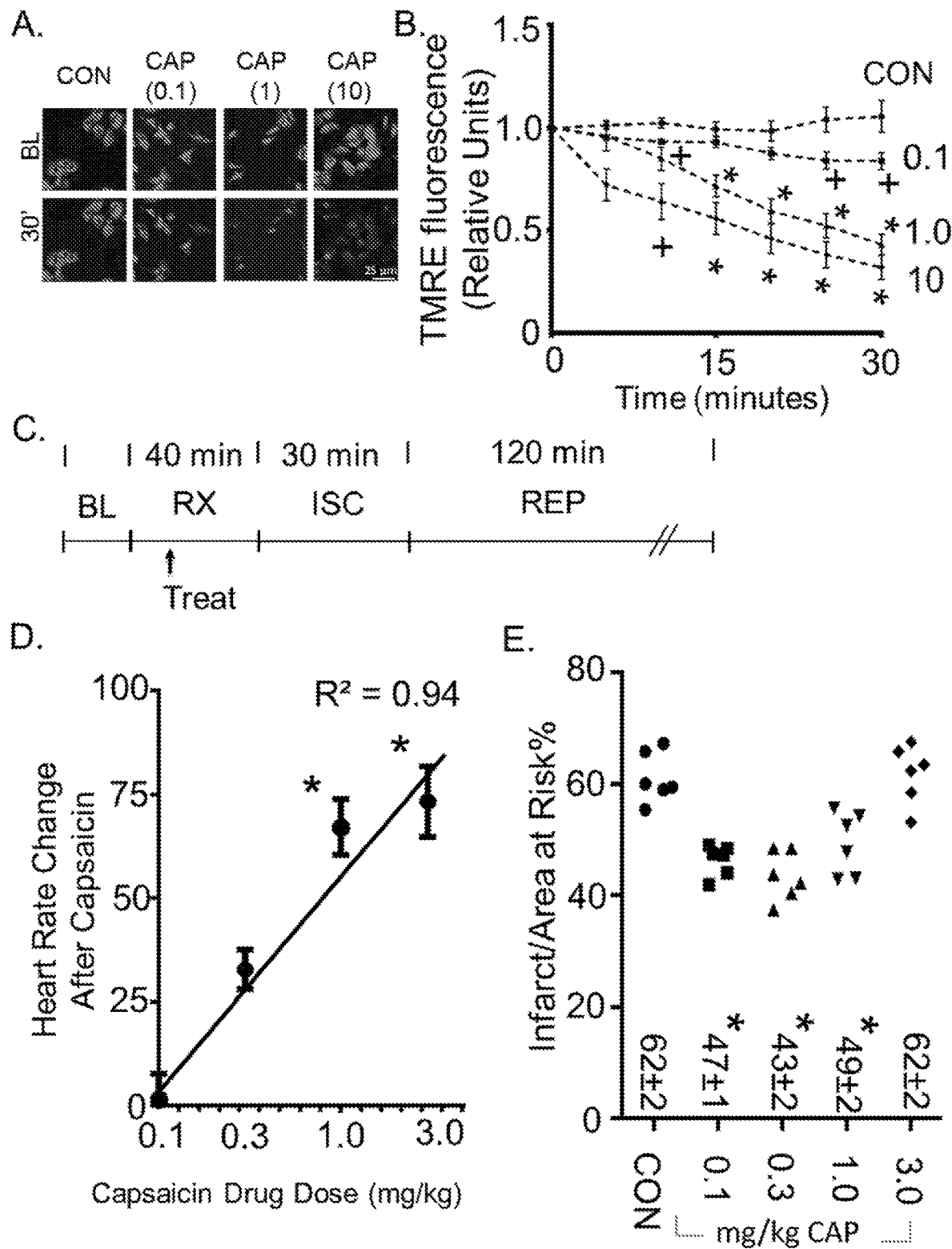
FIG. 6, panels A-E, shows that TRPV1 regulates mitochondrial membrane potential and infarct size.
Figure 7:
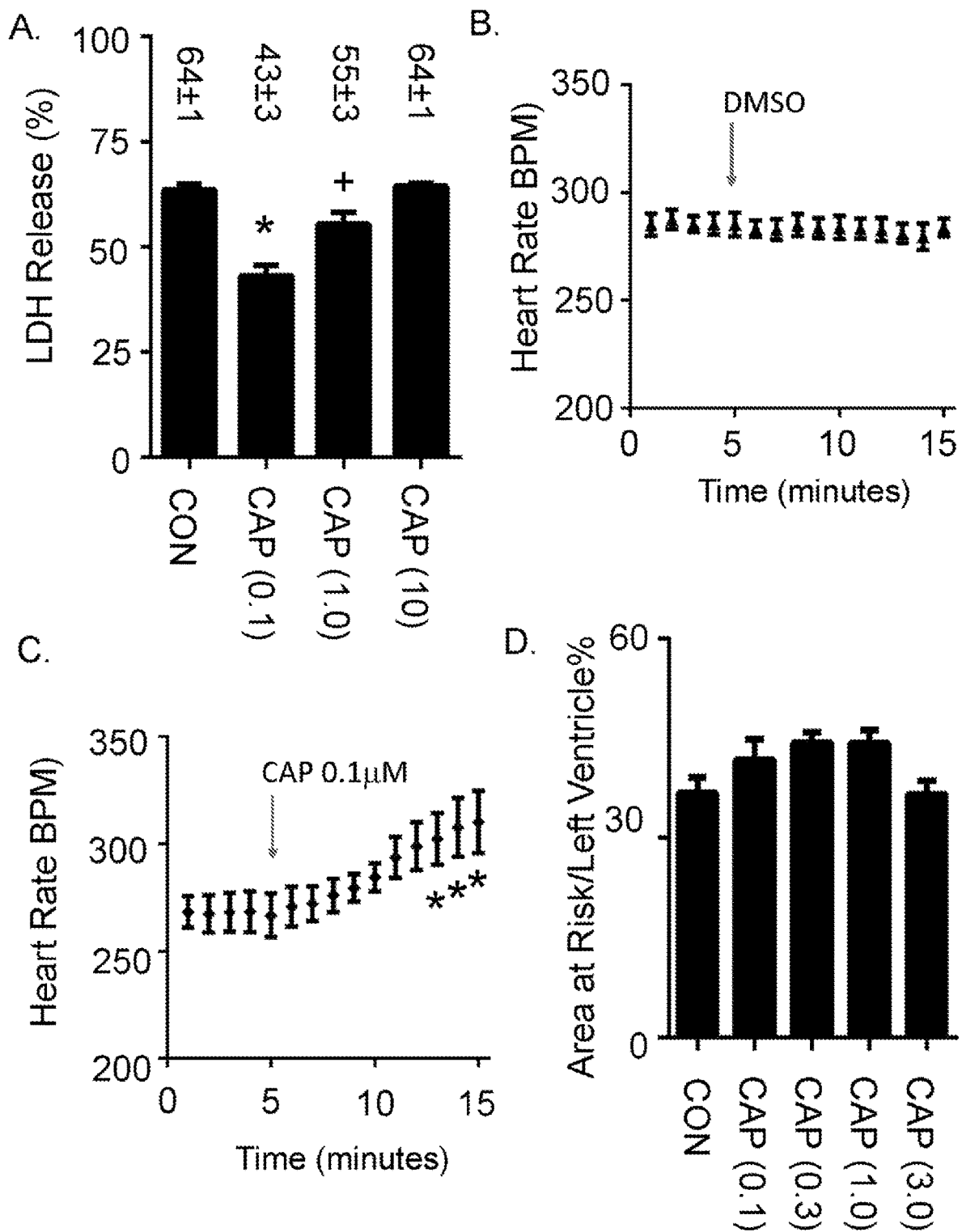
FIG. 7, panels A-D, shows results from ischemia-reoxygenation experiments.
Figure 8:
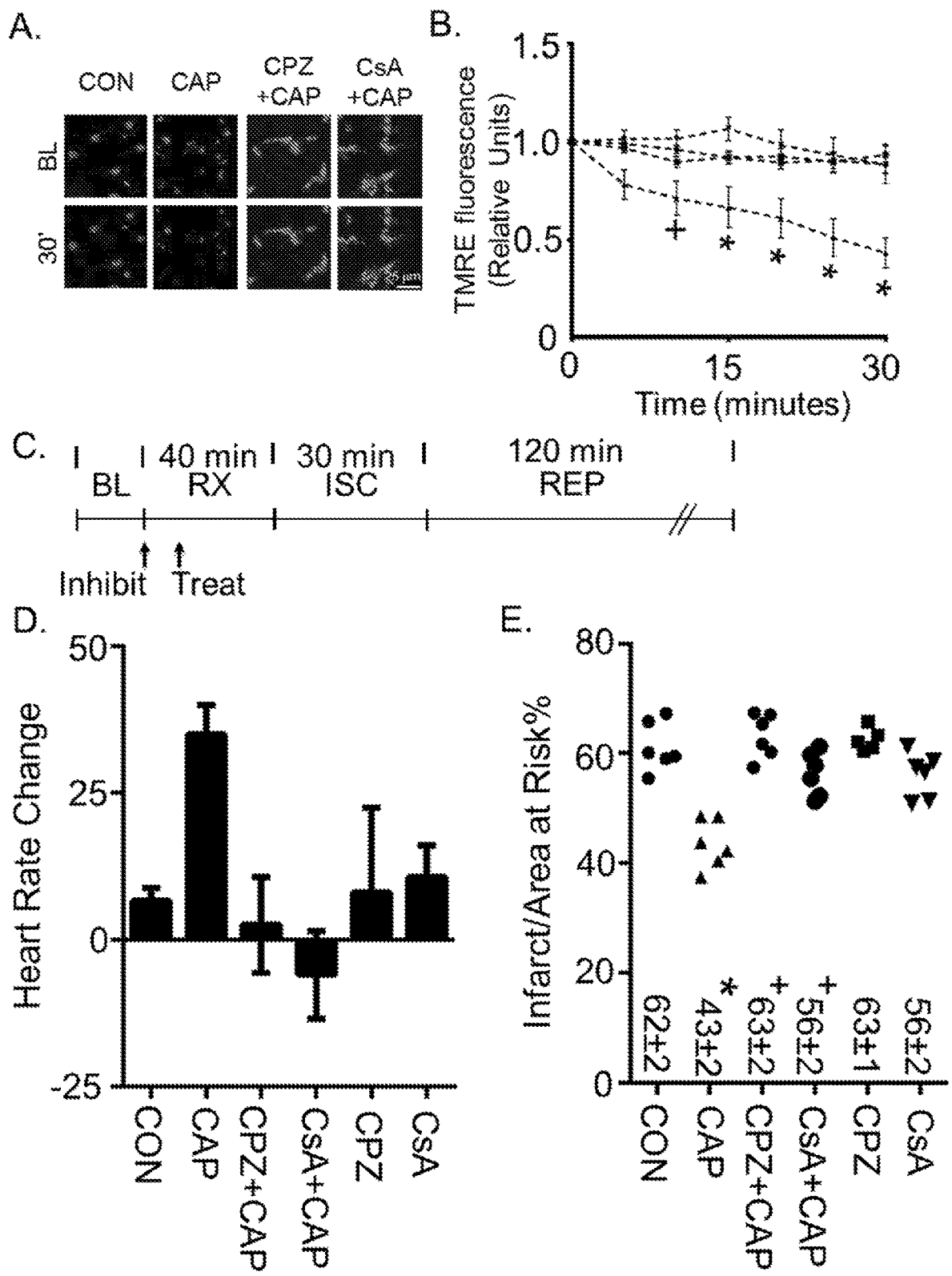
FIG. 8, panels A-E, shows that calcineurin inhibition regulates mitochondrial membrane potential and infarct size.
Figure 14:
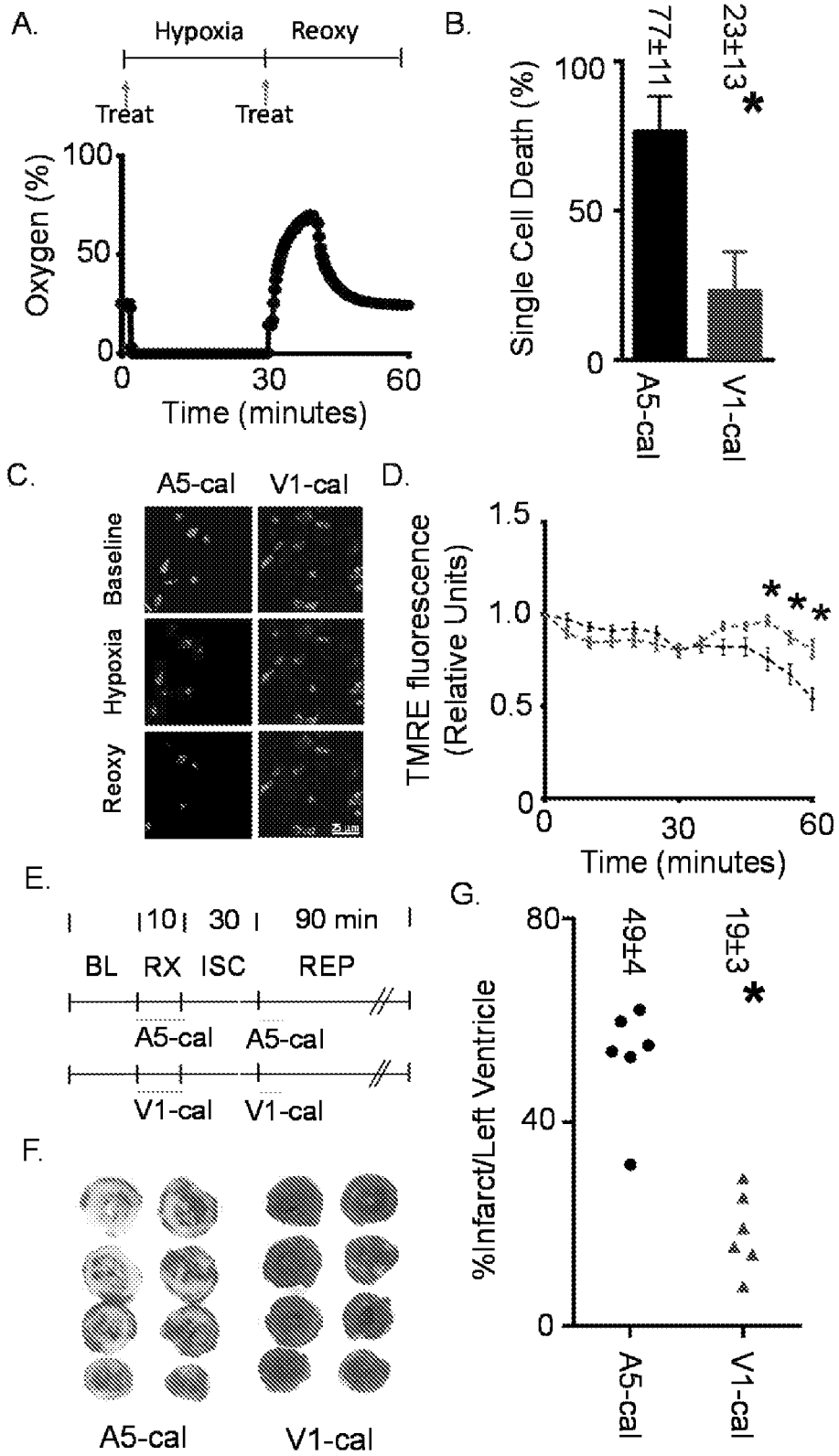
FIG. 14, panels A-G, shows the results of single cell hypoxia-reoxygenation and isolated heart myocardial infarction experiments.
Figure 15:
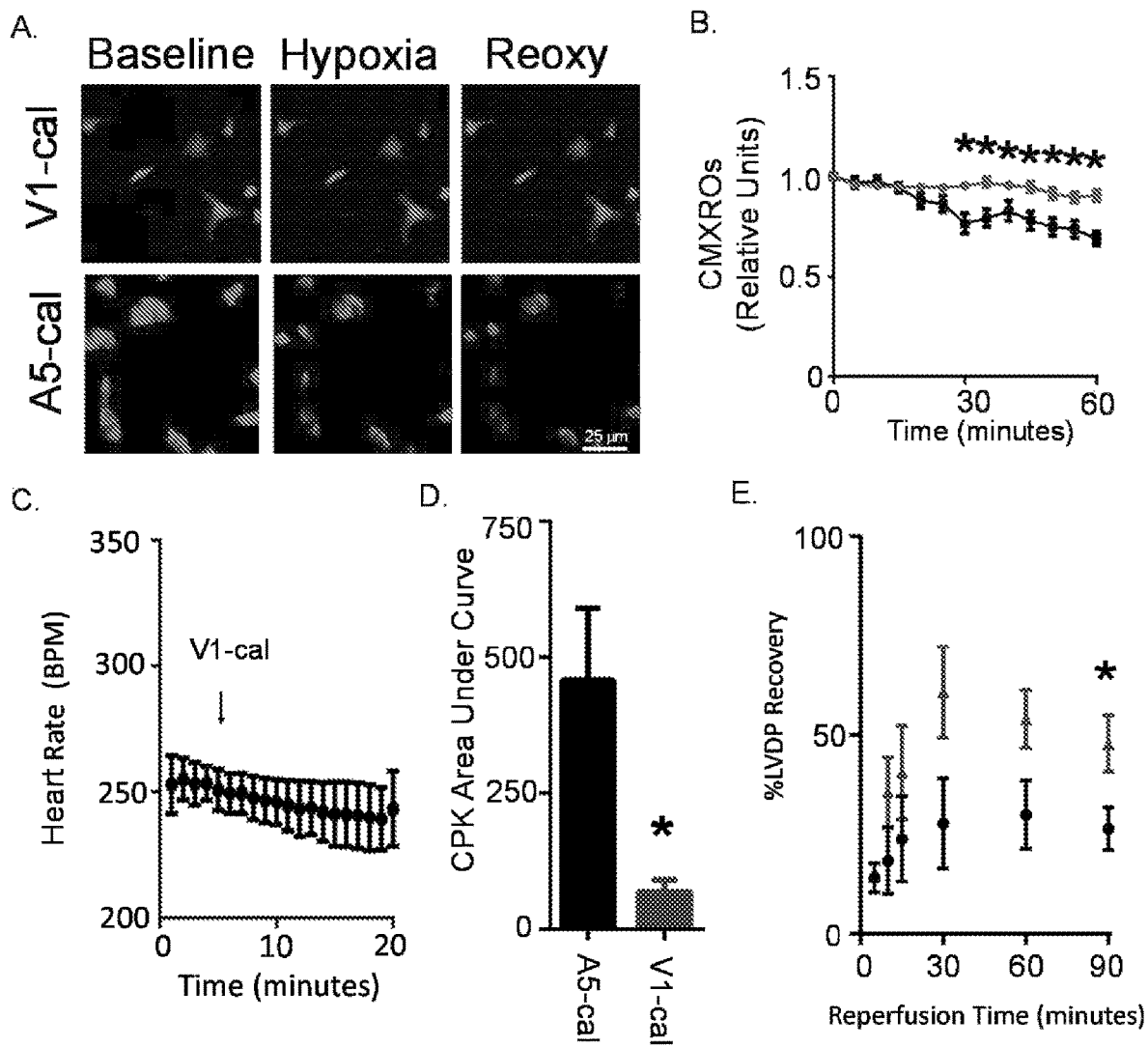
FIG. 15, panels A-E, shows the results of single cell and isolated heart experiments.
Figure 16:
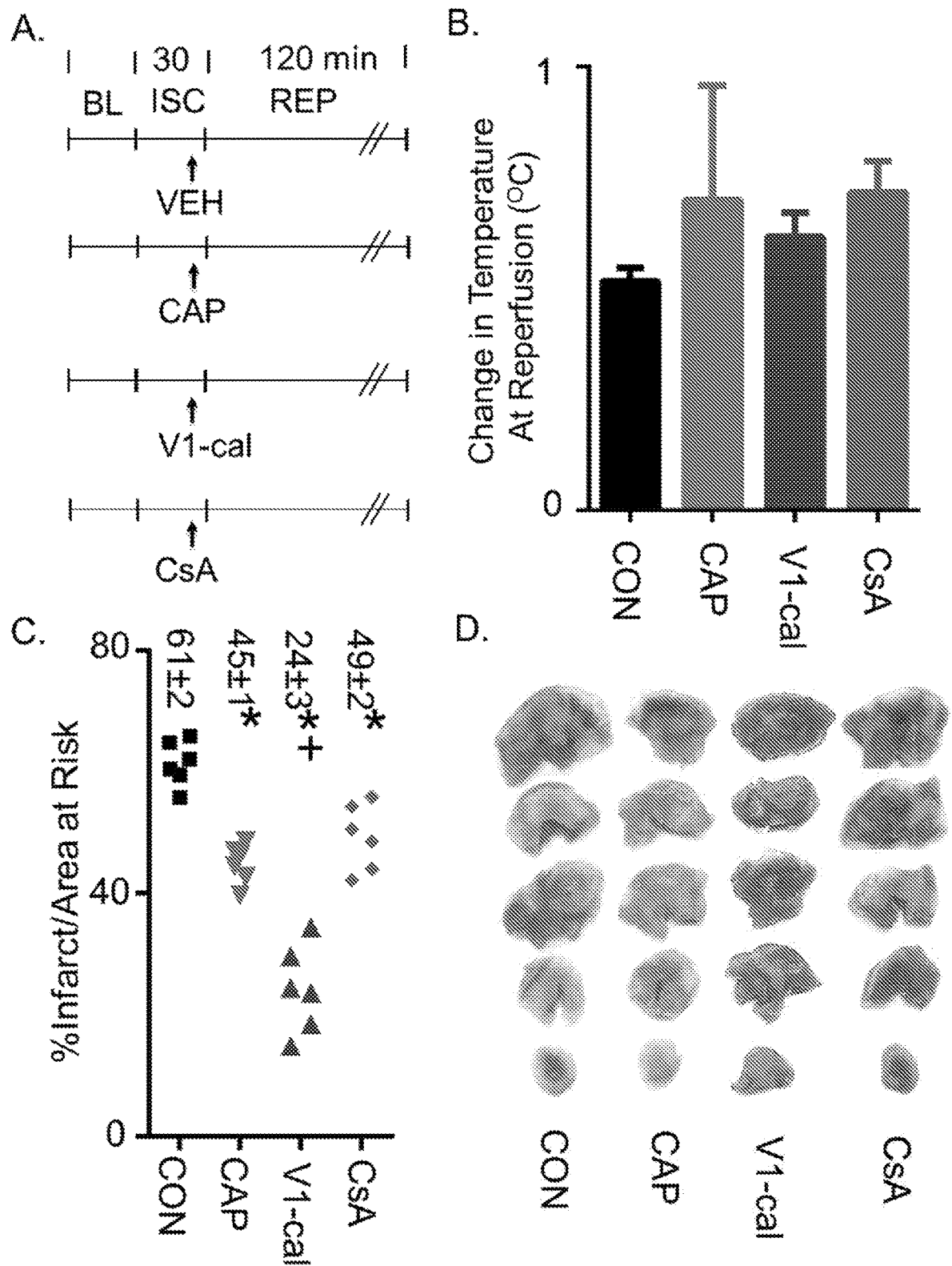
FIG. 16, panels A-D, shows the results of in vivo myocardial infarction experiments.
Figure 18:
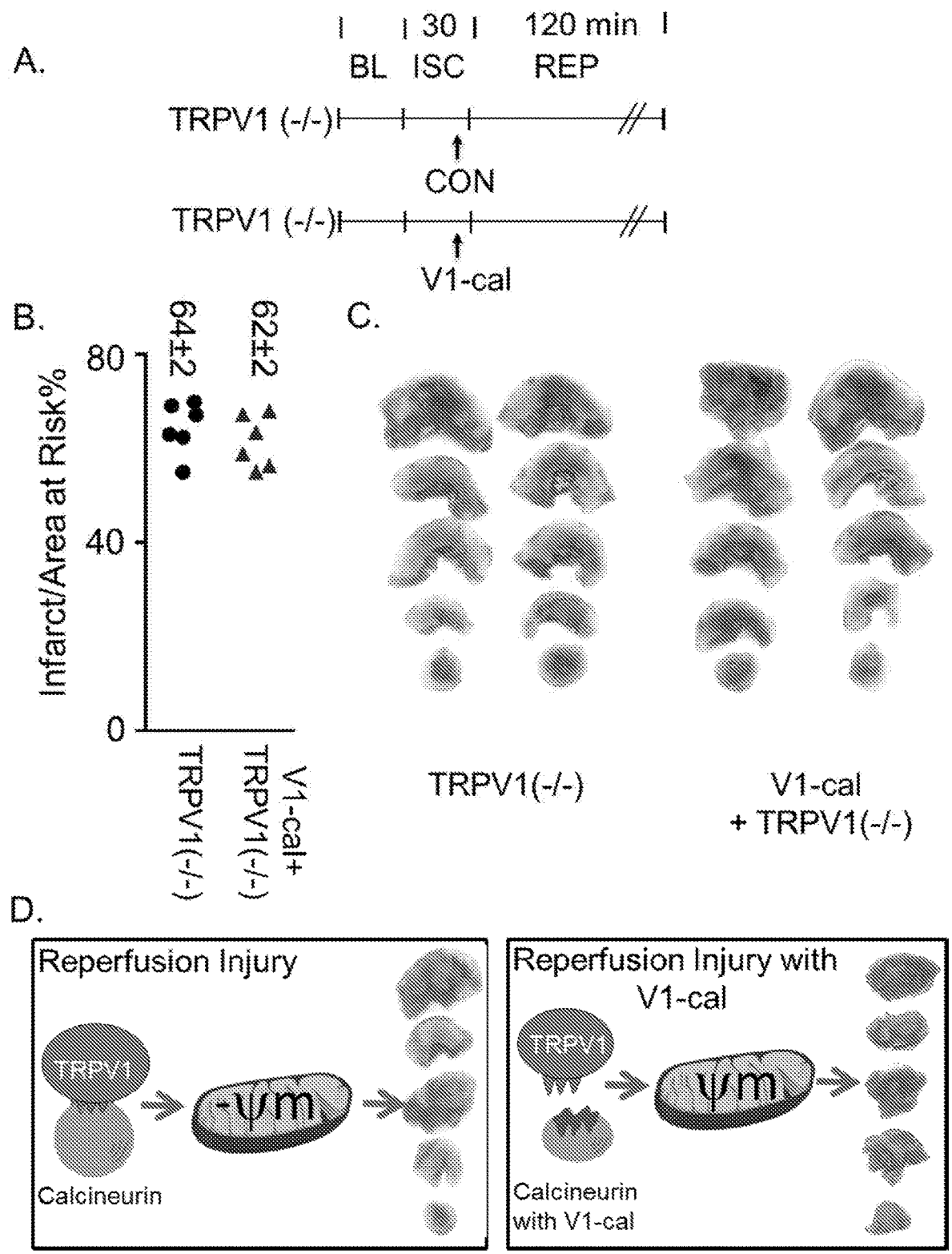
FIG. 18, panels A-D, shows that V1-cal selectively targets TRPV1.

| | Total number of animals used | Number excluded | Reason for exclusion |
|---|---|---|---|
| FIG. 2 | 33 | 3 | Ventricular fibrillation (1), preconditioned (1), suture not released at reperfusion (1); all 3 rats excluded were within the CAP (0.1 mg/kg) group |
| FIG 6 | 33 | 3 | All capsaicin (CAP) (0.1 mg/kg) group, ventricular fibrillation (1), preconditions (1), suture not released at reperfusion (1) |
| FIG. 7 | 8 | 0 | |
| FIG 8 | 25 | 1 | CPZ group, remained in TTC stain overnight instead of formaldehyde |
| FIGs. 14-15 | 15 | 3 | Prior to assigning a group, Cannulation unsuccessful (2), perfused with air (1) |
| FIG. 16 | 25 | 1 | Died 2 days prior to experiment in animal care facility (1) |
| FIG. 18 | 13 | 1 | In TRPV1(−/−) control group, small area at risk from the left ventricle (AAR/LV) (1) |

Primary Neonatal Cardiomyocyte Isolation: Rat pups 1-3 days of age were used for primary neonatal cardiomyocyte isolation as previously described (Disatnik et al., *Journal of the American Heart Association*, 2013. 2:e000461).

Peptide Synthesis: Peptides were synthesized using microwave chemistry on a Liberty Microwave Peptide Synthesizer (CEM Corporation) (Gross et al., *Basic Research in Cardiology*, 2013. 108:381). Peptides were synthesized as one polypeptide with $TAT_{47-57}$ carrier in the following order: N-terminus-$TAT_{47-57}$-spacer (Gly-Gly)-cargo-C-terminus.

RT PCR: Total RNA was isolated from PNCM on day 4 in culture and H9C2 cells at passages 18, 23, 24 (Ambion RNAqueous kit). To reduce DNA contamination in the preparations, the isolated total RNA was subject to precipitation with lithium chloride and DNase digestion (Ambion DNase free). cDNA was generated from mRNA using Takara Primescript cDNA synthesis kit with oligo dT primers. Previously described primers, forward: GGC-CACAGAGGATCTGGAAAAG (SEQ ID NO:112) and reverse: CAACCCTGCTGGTTCCCTAAG (SEQ ID NO:113) for rat TRPV1 (Tian et al., *American Journal of Physiology. Renal Physiology*, 2006. 290:F117-126), were used to amplify the full length coding sequence from the cDNA using Platinum Taq (Invitrogen). The amplified PCR product was subcloned into the pCR TOPO vector (Invitrogen) and sequenced.

Quantitative PCR: cDNA from mRNA was generated from H9C2, PNCM, and heart tissues (RA, LA, RV, LV) as described above. The qPCR reactions were performed using Fast SYBR Green Master Mix (Life Technology). The reactions were done in a total of 20 ul containing 10 ng of cDNA and 200 nM of primers per manufacturer's recommendation. Primers used were forward: CTGACGGCAAGGATGACTACC (SEQ ID NO:114) reverse: ACCTCAGGGAGAAGCTCAGG (SEQ ID NO:115), previously described (Nakanishi et al., *Molecular Biology of the Cell*, 2010. 21:2568-2577). The cycling protocol was as follows: initial denaturing template at 95° C. for 30 secs, followed by 40 cycles of 95° C. denaturing for 3 sec of and 30 secs of annealing/extension at 61° C. After completion, melting curve analysis was performed by gradually increasing the temperature from 60° C. to 95° C. in a graded manner of 0.3° C. every 15 secs.

Western Blot: Heart tissue was homogenized and centrifuged at 800 g to remove cellular debris with the supernatant kept as the total fraction. PNCM, H9C2 and F11 cells (stably overexpressing TRPV1, a gift from Dr. Yoneda) were lysed in RIPA buffer (0.150 M NaCl, 1% Triton X-100, 50 mM HEPES, 1 mM EDTA) containing a cocktail of protease and phosphatase inhibitors. Total protein content was determined by Bradford assay and 75 μg of each homogenate was run on 7.5% SDS-PAGE gels. Total protein lysate were transferred to PVDF membrane and probed overnight at 4° C. for specific antibodies to TRPV1 (1:500, NeuroMab) and GAPDH (1:1000, Sigma). The next day, membranes were washed and incubated in secondary anti-rabbit antibody.

Immunofluorescence: PNCM were seeded onto poly-D-lysine coated glass coverslips at a density 150,000 cells and anti-TRPV1 (1:500; NeuroMab) and anti-TOM20 (1:250; Santa Cruz Biotechnology) were used.

Transmission Electron Microscopy: PNCM were prepared as previously described (Yogalingam et al., *The Journal of Biological Chemistry*, 2013. 288:18947-18960).

Live Cell Imaging: Mitochondrial membrane potential was determined using single cell analysis with an enclosed cellular chamber controlled for temperature, $P_{O2}$, and $P_{CO2}$. For these studies, cells were plated on glass coverslips (MatTek Corporation, 150,000 cells/dish) and maintained at a temperature of 37° C. and 5% $P_{CO2}$. Cells were washed once with DMEM and incubated with TMRE (150 nM) or CMXRos (0.5 μM) for thirty minutes at 37° C.; followed by cells washed again with DMEM 10 minutes prior to being studied.

Two protocols were performed: one consisting of cells subjected to specific treatments under normoxia (21% $P_{O2}$) and for the other protocol cells subjected to hypoxia-reoxygenation. Images of individual cells were taken at baseline and used for normalization of the images acquired at 5 minutes intervals. For the hypoxia-reoxygenation model, cells were exposed to hypoxia (<1% $P_{O2}$) for 30 minutes followed by reoxygenation for 30 minutes.

Cell death for the hypoxia-reoxygenation model was determined by combined microscopic morphological and fluorescent assessment. Live cells exhibited unchanged cellular morphology and TMRE fluorescent stability. Dying cells exhibited characteristics of morphological contracture, assessed relative to the loss of initial cellular architecture pre-hypoxia and disruption of fluorescent TMRE signal.

H9C2 cell model of ischemia-reoxygenation: H9C2 cells at passages 18-24 were seeded at a density of 50,000 cells/well in 24 well plates. Cells were serum starved for a period of 24 hours. After serum starvation, cells were treated with capsaicin (0.1-10 μM) for 1 hour before being subjected to 6 hours of ischemia followed by 16 hours reoxygenation. Ischemia and reoxygenation was induced as previously described and lactate dehydrogenase release was measured (Yogalingam et al., *The Journal of Biological Chemistry*, 2013. 288:18947-18960).

Calcineurin activity assay: Either TAT (10 μM) or V1-cal (10 μM) was incubated with substrate and recombinant calcineurin. A colormetric analysis measured the extent of free phosphate release from the substrate per manufacturer protocol (Calbiochem).

BLAST: Using protein BLAST, the sequence AIXIXD-TEXS (SEQ ID NO:15; where X is any amino acid) was queried for *Homo Sapiens* and *Rattus Norvegicus*. Matches for the sequence were identified.

In Silico Modeling: PDB 3LL8 was imported into UCSF chimera and the switch amino acid function was used to develop the TRPV1 C-terminus sequence interaction with calcineurin A. Cyclophillin D was also incorporated by using PDB 1AUI. The location of the C-terminus sequence of TRPV1 and calcineurin A were further evaluated in Swiss PDB viewer. Selected residues were rendered in solid 3-D format.

Isolated Heart Model: The protocol used was previously described (Gross et al., *Basic Research in Cardiology*, 2013. 108:381). Male Sprague-Dawley rats were subjected to 30 minutes global ischemia followed by 90 minutes reperfusion. Left ventricular pressure balloons were made from plastic wrap as described (Gross et al., *Basic Research in Cardiology*, 2013. 108:381). The balloons were connected to a pressure transducer (MLT-0699, ADI Instruments) to measure ventricular hemodynamics including end diastolic pressure, left ventricular developed pressure, heart rate, +dP/dt, and −dP/dt. Myocardial infarct size was also determined. Creatine phosphokinase was also measured during the first 30 minutes of reperfusion as described (Sigma) (Disatnik et al., *Journal of the American Heart Association*, 2013. 2:e000461).

In Vivo Myocardial Infarction Rodent Model: The model was previously described in a number of publications (Gross et al., *Circulation Research*, 2004. 94:960-966; Gross et al., *Anesthesia and Analgesia*, 2009. 109:1395-1402). To induce remote conditioning, a surgical abdominal incision was performed as described (Gross et al., *Basic Research in Cardiology*, 2013. 108:381). All drugs given were administered through the internal jugular vein. The dose of cyclosporine given was chosen based upon clinical trial (Chiari et al., *Anesthesiology*, 2014. 121:232-238; Cung et al., *The New England Journal of Medicine*, 2015. 373:1021-1031). The carotid artery was cannulated and used to measure blood pressure and heart rate. After stabilization, rodents were given treatments as described while subjected to 30 minutes of left anterior descending coronary artery occlusion followed by 2 hours reperfusion. Core body temperature was monitored rectally. Hemodynamics and infarct size were assessed.

Statistical Analysis: All groups are reported as mean±standard error of the mean (SEM). A one-way ANOVA followed by Bonferroni correction for multiplicity was used to compare each group to the control group for TMRE studies and infarct size measurements. A two-way ANOVA was used to determine significance for hemodynamic parameters. A two-tailed Students t-test was used when only 2 groups were compared. Statistical analysis was performed using GraphPad Prism 6.

Example 1

TRPV1 Regulates Mitochondrial Membrane Potential and Myocardial Reperfusion Injury Methods and Results Summary: In primary cardiomyocytes, confocal and electron microscopy demonstrate TRPV1 is localized to the mitochondria. Capsaicin, the specific TRPV1 agonist, dose-dependently reduced mitochondrial membrane potential and was blocked by the TRPV1 antagonist, capsazepine, or the calcineurin inhibitor, cyclosporine. Using in silico analysis, we discovered an interaction site for TRPV1 with calcineurin. a peptide, V1-cal, was synthesized to inhibit the interaction between TRPV1 and calcineurin. In an in vivo rat myocardial infarction model, V1-cal, given just prior to reperfusion, substantially mitigated myocardial infarct size when compared to vehicle, capsaicin or cyclosporine 24±3%* versus control: 61±2%, capsaicin: 45±1%, cyclosporine: 49±2%, n=6/group,*P<0.01 versus all groups). The infarct size reduction by V1-cal was also not seen in TRPV1 knockout rats.

Method and Results:

It was first determined whether transient receptor potential vanilloid 1 (TRPV1) regulated myocardial infarct size reduction in a rat model of remote conditioning (FIG. 1). An abdominal incision prior to left anterior descending coronary artery (LAD) ischemia and reperfusion reduced myocardial infarct size compared to control. Incision-induced infarct size reduction was blocked by the TRPV1 antagonist capsazepine (3 mg/kg); given through the internal jugular vein 10 minutes before the incision. When administering capsazepine alone, no differences were noted for infarct size compared to the control group (FIG. 1B). No differences were noted for area at risk/left ventricle (AAR/LV) percent (FIG. 2) or for differences in hemodynamics between groups (TABLE 2).

TABLE 2

Hemodynamic results for in vivo remote conditioning

| | | Baseline | | | 15 min Ischemia | | | 2 hrs Reperfusion | | |
|---|---|---|---|---|---|---|---|---|---|---|
| | n | HR | MAP | RPP | HR | MAP | RPP | HR | MAP | RPP |
| Control | 6 | 387 ± 12 | 126 ± 8 | 57 ± 4 | 400 ± 11 | 110 ± 5 | 51 ± 3 | 378 ± 9 | 80 ± 5 | 40 ± 3 |
| In | 6 | 388 ± 12 | 128 ± 4 | 59 ± 2 | 388 ± 11 | 110 ± 7 | 50 ± 3 | 358 ± 12 | 86 ± 5 | 39 ± 2 |
| CPZ + In | 6 | 382 ± 9 | 123 ± 5 | 55 ± 2 | 363 ± 14 | 107 ± 8 | 44 ± 4 | 355 ± 13 | 80 ± 5 | 36 ± 2 |
| CPZ | 5 | 384 ± 5 | 121 ± 4 | 55 ± 2 | 396 ± 10 | 115 ± 9 | 52 ± 5 | 374 ± 5 | 82 ± 3 | 39 ± 1 |

HR = heart rate (beats/min), MAP = mean arterial pressure (mmHg), RPP = rate pressure product (mmHg/1000).

FIG. 1: Remote conditioning is mediated by TRPV1. A. Experimental protocol, consisting of 4 groups. An incision was performed 15 minutes prior to ischemia. Capsazepine was given 5 minutes prior to incision or alone intravenously. B. Infarct size per area at risk percentage for each experimental group. Data points are for each individual experiment, with mean±SEM for each group listed under the individual data points. BL=baseline, RX=treatment period, ISC=ischemia, REP=reperfusion, CON=control, CPZ=capsazepine *P<0.01 versus vehicle, +P<0.01 versus incision alone, n=5-6/group.

FIG. 2: Area at risk per left ventricle for each individual group. CON=control, IN=incision, CPZ=capsazepine.

Since it was determined that TRPV1 activation is required for remote conditioning, it was focused on whether this TRPV1-mediated effect occurred in the cardiomyocyte, instead of being primarily neuronal mediated. Unexpectedly, TRPV1 was detected by qPCR and Western blot in heart homogenate, primary neonatal cardiomyocytes (PNCM) and left-ventricle derived immortalized cell line H9C2 (FIG. 3A-3B, FIG. 4A-4C). Quantitative PCR detected TRPV1 in all four chambers of heart homogenate, PNCM, and H9C2 cells (FIG. 3A). Corrected Ct values to GAPDH suggested TRPV1 was more highly expressed in PNCM and H9C2 cells compared to heart homogenates from all four heart chambers (FIG. 4C). Western blot for homogenates implied TRPV1 expression was mainly intracellular for cardiomyocytes, since compared to the neuronal cells F11, minimal cell surface expression was noted; surface expression of TRPV1 is associated with glycosylation thus resulting in a 120 kDa band, rather than an intracellular 95 kDa band (FIG. 3B) (Jahnel et al., *European Journal of Biochemistry/FEBS*, 2001. 268:5489-5496). Since TRPV1 splice variants are known to exist, RT-PCR was further performed. In PNCM and H9C2 cells, a single band at the expected base pair length was present (FIG. 3C). Sequencing of TRPV1 from PNCM revealed a sequence similar to other previously documented non-cardiac TRPV1 sequences (Accession: NP_114188.1 and XP_008766014.1). Additionally, no splice variants, previously found in other cell lines derived from visceral organs, were detected (FIG. 4D) (Tian et al., *American Journal of Physiology. Renal Physiology*, 2006. 290:F117-126). The localization of TRPV1 within the cell was examined using confocal microscopy. It was discovered that TRPV1 co-localized with the mitochondrial specific protein TOM-20 in PNCM (FIG. 3D). Using electron microscopy with TRPV1 immunogold labeling, several gold particles were detected on or in the mitochondria per field and more than one particle per mitochondria was found (FIG. 3E). TRPV1 was found to co-localize with TOM20 in primary adult cardiomyocytes (FIG. 4)

FIG. 3: Biochemical evidence TRPV1 is present in cardiomyocytes. A. Quantitative PCR for the 4 heart chambers (LV, LA, RV and RA), PNCM, and H9C2 cell line (n=4 biological replicates, measured each in triplicate). B. Western blot of total left ventricle heart homogenate, PNCM and H9C2 cells. A dorsal root ganglion-derived cell line, F11, was used as a positive control. TRPV1 is intracellular (95 kDa) and glycosylated at the plasma membrane (120 kDa). GAPDH was used as a loading control (representative of n=3 biological replicates). C. RT-PCR of PNCM and H9C2 cells. D. Confocal imaging of TRPV1 in PNCM with co-localization to TOM20, a specific mitochondrial membrane protein. E. Electron microscopy of mitochondria labeled for TRPV1 with immunogold particles (red arrows).

FIG. 4: A. TRPV1 co-localizes with TOM20 in primary adult cardiomyocytes. B. Knockout verification of the antibody for selectivity. In addition this also validates that the rodent model purchased also had TRPV1 knocked out in primary cardiomyocytes.

FIG. 5: A. Representative TRPV1 DNA gel for qPCR experiments. B. Representative TRPV1 melt curve for qPCR experiments. C. Delta Ct relative to GAPDH for heart chambers and cells. D. Sequence of TRPV1 in rat neonatal primary cardiomyocytes. Underlined portions are regions sequenced prior to and after the TRPV1 start and end sequence.

Next, since TRPV1 is localized to the mitochondria, it was determined whether TRPV1 functions at the mitochondria. This was done by measuring mitochondrial membrane potential after administration of the specific TRPV1 agonist capsaicin (range of 0.1-10 µM). Using primary neonatal cardiomyocytes, capsaicin dose-dependently decreased mitochondrial membrane potential assessed by cell imaging using tetramethylrhodamine ethyl ester (TMRE) (FIG. 6). Using a cell culture model of ischemia-reoxygenation, capsaicin reduced LDH release at a low concentration (0.1 µM), which did not occur for higher capsaicin concentration (1 and 10 µM, FIG. 7A). For isolated un-paced rat hearts, unlike vehicle (DMSO), capsaicin increased heart rate during the first 15 minutes of infusion (FIG. 7B-7C). Due to the capsaicin-dependent changes in heart rate, an in vivo LAD ligation model of ischemia-reperfusion injury was used and further tested how different capsaicin doses affect myocardial infarct size in vivo (FIG. 6). After administration, capsaicin dose-dependently increased heart rate when given intravenously (FIG. 6). The doses of capsaicin given also reduced myocardial infarct size in a narrow therapeutic window (0.1-1.0 mg/kg). A capsaicin dose of 3.0 mg/kg failed to reduce myocardial infarct size (FIG. 6). For groups tested, no differences were noted in the area at risk/left ventricle percent (FIG. 7D). Hemodynamics, including heart rate, blood pressure and rate pressure product were also assessed for these groups (TABLE 3).

TABLE 3

Hemodynamic results for in vivo pre-conditioning

| | n | Baseline | | | 15 min Ischemia | | | 2 hrs Reperfusion | | |
| --- | --- | --- | --- | --- | --- | --- | --- | --- | --- | --- |
| | | HR | MAP | RPP | HR | MAP | RPP | HR | MAP | RPP |
| Control | 6 | 345 ± 6 | 127 ± 4 | 51 ± 2 | 352 ± 4 | 109 ± 4 | 44 ± 2 | 350 ± 8 | 92 ± 3 | 38 ± 1 |
| CAP (0.1) | 6 | 377 ± 13 | 128 ± 4 | 60 ± 5 | 373 ± 10 | 110 ± 7 | 47 ± 4 | 362 ± 6 | 86 ± 5 | 39 ± 2 |
| CAP (0.3) | 6 | 370 ± 11 | 137 ± 7 | 60 ± 5 | 360 ± 21 | 89 ± 14 | 40 ± 7 | 368 ± 6 | 85 ± 3 | 38 ± 2 |
| CAP (1.0) | 6 | 353 ± 11 | 131 ± 6 | 55 ± 3 | 385 ± 15 | 104 ± 10 | 46 ± 5 | 367 ± 3 | 79 ± 3 | 36 ± 2 |
| CAP (3.0) | 6 | 357 ± 8 | 127 ± 4 | 53 ± 2 | 420 ± 9 | 113 ± 5 | 53 ± 3 | 370 ± 4 | 72 ± 4 | 35 ± 2 |
| CPZ + CAP | 6 | 370 ± 11 | 134 ± 4 | 58 ± 3 | 385 ± 10 | 106 ± 11 | 46 ± 4 | 383 ± 16 | 74 ± 3 | 37 ± 1 |
| CsA + CAP | 6 | 424 ± 7 | 100 ± 4 | 54 ± 2 | 443 ± 5 | 88 ± 5 | 48 ± 3 | 409 ± 14 | 68 ± 3 | 35 ± 4 |
| CPZ | 5 | 366 ± 7 | 129 ± 6 | 56 ± 3 | 356 ± 14 | 108 ± 12 | 45 ± 5 | 356 ± 7 | 89 ± 3 | 39 ± 2 |
| CsA | 6 | 410 ± 11 | 106 ± 5 | 54 ± 4 | 433 ± 1 | 89 ± 4 | 48 ± 2 | 399 ± 14 | 78 ± 3 | 40 ± 3 |

FIG. 6: TRPV1 regulates mitochondrial membrane potential and infarct size. A. Representative images (at baseline [BL] and 30 minutes [30] after drug application) for assessment of mitochondrial membrane potential by TMRE for PNCM treated with vehicle (DMSO) or capsaicin (0.1, 1 or 10 mM). B. TMRE fluorescence measurements (relative to each baseline measurement set at 1) for vehicle or capsaicin (0.1, 1.0, or 10 mM). Capsiacin dose-dependently causes changes in mitochondrial membrane potential over 30 minutes, as assessed by TMRE (n=3 biological replicates/group, ⁺P<0.05 versus control, *P<0.01 versus control). C. Experimental protocol for myocardial ischemia-reperfusion studies. Arrow indicates time of treatment for either control or capsaicin. D. Change in heart rate after capsaicin administration. Capsaicin logarithmically increased heart rate in a dose-dependent fashion (n=6/group, *P<0.01). E. Capsaicin maximally decreased infarct size at 0.3 mg/kg, with partial effects at 0.1 mg/kg and 1.0 mg/kg. Individual infarct size for each experiment are presented (n=6/group, *P<0.01 versus vehicle).

FIG. 7: A. Cell ischemia-reoxygenation experiments with H9C2 cells. Capsaicin reduced LDH release only for a lower dose (0.1 μM) when compared to higher doses of capsaicin (1 and 10 μM), n=8/group, *P<0.01, ⁺P<0.05 versus control. Percentage of LDH release noted as mean±SEM B,C. In isolated hearts after capsaicin administration, capsaicin (0.1 μM) increases heart rate unlike vehicle (DMSO) ⁺P<0.05 versus prior to administration, n=4/group. D. Area at risk per left ventricle percentage for each group.

It was tested whether the capsaicin-induced mitochondrial membrane potential changes and infarct size reduction were specific to TRPV1 and calcineurin dependent. The changes in mitochondrial membrane potential induced by capsaicin were blocked by the TRPV1 antagonist, capsazepine, or the calcineurin inhibitor, cyclosporine (FIG. 8). It was further tested whether capsazepine or cyclosporine block preconditioning-induced infarct size reduction for capsaicin in vivo (FIG. 8). Either capsazepine or cyclosporine A reduced the change in heart rate afforded by capsaicin administration at the 0.3 mg/kg dose (FIG. 8). Furthermore, capsazepine or cyclosporine blocked the infarct size sparing effect of capsaicin (FIG. 8). For groups tested, no differences were noted in the area at risk/left ventricle percent (FIG. 9). Hemodynamics, including heart rate, blood pressure and rate pressure product were also assessed for these groups (TABLE 3).

FIG. 8: Calcineurin inhibition regulates mitochondrial membrane potential and infarct size. A. Representative images (at time baseline [BL] and 30 minutes [30'] after drug application) for assessment of mitochondrial membrane potential by TMRE for PNCM treated with control, (DMSO) or capsaicin (1 mM). A subset of groups was treated 10 minutes prior to capsaicin with capsazepine (1 mM) or cyclosporine A (1mM). B. TMRE fluorescence measurements for CON, CAP, CPZ+CAP or CsA+CAP for 30 minutes, as assessed by TMRE (n=3 biological replicates/group, ⁺P<0.05 or *P<0.01 for CON, CPZ+CAP, or CsA+CAP versus CAP). C. Experimental protocol for myocardial ischemia-reperfusion studies. Treat indicates time of treatment for either control or capsaicin given 30 minutes prior to ischemia. Arrow with Inhibit indicates time of treatment for either capsazepine (3 mg/kg) or cyclosporine (2.5 mg/kg) 40 minutes prior to ischemia. D. Heart rate increase caused by capsaicin is blocked by either CPZ or CsA. E. Either CPZ or CsA blocks CAP-induced infarct size reduction. For comparison purposes, both CON and CAP were replotted from FIG. 2D and 2E, for FIG. 3D and 3E, respectively. *P<0.01 versus control, ⁺P<0.01 versus capsaicin alone, CPZ=capsazepine (3 mg/kg), CsA=cyclosporine (2.5 mg/kg), CAP=capsaicin FIG. 9: A. Representative images of PNCM at time 0 and after 30 minutes of treatment with DMSO alone, CPZ+ DMSO and CsA+DMSO groups. B. Graph of data collected for groups including the DMSO alone (triangle), CPZ+ DMSO (square) and CsA+DMSO (diamond) groups (n=3 biological replicates per group) C. Area at risk per left ventricle for each individual group.

These findings suggested that TRPV1 reduces myocardial injury with a narrow therapeutic window through a calcineurin-dependent mechanism by altering mitochondrial dynamics. It was tested whether limiting, yet not completely blocking, TRPV1 channel gating could be an effective strategy to reduce myocardial reperfusion injury. To do so, a short acting therapeutic that could break the interaction of calcineurin with TRPV1 was designed and tested whether TRPV1-induced changes in membrane potential within the mitochondria could be limited.

The AKAP5 sequence which interacts with calcineurin A was recently crystalized (Li et al., *Nature Structural& Molecular Biology*, 2012. 19:337-345). Therefore, it was determined whether a homologous interaction site for calcineurin exists on TRPV1 using sequence homology with AKAP5. Using L-align, a sequence within the C-terminus of TRPV1 was found, which contained a >50% sequence homology to the region of AKAP5 crystalized to the calcineurin A subunit (FIG. 10). A BLAST search using the input AIXIXDTEXS (SEQ ID NO:15; X is a wild card in BLAST used to represent any amino acid) returned only sequences identified for either TRPV1 or AKAP5. The TRPV1 sequence was also in a C-terminus region of TRPV1, forming an alpha coil-coil, which is part of the inner pore forming unit of the TRPV1 channel (FIG. 10) (Liao et al., *Nature*, 2013. 504:107-112). The start of the intracellular portion of TRPV1 is approximately near 1689 (FIG. 19, panel A). The peptide cargo designed is located and perpendicular to the inner pore forming unit of TRPV1 (FIG. 19, panel B). The structure from F712-R721 was not solved by electron cryomicroscopy. This region is predicted to be an alpha helix. An alpha wheel was used to plot the missing region (FIG. 19, panel C). The alpha wheel for TRPV1 suggests several phosphorylation domains (T704, T708, S711) and a reactive cysteine (C715) all lie within a single region (FIG. 19C). Based upon the sequence homology to AKAP5, an initial peptide, peptide 1 (P1) linked to $TAT_{47-57}$, was synthesized and used for testing in proof of concept studies. P1 was initially chosen as it covers all 3 phosphorylation sites (T704, T708, and S711) while avoiding C715 (a reactive free thiol group). This region is also extremely attractive in peptide chemistry to develop an inhibitor since the region can be modified by cyclization (linking to K710, K714 or K718) or stapled (on the opposite side of T704, T708, and S711) to improve stability and biological half-life. Additional derivations of this peptide are also described as P1 through P9 (FIG. 19D).

Figure 11:
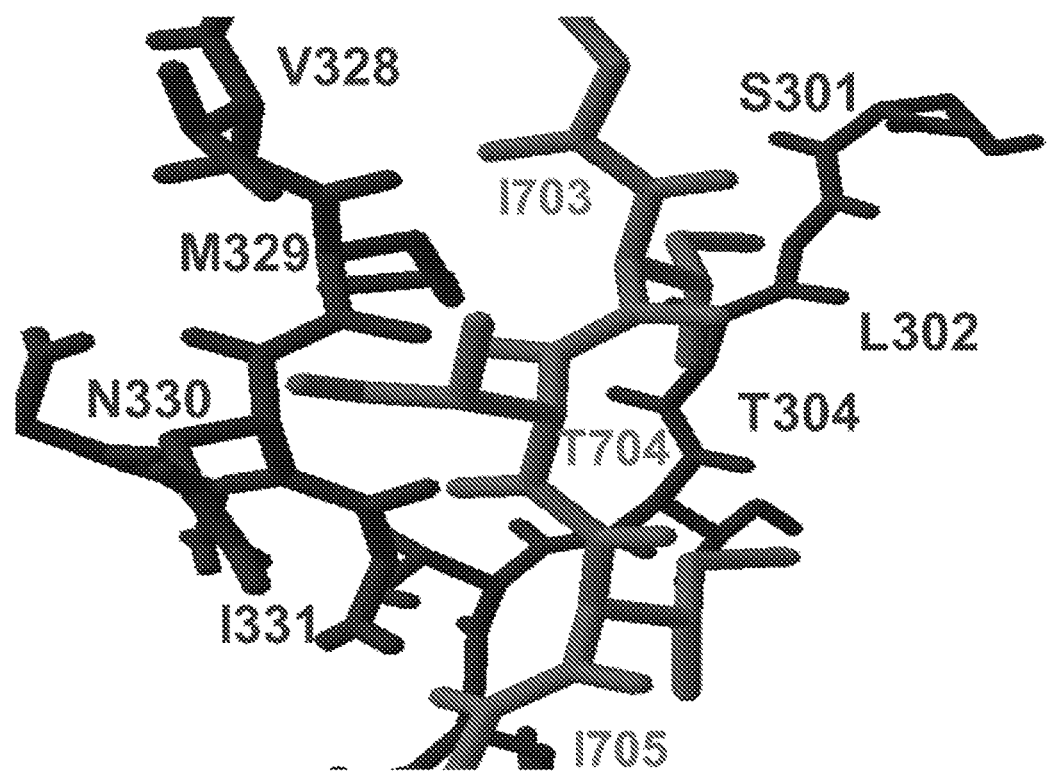
FIG. 11, panels A-B. Panel A shows that sequences of V1-cal are conserved and shows the effect of V1-cal and CAP on cells. The V1-cal sequences depicted are: Human, SEQ ID NO:4; Cow, SEQ ID NO:4; Rat, SEQ ID NO:4; Mouse, SEQ ID NO:4; Guinea Pig, SEQ ID NO:4; Rabbit, SEQ ID NO:5; and Canine, SEQ ID NO:4. Panel B depicts a structure showing T704 of TRPV1 is near N330 site of calcineurin A.

Furthermore, this region on TRPV1 was evolutionary conserved in mammals (FIG. 11). The TRPV1 region was further modelled against the calcineurin A complex and cyclophilin D using PDB 3LL8 and 1AU123 (Jin and Harrison, *Proc. Natl. Acad. Sci. USA.*, 2002. 99:13522-13526). Unlike cyclosporine A, which disrupts the interaction between cyclophilin D and the calcineurin B subunit, this TRPV1 region directly interacts with the calcineurin A subunit (FIG. 10). In particular, Thr704 of TRPV1 is in close proximity to N330; similar to how the Thr in the classical calcineurin inhibitor peptide PVIVIT interacts with calcineurin A at N330 (FIG. 10) (Li et al., *Journal of Molecular Biology*, 2007. 369:1296-1306). Based on the region's sequence homology to AKAP5, evolutionary conservation, and location on the TRPV1 channel, a peptide against this region was synthesized and linked to $TAT_{47-57}$ for intracellular entry and called the peptide V1-cal (FIG. 10).

FIG. 10: The calcineurin A interaction site with TRPV1. A. The known interaction site of calcineurin A with AKAP5 has 54% sequence homology to a region on TRPV1 (:=homologous amino acid). B. This site on TRPV1, in red, forms a coiled-coiled region perpendicular to the pore forming unit of TRPV1. C. Predicted interaction site of V1-cal with calcineurin A, based upon the crystallization of the AKAP5 peptide with calcineurin A (3LL8). *=interaction site of complex with cyclosporine A; +=catalytic site for calcineurin A. D. Based on homology and structure, a peptide, V1-cal, was synthesized against the alpha coiled-coil TRPV1 region and linked to TAT for intracellular entry. E. In vitro kinase assay measuring calcineurin activity by free phosphate release (n=3/group), *P<0.05.

FIG. 11: A. The TRPV1 region of where V1-cal was constructed is strongly conserved in mammals. B. Structure showing T704 of TRPV1 is near N330 site of calcineurin A.

FIG. 12: Determination of peptide stability. A. At baseline a single peak at 5 minutes was noted when V1-cal was analyzed by RP-HPLC (arrow in green). B. 10 minutes after trypsin digestion, V1-cal is still detected (arrow in green), yet is 75% degraded with the with multiple peaks detected as degradation products of V1-cal (black arrows). C. 20 minutes after exposure to trypsin, V1-cal is 100% degraded (with no peak at 5 minutes and multiple other peaks shown with black arrows detected).

Figure 13:
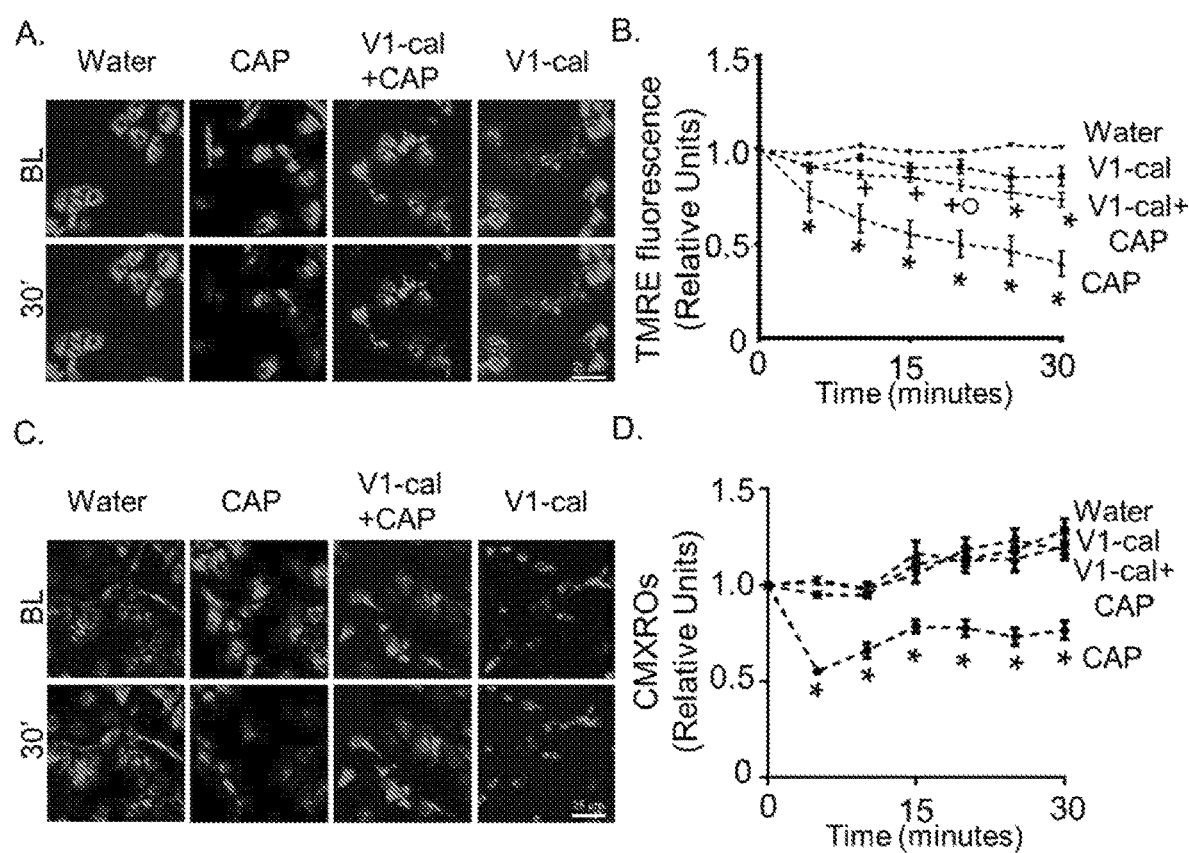
FIG. 13, panels A-D, shows changes in mitochondrial membrane potential.

FIG. 13: V1-cal abrogates TRPV1-induced changes in mitochondrial membrane potential. A. Representative TMRE images of PNCM at baseline [BL] and after 30 minutes [30'] of treatment with water, capsaicin, V1-cal+ capsaicin, or V1-cal alone. B. Mitochondrial membrane potential assessed by TMRE for PNCM treated with V1-cal (1 mM) prior to capsaicin (1mM). n=3 biological replicates/ group, $^+$P<0.01 versus capsaicin alone, $^°$P<0.05 versus water, *P<0.01 versus water). C. Representative CMXRos images of PNCM at baseline and after 30 minutes of treatment with water, capsaicin, V1-cal+capsaicin, or V1-cal alone. D. Mitochondrial membrane potential assessed by CMXRos for PNCM treated with V1-cal (1 mM) prior to capsaicin (1 mM). n=3 biological replicates/group, *P<0.01 versus all other groups).

V1-cal was initially tested in a competitive in vitro calcineurin activity assay. In comparison to TAT, V1-cal reduced the ability for calcineurin to dephosphorylate a calcineurin substrate as measured by free phosphate release in vitro (FIG. 10). Since the interaction of calcineurin with TRPV1 is inducible (Por et al., The Biochemical Journal, 2010. 432:549-556), when primary neonatal cardiomyocytes were treated with V1-cal (1 µM) 10 minutes prior to capsaicin (1 µM), the negative change in mitochondrial membrane potential caused by capsaicin was reduced 10-fold in the presence of V1-cal (FIG. 10).

The effect of V1-cal in an isolated heart model of ischemia-reperfusion injury (that is devoid of nervous system input) was tested. For comparison, the sequence against AKAP5 corresponding to the TRPV1 sequence, AIIITIL-DTEIS (SEQ ID NO:95), was also synthesized linked to TAT$_{47-57}$, which was named A5-cal. Rats were given either V1-cal or A5-cal for 10 minutes prior to ischemia and during the initial 3 minutes of reperfusion (FIG. 14E). Unlike capsaicin, neither peptide had any effects on heart rate when infused (FIG. 15C). Distinct from A5-cal, V1-cal reduced creatine phosphokinase (CPK) release during the first 30 minutes of reperfusion including significant differences in the area calculated under the curve (FIG. 15D). Compared to A5-cal, the recovery of left ventricular developed pressure was improved with V1-cal (FIG. 15E). Trends towards improved + and −dP/dt were also noted. Most importantly, V1-cal significantly reduced myocardial infarct size compared to A5-cal (FIGS. 14F-14G).

FIG. 14: PNCM single cell hypoxia-reoxygenation and isolated heart myocardial infarction experiments. A. Cell hypoxia-reoxygenation experimental protocol. PNCM were subjected to 30 minutes hypoxia followed by 30 minutes reperfusion. Cells were treated with A5-cal (1 mM) or V1-cal (1 mM) prior to hypoxia and prior reoxygenation (arrow labeled treat). During the protocol, oxygen levels were continuously monitored. B. V1-cal significantly reduces the number of dead cells after hypoxia-reoxygenation (n=3 biological replicates/group, *P<0.05). C. Representative TMRE images of PNCM at baseline, after hypoxia and after reoxygenation with A5-cal or V1-cal. D. Mitochondrial membrane potential assessed by TMRE for PNCM treated with A5-cal or V1-cal (n=3 biological replicates/group, *P<0.01 versus A5-cal). E. Isolated heart experimental protocol. Both V1-cal and A5-cal were given at doses of 1 mM for 10 minutes prior to ischemia and 3 minutes during reperfusion. F. Representative infarct size images for 3 hearts per each group (n=6/group, *P<0.01). G. Infarct size per left ventricle percentage for each group with individual data points presented.

FIG. 15: Single cell and isolated heart experiments A. Representative CMXRos images of PNCM at time 0 and after hypoxia-reoxygenation with A5-cal or V1-cal. B. Mitochondrial membrane potential assessed by CMXRos for PNCM treated with A5-cal (1mM) or V1-cal (1 mM) (n=3 biological replicates/group, *P<0.01 versus A5-cal). C. Heart rate measured during the 10 minutes of administration for V1-cal. D. Creatine phosphokinase release during the first 30 minutes of reperfusion. E. Percentage of left ventricle developed pressure (LVDP) compared to baseline. Data presented as mean±SEM, black=A5-cal group, purple=V1-cal group, n=6/group, *P<0.05.

Figure 17:
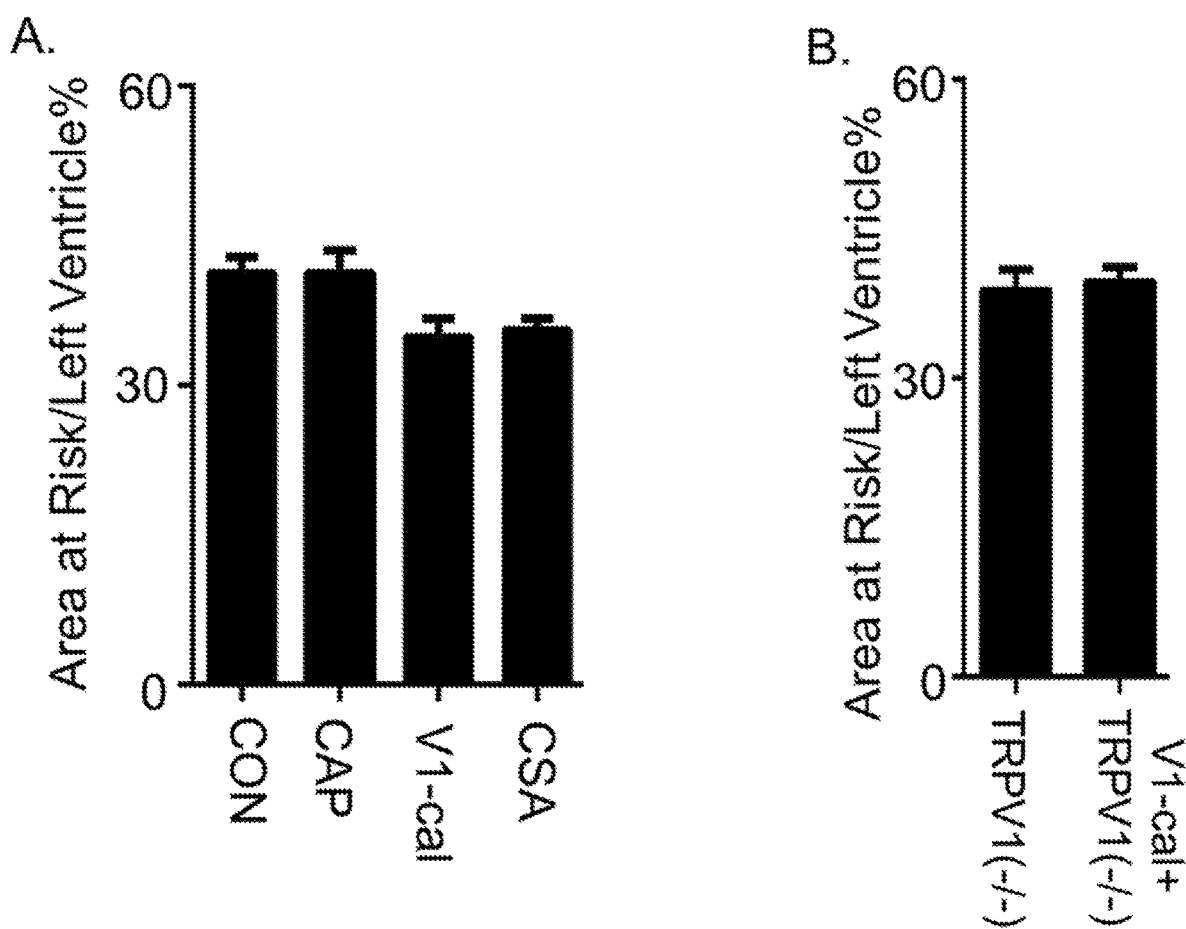
FIG. 17, panels A-B, shows the results from in vivo experiments.

It was tested whether V1-cal compared to either capsaicin or cyclosporine A could reduce myocardial infarct size as a single intravenous bolus just prior to reperfusion in an in vivo LAD ischemia-reperfusion injury model (FIG. 16). Since a prior report suggested that capsaicin reduces myocardial infarct size due to producing hypothermia (Dow et al., Cardiovascular Drugs and Therapy, 2014. 28:295-301), rectal body temperature for each group was measured (TABLE 5). None of the agents administered when compared to control changed thermoregulation for the rodent model used which involves warming with heating lamps and using a heated table (FIG. 16). V1-cal significantly reduced myocardial infarct size by 61% when compared to control, compared to the 27% and 20% infarct size reduction by capsaicin or cyclosporine A, respectively, when given 5 minutes prior to reperfusion (FIG. 16). No differences were noted in area at risk/left ventricle percent (FIG. 17) or hemodynamics (TABLE 5).

TABLE 4

Hemodynamic results for in vivo reperfusion studies

| | | Baseline | | | | 15 min Ischemia | | | | 2 hrs Reperfusion | | | |
|---|---|---|---|---|---|---|---|---|---|---|---|---|---|
| | n | HR | MAP | RPP | TIME | HR | MAP | RPP | TIME | HR | MAP | RPP | TIME |
| Control | 6 | 371 ± 10 | 118 ± 7 | 48 ± 3 | 36.6 ± 0.2 | 385 ± 11 | 103 ± 12 | 43 ± 5 | 36.9 ± 0.2 | 378 ± 16 | 92 ± 6 | 39 ± 3 | 37.1 ± .02 |
| CAP | 6 | 370 ± 6 | 134 ± 3 | 58 ± 2 | 36.8 ± 0.2 | 377 ± 11 | 118 ± 10 | 51 ± 5 | 37.7 ± 0.13 | 363 ± 9 | 87 ± 7 | 39 ± 3 | 37.5 ± 0.1 |
| V1A | 6 | 428 ± 6 | 115 ± 5 | 49 ± 3 | 36.6 ± 0.5 | 432 ± 10 | 110 ± 5 | 47 ± 5 | 37 ± 3 36.6 ± 0.1 | 389 ± 15 | 68 ± 5 | 26 ± 3 | 37.2 ± 0.1 |
| CSA | 6 | 413 ± 14 | 99 ± 6 | 36 ± 8 | 36.6 ± 0.2 | 398 ± 16 | 75 ± 6 | 30 ± 3 | 36.5 ± 0.1 | 389 ± 15 | 68 ± 5 | 26 ± 3 | 37.2 ± 0.1 |
| TRPV1 (−/−) | 6 | 423 ± 14 | 122 ± 5 | 62 ± 4 | 36.9 ± 0.1 | 430 ± 12 | 104 ± 10 | 52 ± 5 | 37.1 ± 0.1 | 392 ± 7 | 82 ± 7 | 43 ± 4 | 37.3 ± 0.2 |
| V1A + TRPV1 (−/−) | 6 | 439 ± 12 * | 123 ± 6 | 61 ± 4 | 36.9 ± 0.2 | 446 ± 13 | 114 ± 7 | 56 ± 4 | 37.1 ± 0.1 | 39 ± 15 | 84 ± 8 | 40 ± 4 | 37 ± 0.1 |

FIG. 16: In vivo myocardial infarction experiments. A. Experimental protocol. All agents were give 5 minutes prior to reperfusion. B. Temperature difference at reperfusion relative to baseline measurements for each group. C. Infarct size per area at risk percentage. D. Representative images of left ventricle area at risk for each group. (n=6/group, *P<0.01 versus control, +P<0.01 versus all groups) CAP=capsaicin, 0.3 mg/kg, CsA=cyclosporine, 2.5 mg/kg, V1-cal, 1 mg/kg FIG. 17: In vivo experiments. A. Area at risk per left ventricle for each group. B. Area at risk per left ventricle for each group.

To confirm selectivity of V1-cal, V1-cal was administered to male Sprague-Dawley TRPV1 knockout rats (FIG. 18). Compared to wild type Sprague-Dawley rats, the infarct size sparing effect of V1-cal was completely abrogated and without effect compared to TRPV1 knockout rat controls (FIG. 18).

FIG. 18: V1-cal selectively targets TRPV1 and summary figure. A. Experimental protocol for knockout TRPV1 rats B. Infarct size per area at risk % for TRPV1 knockout rats. C. Representative images of 2 hearts for each experiment. D. Summary figure: V1-cal acts as a decoy for the low abundance protein TRPV1 and limits the inducible interaction of calcineurin with TRPV1 when TRPV1 is activated by cellular stress. This limits changes in mitochondrial membrane potential and mitigates cardiac reperfusion injury.

Conclusion: TRPV1 is localized at the mitochondria in cardiomyocytes and regulates mitochondrial membrane potential through an interaction with calcineurin. V1-cal was developed which substantially reduces reperfusion injury by inhibiting the interaction of calcineurin with TRPV1. These data suggest that TRPV1 is an end-effector of cardioprotection and modulating the TRPV1 protein interaction with calcineurin limits reperfusion injury. The present disclosure describes a unique role for TRPV1 in the cardiomyocyte to regulate mitochondrial membrane potential and a new therapeutic agent V1-cal, which specifically targets the TRPV1 protein-protein interaction with calcineurin to reduce reperfusion injury. These results study suggest that TRPV1 is present in the cardiomyocyte and functions to regulate mitochondrial membrane potential. Shifting the TRPV1 channel more to a closed state substantially mitigates reperfusion injury. These findings suggest a peptide agent can limit changes in mitochondrial membrane potential and be useful to maintain mitochondrial integrity during states of cellular stress.

Example 2

TRPV1 T704 is a Critical Regulator of Trafficking in Neuronal F11 Cells

FIGS. 20-demonstrate neuronal expression and trafficking of the TRPV1 channel FIG. 20, panels A-C, show confocal images of transiently transfected F11 cells expressing wild type TRPV1 (TRPV1-WT), TRPV1-T704A, and TRPV1-T704E channels as shown in panel A, panel B, and panel C, respectively. TRPV1-T704A channels more efficiently express at the cell surface when compared to TRPV1-WT or TRPV-T704E.

FIG. 21, panels A-B. Panel A shows the fluorescence activated cell sorter analysis of transiently transfected live F11 cells for cell surface expression of TRPV1-WT, TPV1-T704A, or TRPV1-T704E channels with a fluorescent conjugated antibody recognizing the TRPV1 channel surface expression. The relative fluorescent intensity of transiently transfected cells expressing TRPV1 channels at the cell surface (cell count or number of surface cells detected expressing TRPV1) versus the corresponding fluorescent intensity. Panel B show the percent difference in the total number of cells detected at the cell surface expressing TRPV1.

FIG. 22, panels A-B, show results of a western blot (panel A) depicting whole cell lysate obtained from un-transfected F11 cells and F11 cells transfected with TRPV1-WT, TRPV1-T704A, or TRPV1-T704E channel F11 cells expressing TRPV1-T704A channels display a greater amount of mature, glycosylated, protein than either F11 cells expressing for TRPV1-WT or TRPV1-T704E (Panel B). F-actin was used as a loading control. Panel B shows the quantification of the percentage maturation (glycosylation) of TRPV1 channels from the blot above. n=4/group. Significance was determined using One-Way ANOVA with Dunnetts comparison (*p<0.05).

Example 3

Figure 23:
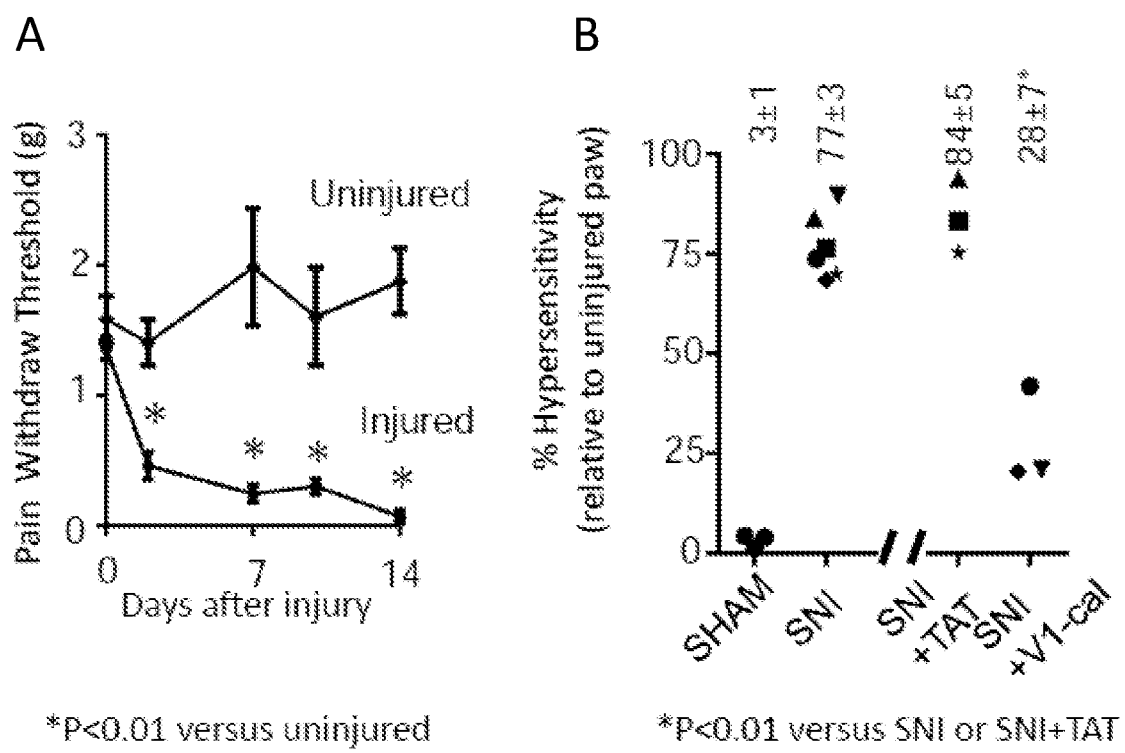
FIG. 23, panels A-B, demonstrates that peptidic agent V1-cal reduces hypersensitivity in nerve injury model of chronic pain. Panel A shows graphs of mechanical threshold testing for spared nerve injury (SNI) model in C57/BL6 mice. Male C57/BL6 mice were subjected to spare nerve injury model (Panel A). After spared nerve injury, rodents were monitored for mechanical withdraw using von Frey hairs for a period of 2 weeks. Thresholds were measured by von Frey hairs comparing uninjured (non-spared nerve injury) to injured (spared nerve injury) hind leg. 2 weeks after spared nerve injury, the rodents were given either V1-cal or vehicle (TAT) via an osmotic infusion pump for 2 additional weeks as a rescue therapy (Panel B). Mechanical pain sensitivity thresholds were measured and compared to the uninjured paw. Rodents receiving exemplary peptidic agent V1-cal had a significant reduction in hypersensitivity compared to rodents receiving vehicle (panel B).

Peptidic Agent V1-cal Reduces Hypersensitivity in Nerve Injury Model of Chronic Pain FIG. 23, panels A-B, shows graphs of mechanical threshold testing for spared nerve injury (SNI) model in C57/BL6 mice. Baseline data was collected for 2 weeks. Spared nerve injury model of chronic pain was performed on rodents after collecting baseline data. The mechanical threshold was then measured for 2 weeks. Rodents were then treated with V1-cal or TAT for 2 weeks. Panel A: Male C57/BL6 mice were subjected to spare nerve injury model. After spared nerve injury, rodents were monitored for mechanical withdraw using von Frey hairs for a period of 2 weeks. Thresholds were measured by von Frey hairs comparing uninjured (non-spared nerve injury) to injured (spared nerve injury) hind leg. Panel B: 2 weeks after spared nerve injury, the same rodents were given either V1-cal or vehicle (TAT) via an osmotic infusion pump (1 mg/kg/day) for 2 additional weeks as a rescue therapy. Mechanical pain sensitivity thresholds were measured and compared to the uninjured paw. Rodents receiving V1-cal had a significant reduction in hypersensitivity compared to rodents receiving vehicle. n=3/group, *P<0.05. SHAM refers to serious harm and morbidity scale.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended embodiments.

Notwithstanding the appended claims, the disclosure set forth herein is also described by the following clauses.

Clause 1. An isolated peptidic agent that selectively modulates the interaction between calcineurin and a calcineurin-binding protein partner.

Clause 2. The agent of clause 1, wherein the calcineurin-binding protein partner is a transient receptor potential vanilloid (TRPV) channel Clause 3. The agent of clause 2, wherein the TRPV channel is TRPV1, and the agent comprises a sequence having 70% or more sequence identity (e.g., 75% or more, 80% or more, 85% or more, 90% or more or 95% or more) to one of the following sequences:

P1: RAITILDTEKS (SEQ ID NO: 4)

P2: QRAITILDTEKSFLKCMRKAFR (SEQ ID NO: 7)

P3: QRAITILDTEKS (SEQ ID NO: 8)

P4: AITILDTEKSFLK (SEQ ID NO: 9)

P5: ITILDTEKSFLKCMRKAFR (SEQ ID NO: 10)

P6: ITILDTEKSFLKCMRK (SEQ ID NO: 11)

P7: AITILDTEKSFLK (SEQ ID NO: 12)

P8: ITILDTEKSF; (SEQ ID NO: 13)
or

P9: ITILDTEKSFLKCM. (SEQ ID NO: 14)

Clause 4. The agent of clause 2, wherein the TRPV channel is TRPV2, TRPV3, TRPV4, TRPV5 or TRPV6, and the agent comprises a sequence having 70% or more sequence identity (e.g., 75% or more, 80% or more, 85% or more, 90% or more or 95% or more) to one of the following sequences:

QKAISVLEMENG, (SEQ ID NO: 18)

QRARTILEFEKM, (SEQ ID NO: 16)

QWATTILDIERS, (SEQ ID NO: 17)

QVVATTVMLERKL (SEQ ID NO: 19)
or

QIVATTVMLERKL. (SEQ ID NO: 20)

Clause 5. The agent of any one of clauses 1-4, wherein the agent further comprises a linked spacer.

Clause 6. The agent of any one of clauses 1-4, wherein the agent further comprises a linked cell permeable peptide.

Clause 7. The agent of clause 6, wherein the cell permeable peptide is a TAT peptide.

Clause 8. The agent of clause 7, wherein the TAT peptide comprises a sequence having 80% or more sequence identity to YGRKKRRQRRR (SEQ ID NO:96).

Clause 9. The agent of any one of clauses 1-8, wherein the agent selectively inhibits the interaction between calcineurin and TRPV1.

Clause 10. The agent of any one of clauses 1-8, wherein the agent selectively inhibits the interaction between calcineurin and one of TRPV2, TRPV3, TRPV4, TRPV5 or TRPV6.

Clause 11. The agent of any one of clauses 1-10, wherein the peptidic agent is cyclized.

Clause 12. The agent of any one of clauses 1-11, wherein the peptidic agent comprises a stapled peptide.

Clause 13. The agent of any one of clauses 1-11, wherein the peptidic agent comprises a stitched peptide.

Clause 14. The agent of any one of clauses 1-13, wherein the peptidic agent comprises a non-natural amino acid substitution (e.g., relative to one of the sequences described herein).

Clause 15. The agent of any one of clauses 1-14, wherein the peptidic agent comprises two or more non-natural amino acid substitutions (e.g., relative to one of the sequences described herein).

Clause 16. A pharmaceutical composition comprising:
a peptidic agent that selectively modulates the interaction between calcineurin and a calcineurin-binding protein partner; and a pharmaceutically acceptable excipient.

Clause 17. The composition of clause 16, wherein the calcineurin-binding protein partner is a TRPV channel Clause 18. The composition of clause 16 or 17, wherein the peptidic agent is the agent of any one of clause 1-15.

Clause 19. The composition of clause 17, wherein the TRPV channel is TRPV1, and the agent comprises a sequence having 70% or more sequence identity identity (e.g., 75% or more, 80% or more, 85% or more, 90% or more or 95% or more) to one of the following sequences:

```
                            (SEQ ID NO: 4)
P1: RAITILDTEKS (SEQ ID NO: 7)
P2: QRAITILDTEKSFLKCMRKAFR (SEQ ID NO: 8)
P3: QRAITILDTEKS (SEQ ID NO: 9)
P4: AITILDTEKSFLK (SEQ ID NO: 10)
P5: ITILDTEKSFLKCMRKAFR (SEQ ID NO: 11)
P6: ITILDTEKSFLKCMRK (SEQ ID NO: 12)
P7: AITILDTEKSFLK (SEQ ID NO: 13)
P8: ITILDTEKSF;
or (SEQ ID NO: 14)
P9: ITILDTEKSFLKCM.
```

Clause 20. The composition of clause 17, wherein the TRPV channel is TRPV2, TRPV3, TRPV4, TRPV5 or TRPV6, and the agent comprises a sequence having 70% or more sequence identity (e.g., 75% or more, 80% or more, 85% or more, 90% or more or 95% or more) to one of the following sequences:

```
                    (SEQ ID NO: 18)
QKAISVLEMENG, (SEQ ID NO: 16)
QRARTILEFEKM, (SEQ ID NO: 17)
QWATTILDIERS, (SEQ ID NO: 19)
QVVATTVMLERKL
or
                    (SEQ ID NO: 20)
QIVATTVMLERKL.
```

Clause 21. The composition of any one of clauses 16-20, wherein the agent further comprises a linked spacer.

Clause 22. The composition of any one of clauses 16-21, wherein the agent further comprises a linked cell permeable peptide.

Clause 23. The composition of clause 22, wherein the cell permeable peptide is a transactivator of transcription (TAT) peptide.

Clause 24. The composition of clause 23, wherein the TAT peptide comprises sequence having 70% or more sequence identity (e.g., 75% or more, 80% or more, 85% or more, 90% or more or 95% or more) to YGRKKRRQRRR (SEQ ID NO:96).

Clause 25. The composition of any one of clauses 16-24, wherein the peptidic agent is cyclized.

Clause 26. The composition of any one of clauses 16-25, wherein the peptidic agent comprises a stapled peptide.

Clause 27. The composition of any one of clauses 16-25, wherein the peptidic agent comprises a stitched peptide.

Clause 28. The composition of any one of clauses 16-27, wherein the peptidic agent comprises a non-natural amino acid substitution.

Clause 29. The composition of any one of clauses 11-28, wherein the peptidic agent comprises two or more non-natural amino acid substitutions.

Clause 30. A method of modulating a TRPV channel in a cell, the method comprising: contacting the cell with a peptidic agent that selectively modulates the interaction between calcineurin and a TRPV channel (e.g., an agent comprises a sequence having 70% or more sequence identity (e.g., 75% or more, 80% or more, 85% or more, 90% or more or 95% or more) to one of the following sequences:

```
                    (SEQ ID NO: 8)
QRAITILDTEKS, (SEQ ID NO: 18)
QKAISVLEMENG, (SEQ ID NO: 16)
QRARTILEFEKM, (SEQ ID NO: 17)
QWATTILDIERS, (SEQ ID NO: 19)
QVVATTVMLERKL
or
                    (SEQ ID NO: 20))
QIVATTVMLERKL.
```

Clause 31. The method of clause 30, wherein the TRPV channel is TRPV1 and the agent comprises the sequence QRAITILDTEKS (SEQ ID NO:8).

Clause 32. The method of any one of clauses 30-31, wherein modulating a TRPV1 channel comprises keeping the TRPV1 channel in an inactive state.

Clause 33. The method of clause 32, wherein keeping the TRPV1 channel in an inactive state limits changes in the mitochondrial membrane potential of the cell.

Clause 34. A method for treating a condition in a subject, the method comprising: administering to the subject an effective amount of a peptidic agent that selectively modulates the interaction between calcineurin and a TRPV channel Clause 35. The method of clause 34, wherein the agent comprises a sequence having 70% or more sequence identity (e.g., 75% or more, 80% or more, 85% or more, 90% or more or 95% or more) to one of the following sequences:

```
                    (SEQ ID NO: 8)
QRAITILDTEKS, (SEQ ID NO: 18)
QKAISVLEMENG, (SEQ ID NO: 16)
QRARTILEFEKM, (SEQ ID NO: 17)
QWATTILDIERS,
```

-continued

QVVATTVMLERKL (SEQ ID NO: 19)
or

QIVATTVMLERKL. (SEQ ID NO: 20)

Clause 36. The method of clause 34, wherein the agent is an agent according to one of clauses 1-15.

Clause 37. The method of clause 34, wherein the agent is composed in a composition according to one of clauses 16-29.

Clause 38. The method of any one of clauses 34-37, wherein the condition in a subject is reperfusion injury.

Clause 39. The method of any one of clauses 34-38, wherein the subject suffered from a myocardial infarction.

Clause 40. The method of any one of clauses 34-38, wherein the subject suffered from a stroke.

Clause 41. The method of any one of clauses 34-38, wherein the subject received an organ transplant.

Clause 42. The method of any one of clauses 34-38, wherein the subject received a percutaneous transluminal coronary angiography.

Clause 43. The method of any one of clauses 34-37, wherein the condition is cardiac hypertrophy.

Clause 44. The method of any one of clauses 34-37, wherein the condition is transplant rejection.

Clause 45. The method of any one of clauses 34-37, wherein the condition is pain (e.g., chronic pain).

Clause 46. The method of any one of clauses 34-45, wherein the peptidic agent is used as an adjuvant to opioids.

Clause 47. The method of any one of clauses 34-37, wherein the condition is osteoporosis.

Clause 48. The method of any one of clauses 34-37, wherein the condition is endothelial dysfunction.

Clause 49. The method of any one of clauses 34-37, wherein the peptidic agent is used as an immunosuppressant.

Clause 50. The method of any one of clauses 34-37, wherein the condition is itch.

Clause 51. The method of any one of clauses 34-50, wherein the peptidic agent is administered via topical application of a cream or patch.

Clause 52. The method of any one of clauses 34-50, wherein the peptidic agent is administered via injection.

Clause 53. The method of any one of clauses 34-50, wherein the peptidic agent is administered intravenously.

Clause 54. The method of any one of clauses 34-50, wherein the peptidic agent is administered as a mouthwash.

Clause 55. The method of any one of clauses 34-54, wherein the peptidic agent is administered in combination with a second agent selected from: a TRPV antagonist, a TRPV agonist, a calcineurin inhibitor and an opiod agent.

Clause 56. A method of screening for a candidate agent for the ability to modulate the interaction between calcineurin and a TRPV channel, the method comprising:

contacting a cell with a candidate agent (e.g., a small molecule) and the peptidic agent of any one of clauses 1-15; and detecting a parameter;

wherein a change in the parameter in the cell as compared to in a cell not contacted with candidate agent indicates that the candidate agent modulates the interaction between calcineurin and a TRPV channel at a site characterized by one of the following sequences:

QRAITILDTEKS, (SEQ ID NO: 8)

QKAISVLEMENG, (SEQ ID NO: 18)

QRARTILEFEKM, (SEQ ID NO: 16)

QWATTILDIERS, (SEQ ID NO: 17)

QVVATTVMLERKL (SEQ ID NO: 19)
or

QIVATTVMLERKL. (SEQ ID NO: 20)

Clause 57. The method of clause 56, wherein the parameter is mitochondrial membrane potential.

Clause 58. The method of clause 56, wherein the parameter is the level of desphosphorylation of a calcineurin substrate.

Clause 59. The method of any one of clauses 56-58, wherein the cell is from an isolated heart.

Clause 60. The method of any one of clauses 56-59, wherein the cell is from an animal.

Clause 61. The method of clause 60, wherein the parameter is myocardial infarct size.

Clause 62. The method of clause 60, wherein the parameter is area at risk/left ventricle percent.

Clause 63. The method of clause 60, wherein the parameter is a hemodynamic parameter selected from: heart rate, blood pressure, rate pressure product, or combinations thereof.

What is claimed is:

1. An isolated peptidic agent that selectively modulates the interaction between calcineurin and a calcineurin-binding protein partner that is a transient receptor potential vanilloid (TRPV) channel, wherein the TRPV channel is TRPV1, and the agent comprises a sequence having 100% sequence identity to ITILDTEKS (SEQ ID NO: 116), wherein the agent further comprises a linked cell permeable peptide.

2. The agent of claim 1, wherein the cell permeable peptide is a TAT peptide.

3. The agent of claim 2, wherein the TAT peptide comprises a sequence having 80% or more sequence identity to YGRKKRRQRRR (SEQ ID NO:96).

4. The agent of claim 1, wherein the agent comprises a sequence having 95% or more sequence identity to a sequence selected from:
P1: RAITILDTEKS (SEQ ID NO: 4),
P2: QRAITILDTEKSFLKCMRKAFR (SEQ ID NO: 7),
P3: QRAITILDTEKS (SEQ ID NO: 8),
P4: AITILDTEKSFLK (SEQ ID NO: 9),
P5: ITILDTEKSFLKCMRKAFR (SEQ ID NO: 10),
P6: ITILDTEKSFLKCMRK (SEQ ID NO: 11),
P7: AITILDTEKSFLK (SEQ ID NO: 12),
P8: ITILDTEKSF (SEQ ID NO: 13), and
P9: ITILDTEKSFLKCM (SEQ ID NO: 14).

5. The agent of claim 1, wherein the agent comprises a sequence having 90% or more sequence identity to RAITILDTEKS (SEQ ID NO: 4).

6. The agent of claim 1, wherein the agent comprises a sequence having 100% sequence identity to RAITILDTEKS (SEQ ID NO: 4).

7. A pharmaceutical composition comprising:
a peptidic agent that selectively modulates the interaction between calcineurin and a calcineurin-binding protein partner that is a TRPV channel, wherein the TRPV channel is TRPV1, and the agent comprises a sequence having 100% sequence identity to ITILDTEKS (SEQ ID NO: 116), wherein the agent further comprises a linked cell permeable peptide; and
a pharmaceutically acceptable excipient.

8. A method of modulating a TRPV channel in a cell, the method comprising:
contacting the cell with a peptidic agent that selectively modulates the interaction between calcineurin and a TRPV channel, wherein the TRPV channel is TRPV1, and the agent comprises a sequence having 100% sequence identity to ITILDTEKS (SEQ ID NO: 116), wherein the agent further comprises a linked cell permeable peptide.

9. The method of claim 8, wherein modulating a TRPV1 channel comprises keeping the TRPV1 channel in an inactive state.

10. The method of claim 9, wherein keeping the TRPV1 channel in an inactive state limits changes in the mitochondrial membrane potential of the cell.

* * * * *